US011657921B2

(12) United States Patent
Zimmerman et al.

(10) Patent No.: US 11,657,921 B2
(45) Date of Patent: May 23, 2023

(54) ARTIFICIAL INTELLIGENCE BASED CARDIAC EVENT PREDICTOR SYSTEMS AND METHODS

(71) Applicants: Tempus Labs, Inc., Chicago, IL (US); Geisinger Clinic, Danville, PA (US)

(72) Inventors: Noah Zimmerman, Redwood City, CA (US); Brandon Fornwalt, Chicago, IL (US); John Pfeifer, Chicago, IL (US); Ruijun Chen, Chicago, IL (US); Arun Nemani, Chicago, IL (US); Greg Lee, Chicago, IL (US); Steve Steinhubl, Chicago, IL (US); Christopher Haggerty, Danville, PA (US); Sushravya Raghunath, Danville, PA (US); Alvaro Ulloa-Cerna, Danville, PA (US); Linyuan Jing, Danville, PA (US); Thomas Morland, Danville, PA (US)

(73) Assignees: Tempus Labs, Inc., Chicago, IL (US); Geisinger Clinic, Danville, PA (US)

( * ) Notice: Subject to any disclaimer, the term of this patent is extended or adjusted under 35 U.S.C. 154(b) by 0 days.

(21) Appl. No.: 17/829,356

(22) Filed: May 31, 2022

(65) Prior Publication Data
US 2022/0378379 A1 Dec. 1, 2022

Related U.S. Application Data

(63) Continuation-in-part of application No. 17/026,092, filed on Sep. 18, 2020.
(Continued)

(51) Int. Cl.
*G16H 50/30* (2018.01)
*G16H 50/20* (2018.01)
(Continued)

(52) U.S. Cl.
CPC ........... *G16H 50/30* (2018.01); *A61B 5/0006* (2013.01); *A61B 5/28* (2021.01); *A61B 5/318* (2021.01);
(Continued)

(58) Field of Classification Search
CPC ........ G16H 50/20; A61B 5/7275; A61B 5/318
(Continued)

(56) References Cited

U.S. PATENT DOCUMENTS

| 7,801,591 B1 | 9/2010 | Shusterman |
| 10,667,680 B2 | 6/2020 | Gupta et al. |

(Continued)

FOREIGN PATENT DOCUMENTS

| CN | 106510686 A | * 3/2017 | ........... A61B 5/0006 |
| KR | 20200077852 A | 7/2020 | |

(Continued)

OTHER PUBLICATIONS

Arvanitis et al., Identification of V1221 (Val122Ile) Transthyretin Cardiac Amyloidosis (ATTR) Using Serum Retinol-Binding Protein 4 (RBP4) and a Clinical Prediction Model, JAMA Cardiol., 2017, 2(3):305-313.
(Continued)

*Primary Examiner* — Carl H Layno
*Assistant Examiner* — Michael J Lau
(74) *Attorney, Agent, or Firm* — Quarles & Brady LLP

(57) ABSTRACT

A method and system for predicting the likelihood that a patient will suffer from a cardiac event is provided. The method includes receiving electrocardiogram data associated with the patient, providing at least a portion of the electrocardiogram data to a trained model, receiving a risk score indicative of the likelihood the patient will suffer from the cardiac event within a predetermined period of time from when the electrocardiogram data was generated, and out-
(Continued)

putting the risk score to at least one of a memory or a display for viewing by a medical practitioner or healthcare administrator. The system includes at least one processor executing instructions to carry out the steps of the method.

29 Claims, 46 Drawing Sheets

Related U.S. Application Data

(60) Provisional application No. 63/194,923, filed on May 28, 2021, provisional application No. 63/202,436, filed on Jun. 10, 2021, provisional application No. 63/224,850, filed on Jul. 22, 2021, provisional application No. 62/902,266, filed on Sep. 18, 2019, provisional application No. 62/924,529, filed on Oct. 22, 2019, provisional application No. 63/013,897, filed on Apr. 22, 2020.

(51) Int. Cl.
*A61B 5/318* (2021.01)
*A61B 5/00* (2006.01)
*A61B 5/28* (2021.01)
*G06K 9/62* (2022.01)

(52) U.S. Cl.
CPC ........... *A61B 5/7275* (2013.01); *G16H 50/20* (2018.01); *G06K 9/6259* (2013.01)

(58) Field of Classification Search
USPC ........................................................ 600/301
See application file for complete search history.

(56) References Cited

U.S. PATENT DOCUMENTS

| | | | |
|---|---|---|---|
| 10,827,982 B2 | 11/2020 | Sitek | |
| 2007/0214013 A1 | 9/2007 | Silverman | |
| 2009/0093686 A1* | 4/2009 | Hu | G16Z 99/00 600/300 |
| 2011/0295134 A1 | 12/2011 | DeBauche | |
| 2015/0112182 A1* | 4/2015 | Sharma | A61B 5/7264 600/408 |
| 2015/0235143 A1 | 8/2015 | Eder | |
| 2015/0324527 A1 | 11/2015 | Siegel et al. | |
| 2016/0022162 A1 | 1/2016 | Ong et al. | |
| 2016/0135706 A1 | 5/2016 | Sullivan et al. | |
| 2017/0357756 A1 | 12/2017 | Fidone et al. | |
| 2018/0333104 A1 | 11/2018 | Sitek | |
| 2020/0176122 A1 | 6/2020 | Teplitzky et al. | |
| 2020/0226757 A1 | 7/2020 | Hare, II et al. | |
| 2020/0337773 A1* | 10/2020 | Rawlinson | G06T 7/194 |
| 2020/0353271 A1 | 11/2020 | Dani et al. | |
| 2020/0397313 A1 | 12/2020 | Attia et al. | |
| 2021/0000347 A1* | 1/2021 | Stump | A61B 5/02444 |
| 2021/0027194 A1 | 1/2021 | Monaghan et al. | |
| 2021/0059540 A1 | 3/2021 | Peterson et al. | |
| 2021/0076960 A1* | 3/2021 | Fornwalt | A61B 5/7275 |
| 2021/0085215 A1 | 3/2021 | Auerbach et al. | |
| 2021/0085397 A1* | 3/2021 | Passerini | G16H 50/30 |
| 2021/0089921 A1 | 3/2021 | Aghdasi et al. | |
| 2021/0110930 A1 | 4/2021 | Park et al. | |
| 2021/0125722 A1* | 4/2021 | Sherkat | G06N 3/0454 |
| 2021/0150693 A1* | 5/2021 | Fornwalt | G16H 40/67 |
| 2021/0153761 A1 | 5/2021 | Jung et al. | |
| 2021/0259560 A1 | 8/2021 | Venkatraman et al. | |
| 2021/0345934 A1 | 11/2021 | Landgraf et al. | |
| 2022/0229071 A1 | 7/2022 | Rhyne et al. | |

FOREIGN PATENT DOCUMENTS

| | | |
|---|---|---|
| WO | 2020004369 A1 | 1/2020 |
| WO | 2021071142 A1 | 4/2021 |

OTHER PUBLICATIONS

Ashburner et al., Design and Rationale of a Pragmatic Trial Integrating Routine Screening for Atrial Fibrillation at Primary Care Visits: The VITAL-AF Trial, American Heart Journal, 2019, 215:147-156.

Attia et al., An Artificial Intelligence-Enabled ECG Algorithm for the Identification of Patients with Atrial Fibrillation During Sinus Rhythm: A Retrospective Analysis of Outcome Prediction, The Lancet, 2019, 394(10201):861-867.

Freedman et al., Stroke Prevention in Atrial Fibrillation, The Lancet, 2016, 388(10046):806-817.

Gladstone et al., Screening for Atrial Fibrillation in the Older Population: A Randomized Clinical Trial, JAMA Cardiology, 2021, 6(5):558-567.

Hindricks et al., 2020 ESC Guidelines for the Diagnosis and Management of Atrial Fibrillation Developed in Collaboration with the European Association for Cardio-Thoracic Surgery (EACTS), European Heart Journal, 2020, 42(5):373-498.

Huda et al., A Machine Learning Model for Identifying Patients at Risk for Wild-Type Transthyretin Amyloid Cardiomyopathy, Nature Communications, 2021, 12:2725, pp. 1-12.

Khurshid et al., ECG-Based Deep Learning and Clinical Risk Factors to Predict Atrial Fibrillation, Circulation, 2022, 145(2):122-133.

Kyriakou et al., Diagnosis of Cardiac Amyloidosis: A Systematic Review on the Role of Imaging and Biomarkers, BMC Cardiovascular Disorders, 2018, 18:221, pp. 1-11.

Lip et al., Refining Clinical Risk Stratification for Predicting Stroke and Thromboembolism in Atrial Fibrillation Using a Novel Risk Factor-Based Approach: The Euro Heart Survey on Atrial Fibrillation, Chest, 2010, 137(2):263-272.

Martini et al., Deep Learning to Diagnose Cardiac Amyloidosis from Cardiovascular Magnetic Resonance, Journal of Cardiovascular Magnetic Resonance, 2020, 22:84, pp. 1-11.

Poterucha et al., Deep Learning Analysis of Cardiac Testing for the Detection of Cardiac Amyloidosis, JACC, 2021, 77(18):529.

Raghunath et al., Prediction of Mortality from 12-lead Electro Cardiogram Voltage Data Using a Deep Neural Network, Nature Medicine, 2020, 26(6):886-891.

Raghunath et al., Deep Neural Networks can Predict New-Onset Atrial Fibrillation from the 12-lead ECG and Help Identify Those at Risk of Atrial Fibrillation-Related Stroke, Circulation, 2021, 143(13):1287-1298.

Singer et al., ReducinG stroke by screening for UndiAgnosed atRial fibrillation in elderly inDividuals (GUARD-AF): Rationale and Design of the GUARD-AF Randomized Trial of Screening for Atrial Fibrillation with a 14-day Patch-Based Continuous ECG Monitor, American Heart Journal, 2022, 249:76-85.

Steinhubl et al., Effect of a Home-Based Wearable Continuous ECG Monitoring Patch on Detection of Undiagnosed Atrial Fibrillation: The mSToPS Randomized Clinical Trial, JAMA, 2018, 320(2):146-155.

Suresh et al., Advanced Cardiac Amyloidosis Associated with Normal Interventricular Septum Thickness: An Uncommon Presentation of Infiltrative Cardiomyopathy, J Am Soc Echocardiogr, 2014, 27(4):440-447.

Svennberg et al., Mass Screening for Untreated Atrial Fibrillation: The Strokestop Study, Circulation, 2015, 131(25):2176-2184.

Topol, Digital Medicine—What's Lurking in Your Electrocardiogram?, The Lancet, 2021, 397:785.

US Preventive Services Task Force, Screening for Atrial Fibrillation, US Preventive Services Task Force Recommendation Statement, JAMA, 2022, 327(4):360-367.

Weimann et al., Transfer Learning for ECG Classification, Scientific Reports, 2021, 11:5251, pp. 1-12.

Wolf et al., Atrial Fibrillation as an Independent Risk Factor for Stroke: The Framingham Study, Stroke, 1991, 22(8):983-988.

PCT International Search Report and Written Opinion, PCT/US2022/031663, dated Aug. 19, 2022, 15 pages.

PCT International Search Report and Written Opinion, PCT/US2022/031665, dated Aug. 19, 2022, 16 pages.

(56) References Cited

OTHER PUBLICATIONS

PCT International Search Report and Written Opinion, PCT/US2022/031670, dated Aug. 18, 2022, 9 pages.
Apple Inc., De Novo Classification Request for ECG App, 2018, 15 pages.

* cited by examiner

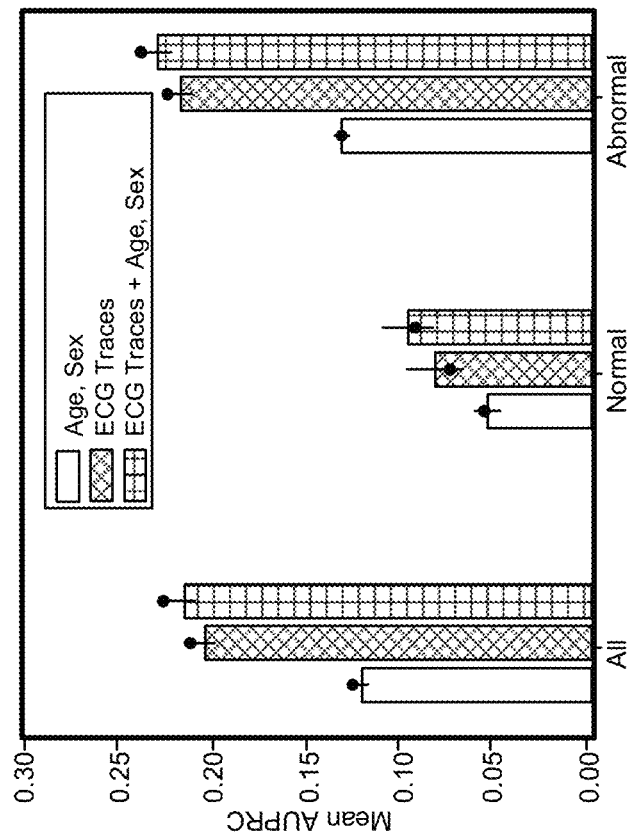
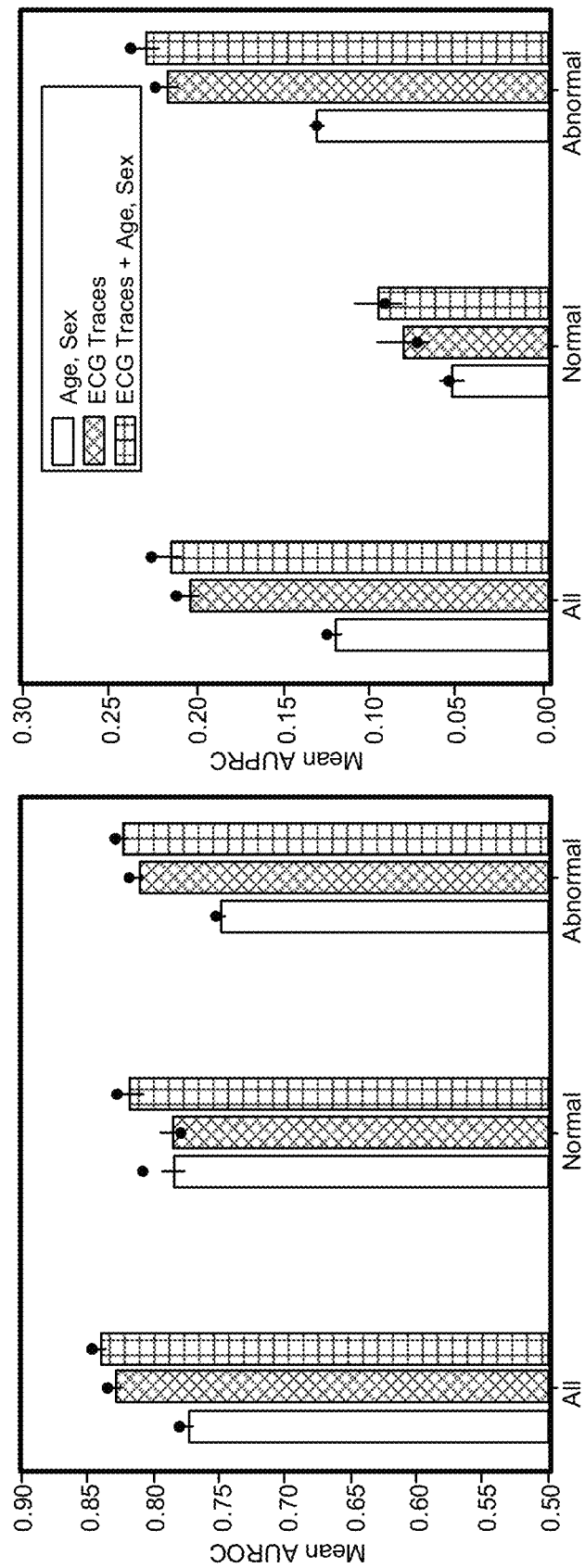
Fig. 7A
Fig. 7B

Fig. 22A The incidence-free proportion curve for the two predicted groups (likelihood threshold = 0.5) with the available follow-up. 22B The top % patients with highest risk and the positive predictive value across all the operating points of the model. There are 237,060 patients in the entire population such that the highest 1% at risk consists of 2,370 patients.

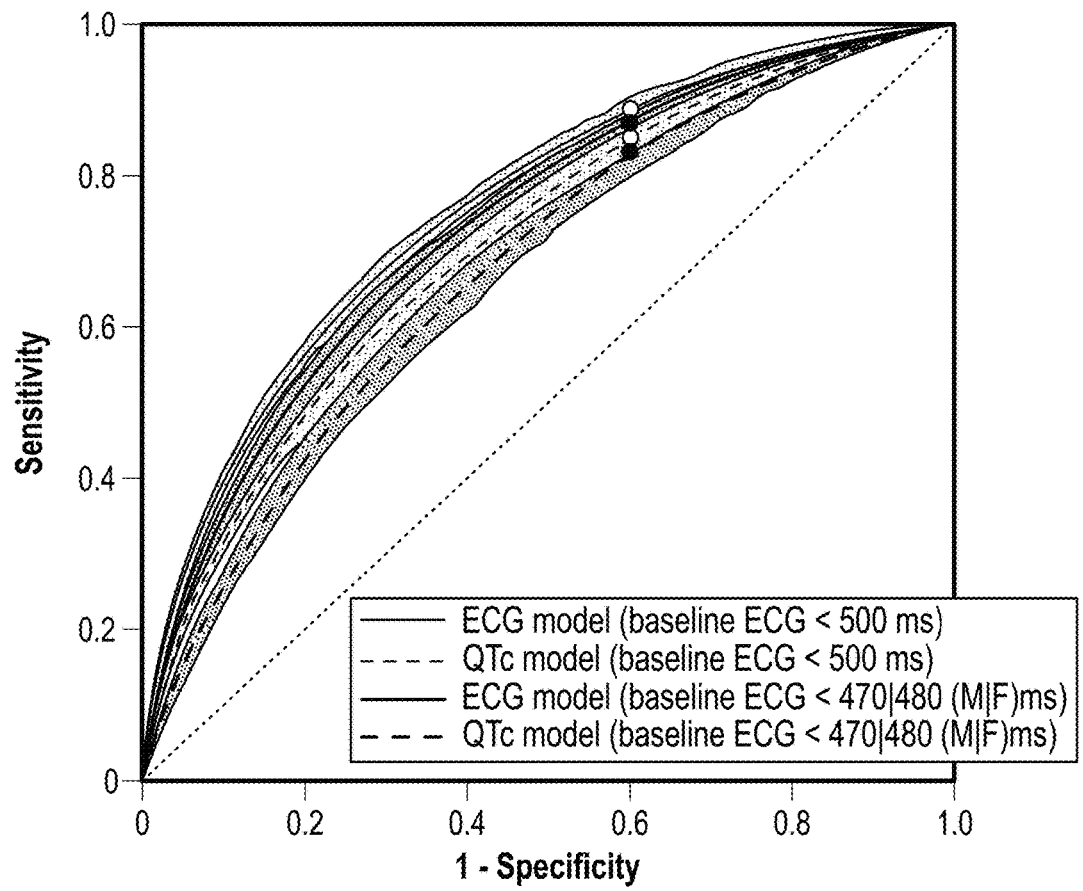

| Baseline ECG | < 500 ms | | < 470 \| 480 ms (Male \| Female) | |
|---|---|---|---|---|
| Risk prediction | ECG Model | QTc model | ECG Model | QTc model |
| AUC [95% CI] | 0.756 [0.748, 0.765] | 0.710 [0.694, 0.726] | 0.736 [0.728, 0.744] | 0.680 [0.662 - 0.697] |
| Sensitivity [95% CI] | 88.7 [82.5 - 94.9] | 84.3 [76.0 - 92.6] | 87.3 [80.2 - 94.4] | 82.4 [73.6 - 91.3] |
| NPV [95% CI] | 94.9 [93.5 - 96.3] | 93.0 [92.0 - 94.1] | 95.1 [93.7 - 96.5] | 93.3 [92.3 - 94.3] |
| % LQT events | 16.2 [15.9 - 16.5] | | 14.2 [14.0 - 14.3] | |

(A) The illustration of the mean receiver operating characteristic (ROC) curves for ECG model and QTc model for the baseline ECGs with QTc <500 ms and <470|480 (Male | Female) across 5-folds with shaded confidence interval (CI) and example potential operating point;
(B) Summary of model performance in terms of area under ROC curve (AUC), sensitivity and negative predictive value (NPV) for the chosen operating point (at specificity of 40%).

Fig. 23

ARTIFICIAL INTELLIGENCE BASED CARDIAC EVENT PREDICTOR SYSTEMS AND METHODS

CROSS-REFERENCE TO RELATED APPLICATIONS

This application claims the benefit of U.S. provisional application 63/194,923, filed May 28, 2021, U.S. provisional application 63/202,436, filed Jun. 10, 2021, and U.S. provisional application 63/224,850, filed Jul. 22, 2021.

This application incorporates by reference in their entirety and for all purposes U.S. Provisional Patent Application No. 62/902,266, filed Sep. 18, 2019, U.S. Provisional Patent Application No. 62/924,529, filed Oct. 22, 2019, and U.S. Provisional Patent Application No. 63/013,897, filed Apr. 22, 2020.

This application also incorporates by reference and in their entirety for all purposes, U.S. Patent Publication 2021/0076960, published Mar. 18, 2021, U.S. Provisional Patent Application No. 63/194,923, filed May 28, 2021, U.S. Provisional Patent Application No. 63/202,436, filed Jun. 10, 2021, and U.S. Provisional Patent Application No. 63/224,841, filed Jul. 22, 2021.

STATEMENT REGARDING FEDERALLY SPONSORED RESEARCH OR DEVELOPMENT

Not applicable.

BACKGROUND OF THE DISCLOSURE

The field of the disclosure is predictive ECG testing and more specifically a system and process for predicting a future medical or health condition using deep learning to associate "current" ECG results with future medical conditions.

Medical physicians routinely diagnose patient conditions and prescribe solutions to eliminate or minimize the effects of those conditions. For instance, when a patient has a bacterial infection, a physician may prescribe antibiotics which are known to kill bacteria. In addition, where specific patient conditions are known to commonly be precursors to subsequent medical events, a physician may prescribe solutions that mitigate the effects of the subsequent conditions. For instance, in the case of a patient that is suffering from atrial fibrillation ("AF" or "Afib"); e.g., quivering or irregular heartbeat (arrhythmia) that can lead to blood clots, stroke, heart failure and other cardiovascular-related complications), a physician may prescribe a blood thinner medication that mitigates the likelihood of subsequent stroke.

In the case of most health conditions, the efficacy (e.g., ultimate ability to eliminate or mitigate the condition and/or condition effects) of treatment plans is related to how early the condition is detected. Early detection typically means more treatment options that result in either a complete/quicker recovery and/or a less severe clinical outcome. Thus, for instance, if a physician detects AF immediately after it starts (or ideally immediately before it begins) as opposed to years thereafter, likelihood of treatment success can increase appreciably. This is particularly important for diseases like AF where patients often are unaware that they even have this potentially dangerous condition, and they present to the hospital with irreparable damage to the brain (in the form of a stroke) instead of being treated before that damage happens.

Similarly, in many cases, if a physician can discern a relatively high likelihood that a currently healthy patient will suffer a specific medical condition prior to occurrence of that condition, the patient can be prescribed a treatment plan designed to help avoid the condition in the future. For example, in the case of AF, if a physician is able to discern that a patient that does not currently suffer AF has an appreciable risk of AF in the future, that patient can be counseled on ways to change his or her lifestyle, or increase monitoring for example with a wearable device to detect AF, so as to prevent or reduce the possibility of future bad outcomes related to AF, such as stroke. For instance, it is believed that the likelihood of AF in a patient currently with no prior history of AF can be reduced appreciably by lifestyle choices including getting regular physical activity, eating a heart-healthy diet, managing high blood pressure, avoiding excessive amounts of alcohol and caffeine, not smoking and maintaining a healthy weight and ideally these choices should be selected by anyone who has a substantial risk of future AF.

The electrocardiogram (ECG) is perhaps the most widely used cardiovascular diagnostic test in the world, with the vast majority of people undergoing this test at some point in their life. Acquisition of an electrocardiogram involves any measurement of electrical potentials at various locations throughout the surface of the body that are used to derive a voltage difference between the two locations. This voltage difference is then plotted as a function of time, for example after acquiring approximately 250-500 voltage samples per second. This plot of voltage as a function of time forms the basis of an ECG and is referred to as an ECG trace. Since all muscles create electrical voltage differences during their normal function, and the heart is essentially a large muscle, various aspects of heart function can be derived from these voltage differences (for example, whether the heart is beating fast or slow or whether certain parts of the heart are abnormally enlarged). Thus, analysis of an ECG is used to diagnose and treat many different heart diseases.

ECGs can be acquired using a minimum of 2 body surface potential recordings (such that a voltage difference can be calculated from the subtraction of the two electrical potentials). When only one voltage difference is acquired typically for a duration of at least 10 seconds, this is known as a "rhythm strip". One common ECG is the 12-lead ECG where voltage differences are acquired in 12 different directions (or "leads") across the surface of the body. Typically, these are acquired while the patient is not performing physical activity ("at rest"), however, they can also be acquired during strenuous activity ("at stress"). While the resting 12-lead ECG is by far the most commonly acquired type of ECG, there is no limit to the number of different "leads" that can be acquired for an ECG. Machines that acquire ECGs are ubiquitous in current clinical practice and consist of electrodes that are attached to the surface of a patient's body which are then connected to multiple wires and a machine which can measure the electrical potential of each wire. This machine can then calculate the voltage differences between the different locations and ultimately generate ECG traces. The ECG traces are visually examined by a physician to identify any irregularities. AF is one of many irregularities then can be identified from ECG traces.

While conventional visual ECG analysis by a trained physician appears to work well for assessing whether a patient currently has AF, conventional ECG analysis does not work well for forecasting likelihood of future AF or other medical events (e.g., heart attacks, stroke, death) that may result from future AF.

Population-based screening for AF is challenging. The yearly incidence of AF in the general population is low with reported incidence rates of less than 10 per 1000 person years under the age of 70. AF is often paroxysmal with many episodes lasting less than 24 hours. Currently, the most common screening strategy is opportunistic pulse palpation, sometimes in conjunction with a 12-lead electrocardiogram (ECG) during routine medical visits. This strategy may be appropriate in certain populations. However, this strategy may miss many cases of AF.

To this end, even to the trained eye of a physician, there is no way to ascertain likelihood of future AF from analyzing an ECG trace that does not currently include features consistent with AF. Thus, where a physician determines that an ECG trace has no evidence of AF, the patient is simply instructed that he/she does not currently have AF without any sense of future AF likelihood or the likelihood of future AF related complications.

SUMMARY OF THE DISCLOSURE

In one aspect, the present disclosure provides a method including receiving electrocardiogram data associated with a patient and an electrocardiogram configuration including a plurality of leads and a time interval, the electrocardiogram data including, for each lead included in the plurality of leads, voltage data associated with at least a portion of the time interval, receiving an age value associated with the patient, receiving a sex value associated with the patient, providing the age value, the sex value, and at least a portion of the electrocardiogram data to a trained model, the trained model being trained to generate a risk score based on input electrocardiogram data associated with the electrocardiogram configuration and supplementary information associated with the patient, receiving a risk score indicative of a likelihood the patient will suffer from a condition within a predetermined period of time from when the electrocardiogram data was generated, and outputting the risk score to at least one of a memory or a display for viewing by a medical practitioner or healthcare administrator.

The method may further include receiving electronic health record data associated with the patient and providing at least a portion of the electronic health record data to the trained model. The electronic health record data may include at least one of a blood cholesterol measurement, a blood cell count, a blood chemistries lab, a troponin level, a natriuretic peptide level, a blood pressure, a heart rate, a respiratory rate, an oxygen saturation, a cardiac ejection fraction, a cardiac chamber volume, a heart muscle thickness, a heart valve function, a diabetes diagnosis, a chronic kidney disease diagnosis, a congenital heart defect diagnosis, a cancer diagnosis, a procedure, a medication, a referral for cardiac rehabilitation, or a referral for dietary counseling.

The method may further include determining that the risk score is above a predetermined threshold associated with the condition, in response to determining that the risk score is above the predetermined threshold, generating a report including information and/or links to sources associated with at least one of treatments for the condition or causes of the condition, and outputting the report to at least one of a memory or a display for viewing by a medical practitioner or healthcare administrator.

In the method, the period of time may be one year.

In the method, the period of time may be selected from a range of one day to thirty years.

In the method, the trained model may include a deep neural network including a plurality of branches. The portion of the electrocardiogram data provided to the trained model may be provided to the plurality of branches.

In the method, the trained model may include a deep neural network including a convolutional component and a dense layer component. The convolutional component may include an inception block including a plurality of convolutional layers.

In the method, the plurality of leads may include a lead I, a lead V2, a lead V4, a lead V3, a lead V6, a lead II, a lead VI, and a lead V5. The electrocardiogram data may include first voltage data associated with the lead I and a first portion of the time interval, second voltage data associated with the lead V2 and a second portion of the time interval, third voltage data associated with the lead V4 and a third portion of the time interval, fourth voltage data associated with the lead V3 and the second portion of the time interval, fifth voltage data associated with the lead V6 and the third portion of the time interval, sixth voltage data associated with the lead II and the first portion of the time interval, seventh voltage data associated with the lead II and the second portion of the time interval, eighth voltage data associated with the lead II and the third portion of the time interval, ninth voltage data associated with the lead VI and the first portion of the time interval, tenth voltage data associated with the lead VI and the second portion of the time interval, eleventh voltage data associated with the lead VI and the third portion of the time interval, twelfth voltage data associated with the lead V5 and the first portion of the time interval, thirteenth voltage data associated with the lead V5 and the second portion of the time interval, and fourteenth voltage data associated with the lead V5 and the third portion of the time interval. The time interval may include a ten second time period, the first portion of the time interval may include a first half of the time interval, the second portion of the time interval may include a third quarter of the time interval, and the third portion of the time interval may include a fourth quarter of the time interval. The trained model may include a first channel, a second channel, and a third channel, and the providing step may include providing the first voltage data, the sixth voltage data, the ninth voltage data, and the twelfth voltage data to the first channel, providing the second voltage data, the fourth voltage data, the seventh voltage data, the tenth voltage data, and the thirteenth voltage data to the second channel, and providing the third voltage data, the fifth voltage data, the eighth voltage data, the eleventh voltage data, and the fourteenth voltage data to the third channel. Each of the plurality of leads may be associated with the time interval.

In the method, the electrocardiogram data may be indicative of a heart condition based on cardiological standards.

In the method, the electrocardiogram data may not be indicative of a heart condition based on cardiological standards.

In the method, the condition may be mortality.

In the method, the condition may be atrial fibrillation.

In another aspect, the present disclosure provides a method including receiving patient electrocardiogram data associated with a patient and an electrocardiogram configuration including a plurality of leads and a time interval from an electrocardiogram device, the patient electrocardiogram data including, for each lead included in the plurality of leads, voltage data associated with at least a portion of the time interval, providing at least a portion of the patient electrocardiogram data to a trained model, the trained model being trained to output a risk score based on input electrocardiogram data associated with the electrocardiogram configuration, receiving a risk score indicative of a likelihood the patient will suffer from a condition within a predetermined period of time from when the patient electrocardiogram data was generated, generating a report based on the risk score, and outputting the report to at least one of a memory or a display for viewing by a medical practitioner or healthcare administrator.

In yet another aspect, the present disclosure provides a system including at least one processor coupled to at least one memory including instructions. The at least one processor executes the instructions to receive electrocardiogram data associated with a patient and an electrocardiogram configuration including a plurality of leads and a time interval, the electrocardiogram data including, for each lead included in the plurality of leads, voltage data associated with at least a portion of the time interval, provide at least a portion of the electrocardiogram data to a trained model, the trained model being trained to output a risk score based on input electrocardiogram data associated with the electrocardiogram configuration, receive a risk score indicative of a likelihood the patient will suffer from a condition within a predetermined period of time from when the electrocardiogram data was generated from the trained model, and output the risk score to at least one of a memory or a display for viewing by a medical practitioner or healthcare administrator.

In still yet another aspect, the present disclosure provides a method including receiving electrocardiogram data associated with a patient and an electrocardiogram configuration including a plurality of leads and a time interval, the electrocardiogram data including, for each lead included in the plurality of leads, voltage data associated with at least a portion of the time interval, receiving demographic data associated with the patient, providing the electrocardiogram data and the demographic data to a trained model, generating information based on the electrocardiogram data, concatenating the information with the demographic data, generating a risk score indicative of a likelihood the patient will suffer from a condition within a predetermined period of time from when the electrocardiogram data was generated based on the information and the demographic data, receiving the risk score from the trained model, and outputting the risk score to at least one of a memory or a display for viewing by a medical practitioner or healthcare administrator.

In the method, the demographic data may include a sex of the patient.

In the method, the demographic data may include an age of the patient.

In the method, the condition may be mortality.

In the method, the condition may be atrial fibrillation.

In the method, the time period may be at least six months. The time period may be at least one year.

In the method, the plurality of leads may include a lead I, a lead V2, a lead V4, a lead V3, a lead V6, a lead II, a lead VI, and a lead V5.

The method may further include generating a report based on the risk score and outputting the report to the display for viewing by a medical practitioner or healthcare administrator.

In one aspect, a method includes: receiving electrocardiogram data associated with a patient and an electrocardiogram configuration including a plurality of leads and a time interval, the electrocardiogram data comprising, for each lead included in the plurality of leads, voltage data associated with at least a portion of the time interval; receiving an age value associated with the patient; receiving a sex value associated with the patient; providing the age value, the sex value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from aortic stenosis within a predetermined period of time from when the electrocardiogram data was generated; and outputting the risk score to at least one of a memory or a display for viewing by a medical practitioner or healthcare administrator.

Providing the age value, the sex value, and at least a portion of the electrocardiogram data to a trained model further comprises: providing the at least a portion of the electrocardiogram data to a convolutional neural network; and providing the age value and the sex value to a boosting model.

The trained model further comprises: training a convolutional neural network on a plurality of patients, wherein the plurality of patients include at least patients having a recorded ECG within a diagnosis threshold and patients having a recorded ECG outside a diagnosis threshold; wherein the diagnosis threshold is compared against the time between the date of diagnosis of aortic stenosis and the date of the recorded ECG; and providing the trained convolutional neural network as the trained model. The trained model further comprises: refining the trained neural network using only the plurality of patients having the recorded ECG outside of the diagnosis threshold, wherein the diagnosis threshold is selected from a number of days.

In another aspect, a method includes: receiving electrocardiogram data associated with a wearable device and a patient and an electrocardiogram configuration including at least one lead and a time interval, the electrocardiogram data comprising voltage data associated with at least a portion of the time interval; receiving an age value associated with the patient; receiving a sex value associated with the patient; providing the age value, the sex value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from aortic stenosis within a predetermined period of time from when the electrocardiogram data was generated; and outputting the risk score to at least one of a memory or a display for viewing by a medical practitioner or healthcare administrator.

In another aspect, a method includes: receiving electrocardiogram data associated with a patient and an electrocardiogram configuration including a plurality of leads and a time interval, the electrocardiogram data comprising, for each lead included in the plurality of leads, voltage data associated with at least a portion of the time interval; predicting an interventricular septal thickness (IVSD) value from the electrocardiogram data; receiving an age value associated with the patient; receiving a sex value associated with the patient; providing the age value, the sex value, and the IVSD value to a trained model, the trained model being trained to generate a risk score based on input information associated with the patient; receiving a risk score indicative of a likelihood the patient will suffer from cardiac amyloidosis within a predetermined period of time from when the electrocardiogram data was generated; and outputting the risk score to at least one of a memory or a display for viewing by a medical practitioner or healthcare administrator.

In another aspect, a method includes: receiving electrocardiogram data associated with a wearable device and a patient and an electrocardiogram configuration including at least one lead and a time interval, the electrocardiogram data comprising voltage data associated with at least a portion of the time interval; predicting an interventricular septal thickness (IVSD) value from the electrocardiogram data; receiving an age value associated with the patient; receiving a sex value associated with the patient; providing the age value, the sex value, and the IVSD value to a trained model, the trained model being trained to generate a risk score based on input information associated with the patient; receiving a risk score indicative of a likelihood the patient will suffer from cardiac amyloidosis within a predetermined period of time from when the electrocardiogram data was generated; and outputting the risk score to at least one of a memory or a display for viewing by a medical practitioner or healthcare administrator.

In another aspect, a method includes: receiving electrocardiogram data associated with a patient and an electrocardiogram configuration including a plurality of leads and a time interval, the electrocardiogram data comprising, for each lead included in the plurality of leads, voltage data associated with at least a portion of the time interval; receiving an age value associated with the patient; receiving a sex value associated with the patient; receiving at least one diagnostic value associated with the patient; receiving a stroke phenotyping value associated with the patient; providing the age value, the sex value, the at least one diagnostic value, the stroke phenotyping value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from a stroke within a predetermined period of time from when the electrocardiogram data was generated; and outputting the risk score to at least one of a memory or a display for viewing by a medical practitioner or healthcare administrator.

Receiving a stroke phenotyping value further comprises: receiving a categorical indication of stroke onset selected from a recent stroke onset, a recent stroke follow-up, and a history of stroke diagnosis. In addition, the at least one diagnostic value is selected from: a diastolic blood pressure, systolic blood pressure, heart rate, heart rhythm, height, weight, race, smoking status, comorbidities, current medications, structured echocardiogram measurements, and structured ECG values associated with the patient.

In another aspect, a method includes receiving electrocardiogram data associated with a wearable device and a patient and an electrocardiogram configuration including at least one lead and a time interval, the electrocardiogram data comprising voltage data associated with at least a portion of the time interval; receiving an age value associated with the patient; receiving a sex value associated with the patient; receiving at least one diagnostic value associated with the patient; receiving a stroke phenotyping value associated with the patient; providing the age value, the sex value, the at least one diagnostic value, the stroke phenotyping value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from a stroke within a predetermined period of time from when the electrocardiogram data was generated; and outputting the risk score to at least one of a memory or a display for viewing by a medical practitioner or healthcare administrator.

In another aspect, a method includes receiving electrocardiogram data associated with a wearable device and a patient and an electrocardiogram configuration including at least one lead and a time interval, the electrocardiogram data comprising voltage data associated with at least a portion of the time interval, the electrocardiogram data further comprising QT interval data; receiving an age value associated with the patient; receiving a sex value associated with the patient; providing the age value, the sex value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from a cardiac event within a predetermined period of time from when the electrocardiogram data was generated; and outputting the risk score to at least one of a memory or a display for viewing by a medical practitioner or healthcare administrator.

The method further includes receiving second electrocardiogram data associated with the patient and a second electrocardiogram configuration including at least one lead and a time interval, the second electrocardiogram data comprising, voltage data associated with at least a portion of the time interval, the second electrocardiogram data further comprising QT interval data, wherein the electrocardiogram data comprises data taken while the patient is not taking at least one drug and/or has not taken the at least one drug within a specified period of time prior to the electrocardiogram data being taken, and wherein the second electrocardiogram data comprises data taken while the patient is taking the at least one drug. The specified period of time is 90 days. The at least one drug is a drug having known or suspected associations with prolongation of a corrected QT interval. The condition is prolongation of a corrected QT interval. The trained model employs an artificial intelligence engine including a deep neural network. The deep neural network uses electrocardiogram data and a gradient-boosted tree using a baseline corrected QT interval with age and sex as additional inputs.

In another aspect, a method includes: receiving electrocardiogram data associated with a wearable device and a patient and an electrocardiogram configuration including at least one lead and a time interval, the electrocardiogram data comprising voltage data associated with at least a portion of the time interval; receiving an age value associated with the patient; receiving a sex value associated with the patient; providing the age value, the sex value, and at least a portion of the electrocardiogram data to a trained model, the trained model being trained to generate a risk score based on input electrocardiogram data associated with the electrocardiogram configuration and supplementary information associated with the patient; receiving a risk score indicative of a likelihood the patient will suffer from Atrial Fibrillation within a predetermined period of time from when the electrocardiogram data was generated; and outputting the risk score to at least one of a memory or a display for viewing by a medical practitioner or healthcare administrator.

In another aspect, a method includes: receiving electrocardiogram data associated with a wearable device and a patient and an electrocardiogram configuration including at least one lead and a time interval, the electrocardiogram data comprising voltage data associated with at least a portion of the time interval; receiving supplementary information associated with the patient; providing at least a portion of the electrocardiogram data to a trained model, the trained model being trained to generate a risk score based on input electrocardiogram data associated with the electrocardiogram configuration and the supplementary information associated with the patient; receiving a risk score indicative of a likelihood the patient will suffer from a cardiac event within a predetermined period of time from when the electrocardiogram data was generated; and outputting the risk score to at least one of a memory or a display for viewing by a medical practitioner or healthcare administrator.

In another aspect, a method includes: receiving electrocardiogram data associated with a wearable device and a patient and an electrocardiogram configuration including at least one lead and a time interval, the electrocardiogram data comprising voltage data associated with at least a portion of the time interval; receiving supplementary information associated with the patient; receiving a transformed model, where in a transformed model is based at least in part on a model trained from electrocardiogram data having two or more leads which has been refined with electrocardiogram data associated with the wearable device and having at least one lead; providing at least a portion of the electrocardiogram data to the transformed model, the transformed model being trained to generate a risk score based on input electrocardiogram data associated with the electrocardiogram configuration and the supplementary information associated with the patient; receiving a risk score indicative of a likelihood the patient will suffer from a cardiac event within a predetermined period of time from when the electrocardiogram data was generated; and outputting the risk score to at least one of a memory or a display for viewing by a medical practitioner or healthcare administrator.

BRIEF DESCRIPTION OF THE SEVERAL VIEWS OF THE DRAWINGS

FIG. 7A is a bar chart of model performance as mean area under the receiver operating characteristic;

FIG. 7B is a bar chart of model performance as mean area under the precision-recall curve;

FIG. 23 is a plot of ECG sensitivity vs. specificity for multiple ECG and QTc models;

DETAILED DESCRIPTION OF THE DISCLOSURE

Figure 1:
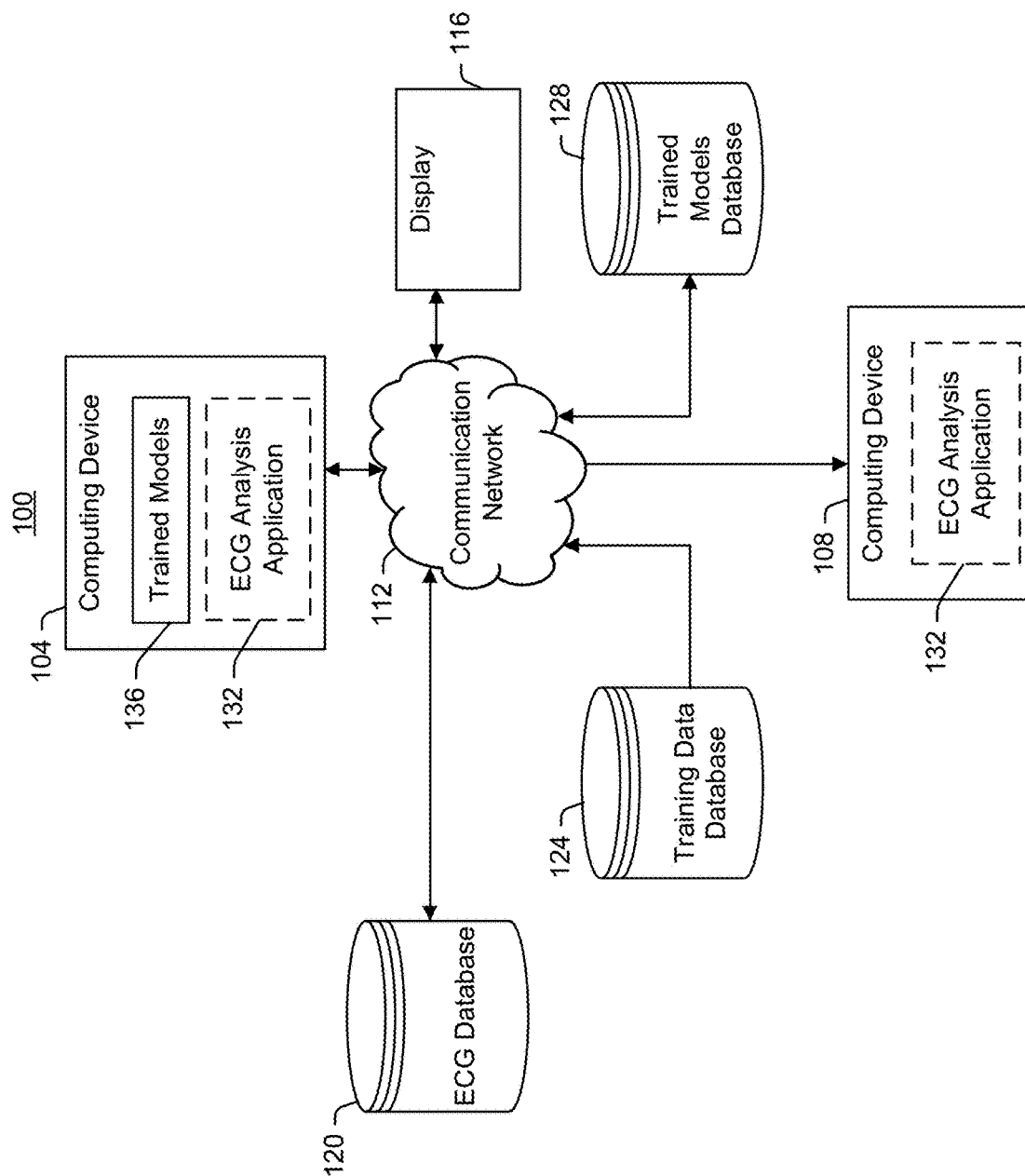
FIG. 1 is an example of a system for automatically predicting an Atrial fibrillation (AF) risk score based on electrocardiogram (ECG) data.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor-based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally, it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Atrial fibrillation (AF) is associated with substantial morbidity, especially when it goes undetected. If new onset AF can be predicted with high accuracy, screening methods could be used to find it early. The present disclosure provides a deep neural network that can predict new onset AF from a resting 12-lead electrocardiogram (ECG). The predicted new onset AF may assist medical practitioners (e.g., a cardiologist) in preventing AF-related adverse outcomes, such as stroke.

A 12-lead electrocardiogram can include a I Lateral lead (also referred to as a I lead), a II Inferior lead (also referred to as a II lead), a III Inferior lead (also referred to as a III lead), an aVR lead, an aVL Lateral lead (also referred to as an aVL lead), an aVF Inferior lead (also referred to as an aVF lead), a V1 Septal lead (also referred to as a V1 lead), a V2 Septal lead (also referred to as a V2 lead), a V3 Anterior lead (also referred to as a V3 lead), a V4 Anterior lead (also referred to as a V4 lead), a V5 Lateral lead (also referred to as a V5 lead), and a V6 Lateral lead (also referred to as a V6 lead).

Atrial Fibrillation (AF) is a cardiac rhythm disorder associated with several important adverse health outcomes including stroke and heart failure. In patients with AF and risk factors for thromboembolism, early anticoagulation has been shown to be effective at preventing strokes. Unfortunately, AF often goes unrecognized and untreated since it is frequently asymptomatic or minimally symptomatic. Thus, systems and methods to screen for and identify undetected AF can assist in preventing strokes.

Population-based screening for AF is challenging for two primary reasons. One, the yearly incidence of AF in the general population is low with reported incidence rates of less than 10 per 1000 person years under the age of 70. Two, AF is often "paroxysmal" (the patient goes in and out of AF for periods of time) with many episodes lasting less than 24 hours. Currently, the most common screening strategy is opportunistic pulse palpation, sometimes in conjunction with a 12-lead electrocardiogram during routine medical visits. This has been shown to be cost-effective in certain populations and is recommended in some guidelines. However, studies of implantable cardiac devices have suggested that this strategy will miss many cases of AF.

A number of continuous monitoring devices are now available to detect paroxysmal and asymptomatic AF. Patch monitors can be worn for up to 14-30 days, implantable loop recorders provide continuous monitoring for as long as 3 years, and wearable monitors, sometimes used in conjunction with mobile devices, can be worn indefinitely. Continuous monitoring devices overcome the problem of paroxysmal AF but must still contend with the overall low incidence of new onset AF and cost and convenience limit their use for widespread population screening.

In the present disclosure, systems and methods to accurately predict cardiac events, including future AF, aortic stenosis (AS), cardiac amyloidosis (CA), and/or stroke (SP) from an ECG, which is a widely utilized and inexpensive test, are described.

FIG. 1 is an example 100 of a system 100 for automatically predicting an AF, AS, CA, and/or SP risk score based on ECG data (e.g., data from a resting 12-lead ECG). In some embodiments, the system 100 can include a computing device 104, a secondary computing device 108, and/or a display 116. In some embodiments, the system 100 can include an ECG database 120, a training data database 124, and/or a trained models database 128. In some embodiments, the computing device 104 can be in communication with the secondary computing device 108, the display 116, the ECG database 120, the training data database 124, and/or the trained models database 128 over a communication network 112. As shown in FIG. 1, the computing device 104 can receive ECG data, such as 12-lead ECG data, and generate an AF, AS, CA, and/or SP risk score based on the ECG data. In some embodiments, the risk score can indicate a predicted risk of a patient developing the cardiac event within a predetermined time period from when the ECG was taken (e.g., three months, six months, one year, five years, ten years, etc.). In some embodiments, the computing device 104 can execute at least a portion of an ECG analysis application 132 to automatically generate the AF, AS, CA, and/or SP risk score.

The system 100 may generate a risk score to provide physicians with a recommendation to consider additional cardiac monitoring for patients who are most likely to experience atrial fibrillation, atrial flutter, or another relevant condition within the predetermined time period. In some examples, the system 100 may be indicated for use in patients aged 40 and older without current AF or prior AF history. In some examples, the system 100 may be indicated for use in patients without pre-existing and/or concurrent documentation of AF or other relevant condition. In some examples, the system 100 may be used by healthcare providers in combination with a patient's medical history and clinical evaluation to inform clinical decision making.

In some embodiments, the ECG data may be indicative or not indicative of a heart condition based on cardiological standards. For example, the ECG data may be indicative of a fast heartbeat. The system 100 may predict a risk score indicative that the patient will suffer from the cardiac condition (e.g., AF) based on ECG data that is not indicative of a given heart condition (e.g., fast heartbeat). In this way, the system may detect patients at risk for one or more conditions even when the ECG data appears "healthy" based on cardiological standards. The system 100 may predict a risk score indicative that the patient will suffer from the condition (e.g., AF) based on ECG data that is indicative of a heart condition (e.g., fast heartbeat). In this way, the system 100 may detect patients at risk for one or more conditions when the ECG data indicates the presence of a different condition.

The ECG analysis application 132 can be included in the secondary computing device 108 that can be included in the system 100 and/or on the computing device 104. The computing device 104 can be in communication with the secondary computing device 108. The computing device 104 and/or the secondary computing device 108 may also be in communication with a display 116 that can be included in the system 100 over the communication network 112. In some embodiments, the computing device 104 and/or the secondary computing device 108 can cause the display 116 to present one or more AF risk scores and/or reports generated by the ECG analysis application 132.

The communication network 112 can facilitate communication between the computing device 104 and the secondary computing device 108. In some embodiments, the communication network 112 can be any suitable communication network or combination of communication networks. For example, the communication network 112 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, the communication network 112 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

The ECG database 120 can include a number of ECGs. In some embodiments, the ECGs can include 12-lead ECGs. Each ECG can include a number of voltage measurements taken at regular intervals (e.g., at a rate of 250 HZ, 500 Hz, 1000 Hz, etc.) over a predetermined time period (e.g., 5 seconds, 10 seconds, 15 seconds, 30 seconds, 60 seconds, etc.) for each lead. In some instances, the number of leads may vary (e.g., from 1-12) and the respective sampling rates and time periods may be different for each lead. In some embodiments, the ECG can include a single lead. In some embodiments, the ECG database 120 can include one or more AF risk scores generated by the ECG analysis application 132.

The training data database 124 can include a number of ECGs and clinical data. In some embodiments, the clinical data can include outcome data, such as whether or not a patient developed AF in a time period following the day that the ECG was taken. Exemplary time periods may include 1 month, 2 months, 3 months, 4 months, 5 months, 6 months, 7 months, 8 months, 9 months, 10 months, 11 months 12 months, 1 year, 2 years, 3 years, 4 years, 5 years, 6 years, 7 years, 8 years, 9 years, or 10 years. The ECGs and clinical data can be used for training a model to generate AF risk scores. In some embodiments, the training data database 124 can include multi-lead ECGs taken over a period of time (such as ten seconds) and corresponding clinical data. In some embodiments, the trained models database 128 can include a number of trained models that can receive raw ECGs and output AF risk scores. In other embodiments, a digital image of a lead for an ECG may be used. In some embodiments, trained models 136 can be stored in the computing device 104.

Figure 2:
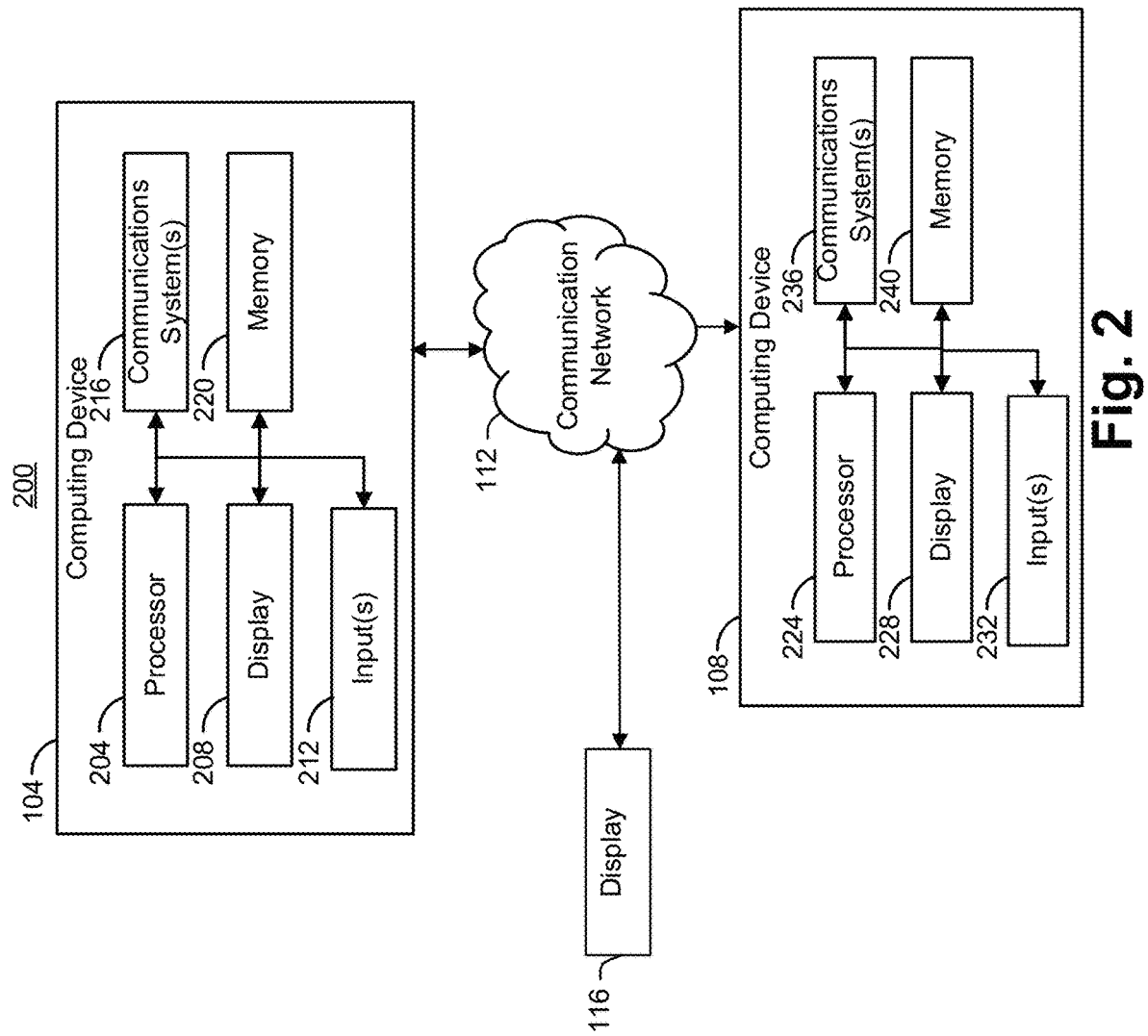
FIG. 2 is an example of hardware that can be used in some embodiments of the system of FIG. 1.

FIG. 2 is an example of hardware that can be used in some embodiments of the system 100. The computing device 104 can include a processor 204, a display 208, one or more input(s) 212, one or more communication system(s) 216, and a memory 220. The processor 204 can be any suitable hardware processor or combination of processors, such as a central processing unit ("CPU"), a graphics processing unit ("GPU"), etc., which can execute a program, which can include the processes described below.

In some embodiments, the display 208 can present a graphical user interface. In some embodiments, the display 208 can be implemented using any suitable display devices, such as a computer monitor, a touchscreen, a television, etc. In some embodiments, the input(s) 212 of the computing device 104 can include indicators, sensors, actuatable buttons, a keyboard, a mouse, a graphical user interface, a touch-screen display, etc.

In some embodiments, the communication system(s) 216 can include any suitable hardware, firmware, and/or software for communicating with the other systems, over any suitable communication networks. For example, the communication system 216 can include one or more transceivers, one or more communication chips and/or chip sets, etc. In a more particular example, communication system 216 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 216 allows the computing device 104 to communicate with the secondary computing device 108.

In some embodiments, the memory 220 can include any suitable storage device or devices that can be used to store instructions, values, etc., that can be used, for example, by the processor 204 to present content using display 208, to communicate with the secondary computing device 108 via communications system(s) 216, etc. The memory 220 can include any suitable volatile memory, non-volatile memory, storage, or any suitable combination thereof. For example, the memory 220 can include RAM, ROM, EEPROM, one or more flash drives, one or more hard disks, one or more solid state drives, one or more optical drives, etc. In some embodiments, the memory 220 can have encoded thereon a computer program for controlling operation of computing device 104 (or secondary computing device 108). In such embodiments, the processor 204 can execute at least a portion of the computer program to present content (e.g., user interfaces, images, graphics, tables, reports, etc.), receive content from the secondary computing device 108, transmit information to the secondary computing device 108, etc.

The secondary computing device 108 can include a processor 224, a display 228, one or more input(s) 232, one or more communication system(s) 236, and a memory 240. The processor 224 can be any suitable hardware processor or combination of processors, such as a central processing unit ("CPU"), a graphics processing unit ("GPU"), etc., which can execute a program, which can include the processes described below.

In some embodiments, the display 228 can present a graphical user interface. In some embodiments, the display 228 can be implemented using any suitable display devices, such as a computer monitor, a touchscreen, a television, etc. In some embodiments, the inputs 232 of the secondary computing device 108 can include indicators, sensors, actuatable buttons, a keyboard, a mouse, a graphical user interface, a touch-screen display, etc.

In some embodiments, the communication system(s) 236 can include any suitable hardware, firmware, and/or software for communicating with the other systems, over any suitable communication networks. For example, the communication system 236 can include one or more transceivers, one or more communication chips and/or chip sets, etc. In a more particular example, communication system(s) 236 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system(s) 236 allows the secondary computing device 108 to communicate with the computing device 104.

In some embodiments, the memory 240 can include any suitable storage device or devices that can be used to store instructions, values, etc., that can be used, for example, by the processor 224 to present content using display 228, to communicate with the computing device 104 via communications system(s) 236, etc. The memory 240 can include any suitable volatile memory, non-volatile memory, storage, or any suitable combination thereof. For example, the memory 240 can include RAM, ROM, EEPROM, one or more flash drives, one or more hard disks, one or more solid state drives, one or more optical drives, etc. In some embodiments, the memory 240 can have encoded thereon a computer program for controlling operation of secondary computing device 108 (or computing device 104). In such embodiments, the processor 224 can execute at least a portion of the computer program to present content (e.g., user interfaces, images, graphics, tables, reports, etc.), receive content from the computing device 104, transmit information to the computing device 104, etc.

The display 116 can be a computer display, a television monitor, a projector, or other suitable displays.

Data Selection and Phenotype Definitions

Figure 3:
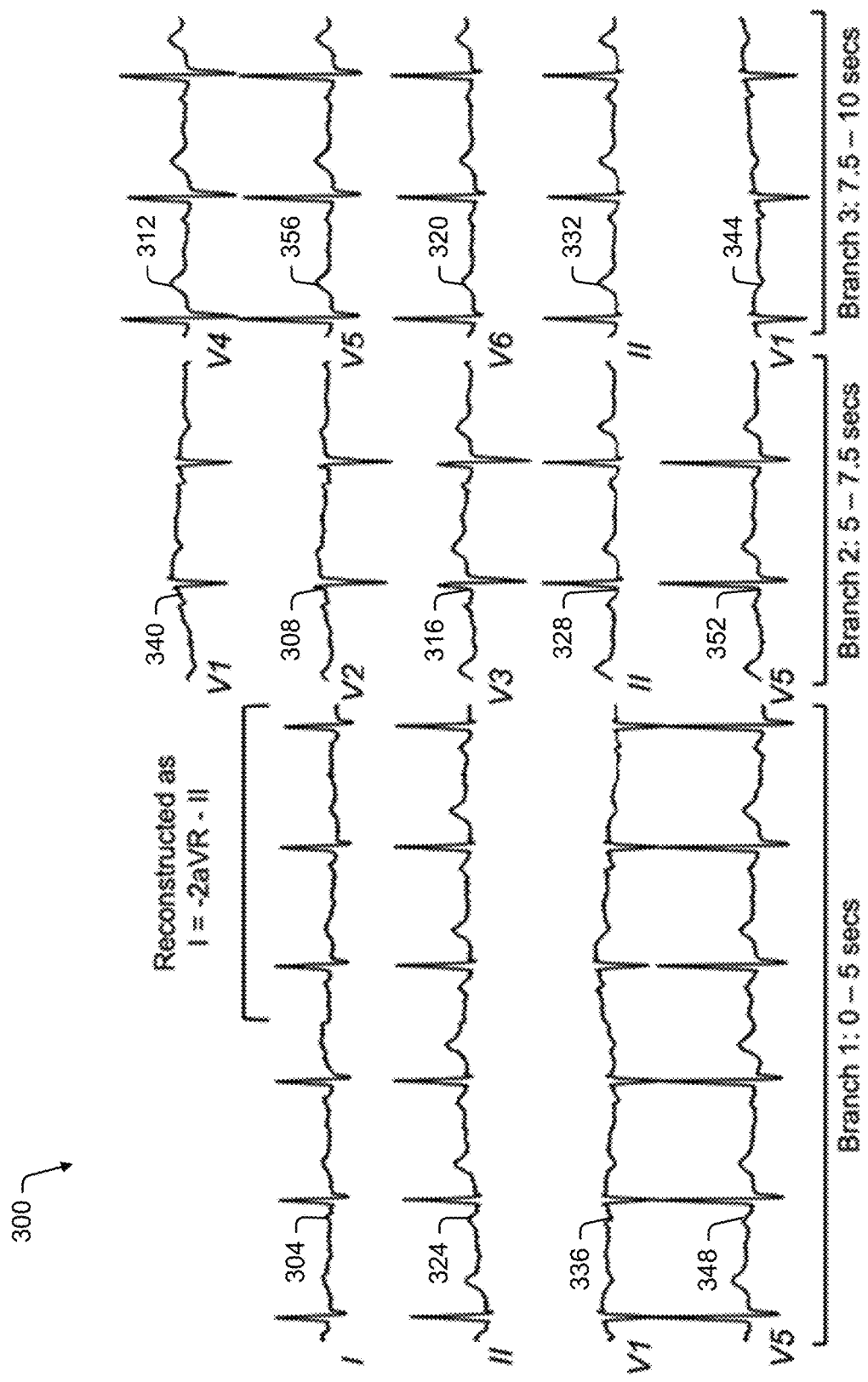
FIG. 3 is an example of raw ECG voltage input data.

FIG. 3 is an example of raw ECG voltage input data 300. The ECG voltage input data includes three distinct, temporally coherent branches after reducing the data representation from 12 leads to 8 independent leads. Specifically, in the example shown in FIG. 3, leads aVL, aVF and III may not need to be used because they are linear combinations of other, retained leads. Adding these leads may negatively impact the performance of a model due to overloading of data from certain leads (for example, creating duplicate information) and lead to overfitting. In some embodiments, these leads may boost model performance when they do not represent duplicate information. Additionally, lead I was computed between the 2.5 and 5 second time interval using Goldberger's equation: $-aVR=(I+II)/2$. In some embodiments, the data can be acquired at 500 Hz. Data not acquired at 500 Hz (such as studies acquired at 250 Hz or 1000 Hz) can be resampled to 500 Hz by linear interpolation or downsampling. In some embodiments, there may be one branch having leads over a full 10 seconds, 20 seconds, or 60 seconds of one or more leads. In other embodiments there may be differing time periods for each branch (e.g., the first branch may include 0-2.5 seconds, the second branch may include 2.5-6 seconds, and the third branch may include 6-10 seconds). In some embodiments, the number of branches may match the number of differing periods (e.g., there may be 10 branches each receiving a subsequent 1 second lead sampled at 100 Hz, there may be 4 branches each receiving a subsequent 2.5 second lead sampled at 500 Hz, etc.). In some embodiments, models may be trained and retained for multiple branch, lead, sampling rate, and/or sampling period structures.

As shown, the raw ECG voltage input data 300 can have a predetermined ECG configuration that defines the leads included in the data and a time interval(s) that each lead is sampled, or measured, over. In some embodiments, for the raw ECG voltage input data 300, the ECG configuration can include lead I having a time interval of 0-5 seconds, lead V2 having a time interval of 5-7.5 seconds, lead V4 having a time interval of 7.5-10 seconds, lead V3 having a time interval of 5-7.5 seconds, lead V6 having a time interval of 7.5-10 seconds, lead II having a time interval of 0-10 seconds, lead VI having a time interval of 0-10 seconds, and lead V5 having a time interval of 0-10 seconds. The entire ECG voltage input data can have a time interval of 0-10 seconds. Thus, some leads may include data for the entire time interval of the ECG voltage input data, and other leads may only include data for a subset of the time interval of the ECG voltage input data.

In some embodiments, the ECG voltage input data 300 can be associated with a time interval (e.g., ten seconds). The ECG voltage input data 300 can include voltage data generated by leads (e.g., lead I, lead V2, lead V4, lead V3, lead V6, lead II, lead VI, and lead V5). In some embodiments, the raw ECG voltage input data 300 can include voltage data generated by the leads over the entire time interval. In some embodiments, the voltage data from certain leads may only be generated over a portion of the time interval (e.g., the first half of the time interval, the third quarter of the time interval, the fourth quarter of the time interval) depending on what ECG data is available for the patient. In some embodiments, a digital image of a raw ECG voltage input data may be used and each lead identified from the digital image and a corresponding voltage (e.g., digital voltage data) may be estimated from analysis of the digital image.

In some embodiments, the ECG voltage input data 300 can include first voltage data 304 associated with the lead I and a first portion of the time interval, second voltage data 308 associated with the lead V2 and a second portion of the time interval, third voltage data 312 associated with the lead V4 and a third portion of the time interval, fourth voltage data 316 associated with the lead V3 and the second portion of the time interval, fifth voltage data 320 associated with the lead V6 and the third portion of the time interval, sixth voltage data 324 associated with the lead II and the first portion of the time interval, seventh voltage data 328 associated with the lead II and the second portion of the time interval, eighth voltage data 332 associated with the lead II and the third portion of the time interval, ninth voltage data 336 associated with the lead VI and the first portion of the time interval, tenth voltage data 340 associated with the lead VI and the second portion of the time interval, eleventh voltage data 344 associated with the lead VI and the third portion of the time interval, twelfth voltage data 348 associated with the lead V5 and the first portion of the time interval, thirteenth voltage data 352 associated with the lead V5 and the second portion of the time interval, and fourteenth voltage data 356 associated with the lead V5 and the third portion of the time interval. In this way, the voltage data associated with the portion(s) of the time interval can be provided to the same channel(s) of a trained model in order to estimate risk scores for the patient.

Figure 4A:
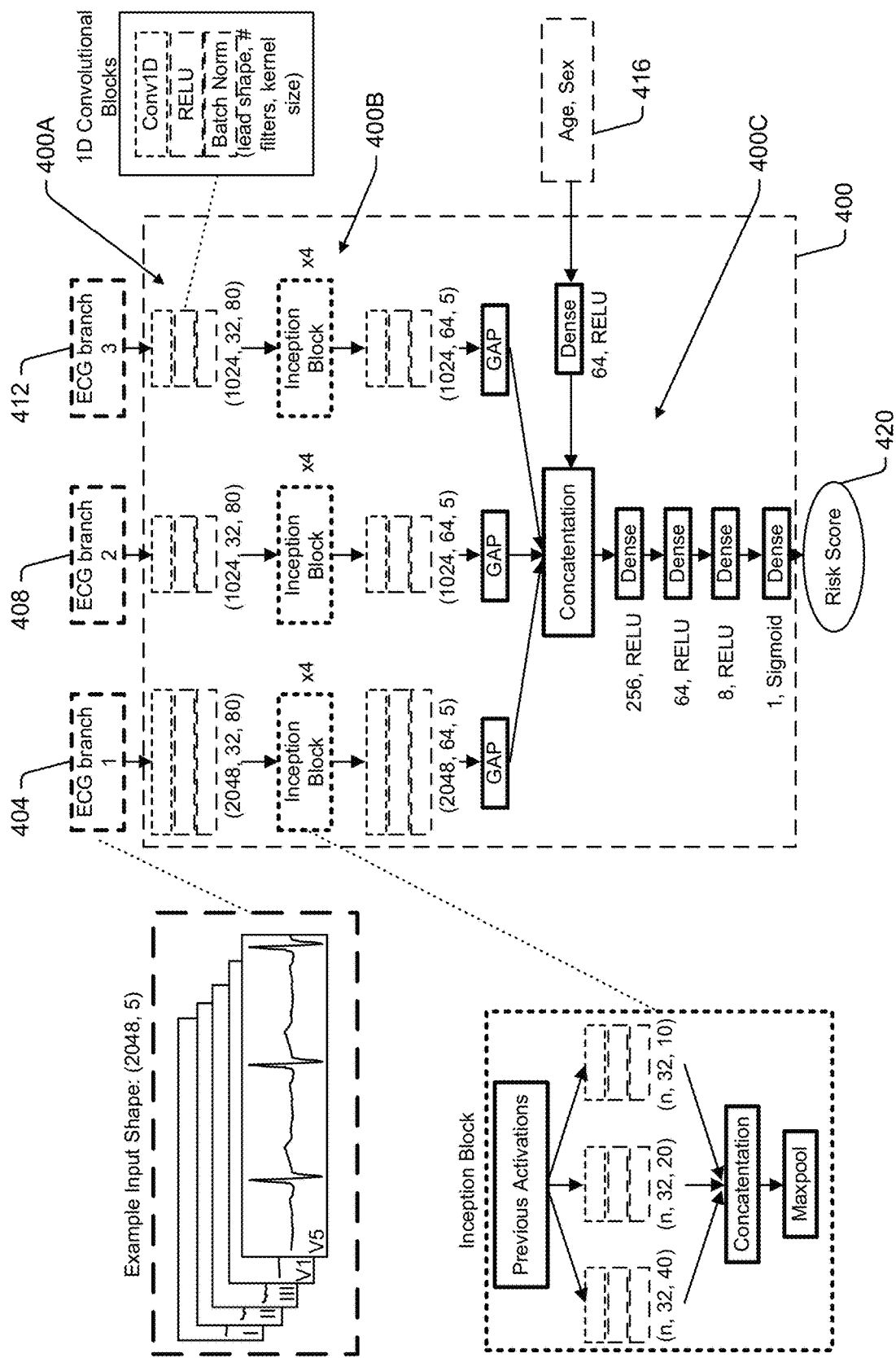
FIG. 4A is an exemplary embodiment of a model.

FIG. 4A is an exemplary embodiment of a model 400. Specifically, an architecture of the model 400 is shown. Artificial intelligence models referenced herein, including model 700 and model 724 discussed further below, may be gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

In some embodiments, the model 400 can be a deep neural network. In some embodiments, the model 400 can receive the input data shown in FIG. 3. The input data structure to the model 400 can include a first branch 404 including leads I, II, V1, and V5, acquired from time (t)=0 (start of data acquisition) to t=5 seconds (e.g., the first voltage data, the sixth voltage data, the ninth voltage data, and the twelfth voltage data); a second branch 408 including leads V1, V2, V3, II, and V5 from t=5 to t=7.5 seconds (e.g., the second voltage data, the fourth voltage data, the seventh voltage data, the tenth voltage data, and the thirteenth voltage data); and a third branch 412 including leads V4, V5, V6, II, and V1 from t=7.5 to t=10 seconds (e.g., the third voltage data, the fifth voltage data, the eighth voltage data, the eleventh voltage data, and the fourteenth voltage data) as shown in FIG. 3. The arrangement of the branches can be designed to account for concurrent morphology changes throughout the standard clinical acquisition due to arrhythmias and/or premature beats. For example, the model 400 may need to synchronize which voltage information or data is acquired at the same point in time in order to understand the data. Because the ECG leads are not all acquired at the same time, the leads may be aligned to demonstrate to the neural network model which data was collected at the same time. It is noted that not every lead needs to have voltage data spanning the entire time interval. This is an advantage of the model 400, as some ECGs do not include data for all leads over the entire time interval. For example, the model 400 can include ten branches, and can be trained to generate a risk score based in response to receiving voltage data spanning subsequent one second periods from ten different leads. As another example, the model 400 can include four branches, and can be trained to generate a risk score based in response to receiving voltage data spanning subsequent 2.5 second periods from four different leads. Certain organizations such as hospitals may use a standardized ECG configuration (e.g., voltage data spanning subsequent one second periods from ten different leads). The model 400 can include an appropriate number of branches and be trained to generate a risk score for the standardized ECG configuration. Thus, the model 400 can be tailored to whatever ECG configuration is used by a given organization.

In some embodiments, the model 400 can include a convolutional component 400A, inception blocks 400B, and a fully connected dense layer component 400C. The convolutional component 400A may start with an input for each branch followed by a convolutional block. Each convolutional block included in the convolutional component 400A can include a 1D convolutional layer, a rectified linear activation (RELU) activation function, and a batchnorm layer, in series. Next, this convolutional block can be followed by four inception blocks 400B in series, where each inception block 400B may include three 1D convolutional blocks concatenated across the channel axis with decreasing filter window sizes. Each of the four inception blocks 400B can be connected to a 1D max pooling layer, where they are connected to another single 1D convolutional block and a final global averaging pool layer. The outputs for all three branches can be concatenated and fully connected to the dense layer component 400C. The dense layer component 400C can include four dense layers of 256, 64, 8 and 1 unit(s) with a sigmoid function as the final layer. All layers in the architecture can enforce kernel constraints and may not include bias terms. In some embodiments, an AdaGrad optimizer can be used with a learning rate of $1e^{-4}$ 45, a linear learning rate decay of 1/10 prior to early stopping for efficient model convergence, and batch size of 2048. While AdaGrad is presented, other examples of algorithms which adaptively update the learning rate of a model, such as through stochastic gradient descent iterative methods include RMSProp, Adam, and backpropagation learning such as the momentum method. In some embodiments, the model 400 can be implemented using one or more machine learning libraries, such as Keras, PyTorch, TernsorFlow, Theano, MXNet, scikit-learn, CUDA, Kubeflow, or MLflow. For example, the model 700 may be implemented using Keras with a TensorFlow backend in python and default training parameters were used except where specified. In some embodiments, AdaGrad optimizer can be used with a learning rate of $1e^{-4\ 45}$, a linear learning rate decay of 1/10 prior to early stopping for efficient model convergence at patience of three epochs, and batch size of 2048. In some embodiments, differing model frameworks, hypertuning parameters, and/or programming languages may be implemented. The patience for early stopping was set to 9 epochs. In some embodiments, the model 400 can be trained using NVIDIA DGX1 and DGX2 machines with eight and sixteen V100 GPUs and 32 GB of RAM per GPU, respectively.

In some embodiments, the model 400 can additionally receive electronic health record (EHR) data points such as demographic data 416, which can include age and sex/gender as input features to the network, where sex can be encoded into binary values for both male and female, and age can be cast as a continuous numerical value corresponding to the date of acquisition for each 12-lead resting state ECG. In some embodiments, other representations may be used, such as an age grouping 0-9 years, 10-19 years, 20-29 years, or other grouping sizes. In some embodiments, other demographic data such as race, smoking status, height, and/or weight may be included. In some embodiments, the EHR data points can include laboratory values, echo measurements, ICD codes, and/or care gaps. The EHR data points (e.g., demographic data, laboratory values, etc.) can be provided to the model 400 at a common location.

The EHR data points (e.g., age and sex) can be fed into a 64-unit hidden layer and concatenated with the other branches. In some instances, these EHR features can be extracted directly from the standard 12-lead ECG report. In some embodiments, the model 400 can generate ECG information based on voltage data from the first branch 404, the second branch 408, and the third branch 412. In some embodiments, the model 400 can generate demographic information based on the demographic data 416. In some embodiments, the demographic information can be generated by inputting age and sex were input into a 64-unit hidden layer. The demographic information can be concatenated with the ECG information, and the model 400 can generate a risk score 420 based on the demographic information and the ECG information. Concatenating the ECG information with the separately generated demographic information can allow the model 400 to individually disseminate the voltage data from the first branch 404, the second branch 408, and the third branch 412, as well as the demographic data 416, which may improve performance over other models that provide the voltage data and the demographic data 416 to the model at the same channel.

In some embodiments, the model 400 can be included in the trained models 136. In some embodiments, the risk score 420 can be indicative of a likelihood the patient will suffer from one or more conditions within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. For example, in some embodiments, the model 400 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years.

Figure 4B:
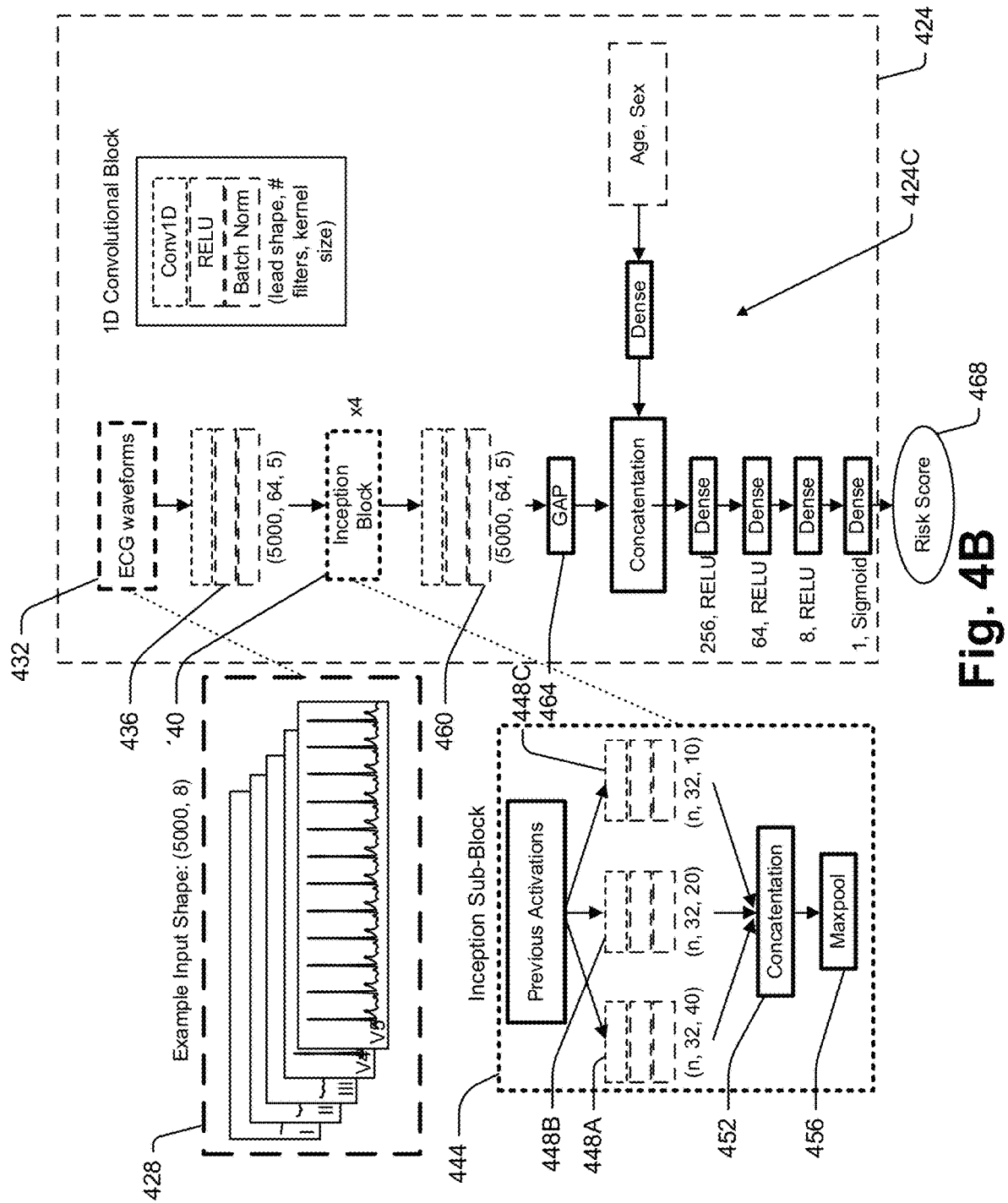
FIG. 4B is another exemplary embodiment of a model.

FIG. 4B is another exemplary embodiment of a model 424. Specifically, another architecture of the model 400 in FIG. 4A is shown. In some embodiments, the model 424 in FIG. 4B can receive ECG voltage data generated over a single time interval.

In some embodiments, the model 424 can be a deep neural network. In some embodiments, such as is shown in FIG. 4B, the model 424 can include a single branch 432 that can receive ECG voltage input data 428 generated over a single time interval (e.g., ten seconds). As shown, the model 424 can receive ECG voltage input data 428 generated over a time interval of ten seconds using eight leads. In some embodiments, the ECG voltage input data 428 can include five thousand data points collected over a period of 10 seconds and 8 leads including leads I, II, V1, V2, V3, V4, V5, and V6. The number of data points can vary based on the sampling rate used to sample the leads (e.g., a sampling rate of five hundred Hz will result in five thousand data points over a time period of ten seconds). The ECG voltage input data 428 can be transformed into ECG waveforms.

As described above, in some embodiments, the ECG voltage input data 428 can be "complete" and contain voltage data from each lead (e.g., lead I, lead V2, lead V4, lead V3, lead V6, lead II, lead VI, and lead V5) generated over the entire time interval. Thus, in some embodiments, the predetermined ECG configuration can include lead I, lead V2, lead V4, lead V3, lead V6, lead II, lead VI, and lead V5 having time intervals of 0-10 seconds. The model 424 can be trained using training data having the predetermined ECG configuration including lead I, lead V2, lead V4, lead V3, lead V6, lead II, lead VI, and lead V5 having time intervals of 0-10 seconds. When all leads share the same time intervals, the model can receive the ECG voltage input data 428 at a single input branch 432. Otherwise, the model can include a branch for each unique time interval may be used as described above in conjunction with FIG. 4A.

The ECG waveform data for each ECG lead may be provided to a 1D convolutional block 436 where the layer definition parameters (n, f, s) refer, respectively, to the number of data points input presented to the block, the number of filters used, and the filter size/window. In some embodiments, the number of data points input presented to the block can be five thousand, the number of filters used can be thirty-two, and the filter size/window can be eighty. The 1D convolutional block 436 can generate and output a downsampled version of the inputted ECG waveform data to the inception block. In some embodiments, the first 1D convolutional block 436 can have a stride value of two.

The model 424 can include an inception block 440. In some embodiments, the inception block 440 can include a number of sub-blocks. Each sub-block 444 can include a number of convolutional blocks. For example, each sub-block 444 can include a first convolutional block 448A, a second convolutional block 448B, and a third convolutional block 448C. In the example shown in FIG. 4B, the inception block 440 can include four sub-blocks in series, such that the output of each sub-block is the input to the next sub-block. Each inception sub-block can generate and output a downsampled set of time-series information. Each sub-block can be configured with filters and filter windows as shown in the inception block 440 with associated layer definition parameters.

In some embodiments, the first convolutional block 448A, the second convolutional block 448B, and the third convolutional block 448C can be 1D convolutional blocks. Results from each of the convolutional blocks 444A-C can be concatenated 452 by combining the results (e.g., arrays), and inputting the concatenated results to a downsampling layer, such as a MaxPool layer 456 included in the sub-block 444. The MaxPool layer 456 can extract positive values for each moving 1D convolutional filter window, and allows for another form of regularization, model generalization, and prevent overfitting. After completion of all four inception block processes, the output is passed to a final convolutional block 460 and then a global average pooling (GAP) layer 464. The purpose of the GAP layer 464 is to average the final downsampled ECG features from all eight independent ECG leads into a single downsampled array. The output of the GAP layer 464 can be passed into the series of dense layer components 424C as in conjunction with FIG. 4A (e.g., at the dense layer component 400C). Furthermore, optimization parameters can also be set for all layers. For example, all layer parameters can enforce a kernel constraint parameter (max_norm=3), to prevent overfitting the model. The first convolutional block 436 and the final convolutional block 460 can utilize a stride parameter of n=1, whereas each inception block 440 can utilize a stride parameter of n=2. The stride parameters determine the movement of every convolutional layer across the ECG time series and can have an impact on model performance. In some embodiments, the model 424 can also concatenate supplementary data such as age and sex as described above in conjunction with FIG. 4A, and the model 424 can utilize the same dense layer component architecture as the model 400. The model 424 can output a risk score 468 based on the demographic information and the ECG information. Specifically, the dense layer components 424C can output the risk score 468. In some embodiments, the risk score 420 can be indicative of a likelihood the patient will suffer from a condition within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. In some embodiments, for example, the model 400 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years.

Figure 5A:
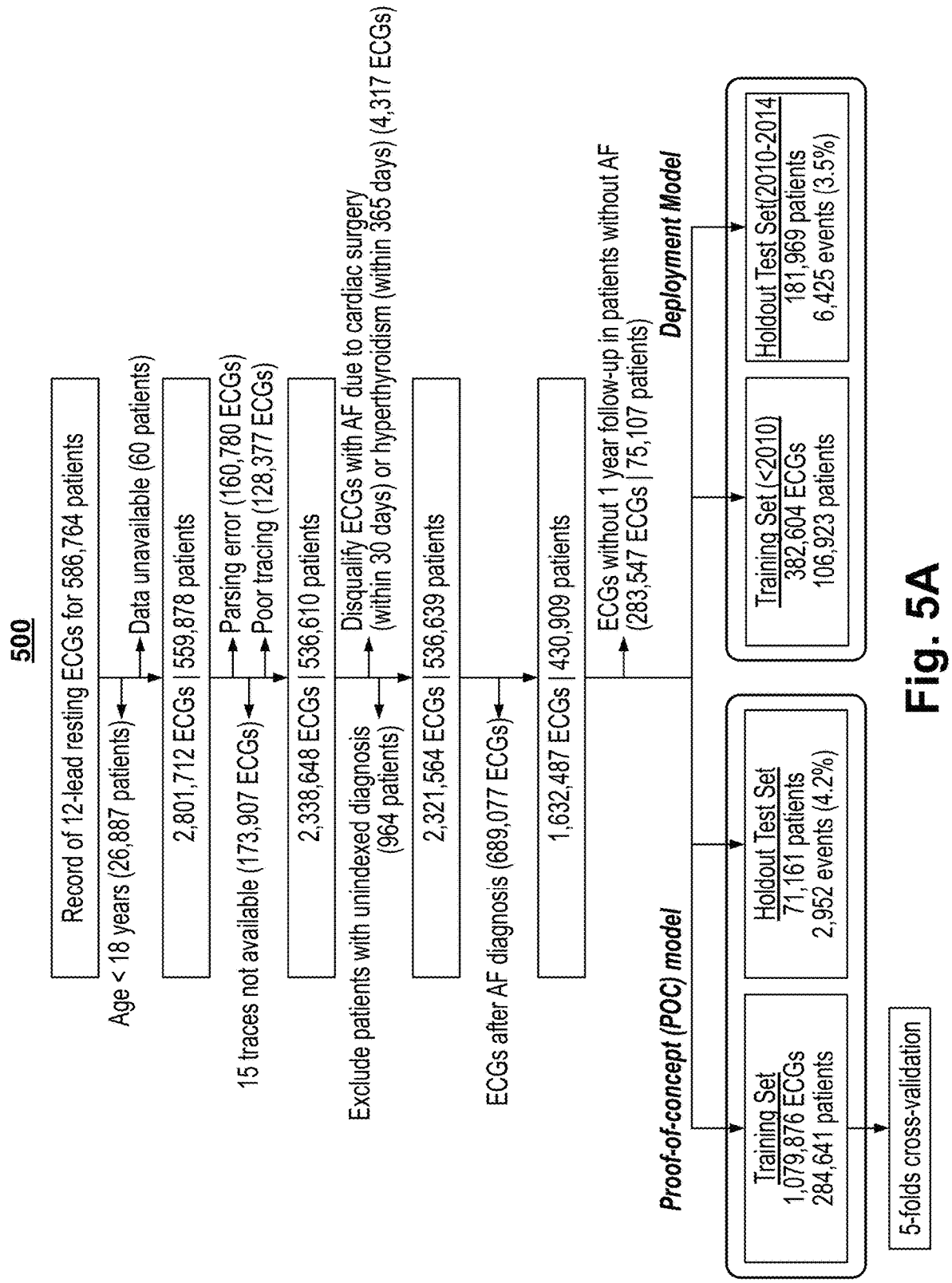
FIG. 5A is an exemplary flow of training and testing the model of FIG. 4A.
Figure 5B:
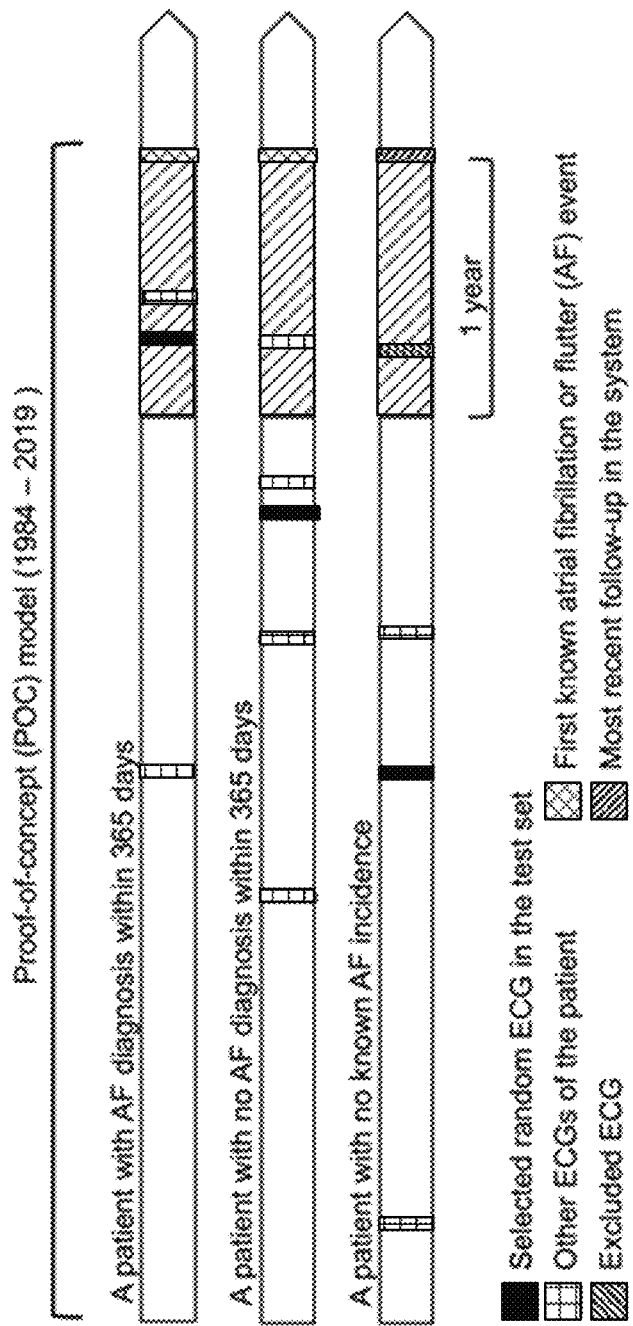
FIG. 5B shows a timeline for ECG selection in accordance with FIG. 5A.

FIG. 5A is an exemplary flow 500 of training and testing the model 400 in FIG. 4A, although it will be appreciated that other training and/or testing procedures may be implemented. 2.8 million standard 12-lead ECG traces were extracted from a medical database. All ECGs with known time-to-event or minimum 1-year follow-up were used during model training and a single random ECG was selected for each patient in the holdout set for model evaluation, with results denoted as 'M0' in FIG. 5B. FIG. 5B shows a timeline for ECG selection in accordance with FIG. 5A. The traces were acquired between 1984 and June 2019. Additional retraining was performed only the resting 12-lead ECGs: 1) acquired in patients ≥18 years of age, 2) with complete voltage-time traces of 2.5 seconds for 12 leads and 10 seconds for 3 leads (V1, II, V5), and 3) with no significant artifacts. This amounted to 1.6 million ECGs from 431 k patients. The median (interquartile range) follow-up available after each ECG was 4.1 (1.5-8.5) years. Each ECG was defined as normal or abnormal as follows: 1) normal ECGs were defined as those with pattern labels of "normal ECG" or "within normal limits" and no other abnormalities identified; 2) all other ECGs were considered abnormal. Note that a normal ECG does not imply that the patient was free of heart disease or other medical diagnoses. All the ECG voltage-time traces were preprocessed to ensure that waveforms were centered around the zero baseline, while preserving variance and magnitude features.

All studies from patients with pre-existing or concurrent documentation of AF were excluded, it being understood that this process can be adapted to patients with pre-existing or concurrent documentation of one or more other disease types if the model 700 is being used to evaluate ECG data with respect to those disease types in addition to or instead of AF. Thus, it should be understood that the discussion below can be adapted to those other disease states by substituting those disease states for the "AF" references and/or by defining features of those disease states. The AF phenotype was defined as a clinically reported finding of atrial fibrillation or atrial flutter from a 12-lead ECG or a diagnosis of atrial fibrillation or atrial flutter applied to two or more inpatient or outpatient encounters or on the patient problem list from the institutional electronic health record (EHR) over a 24-year time period. Any new diagnoses occurring within 30 days following cardiac surgery or within one year of a diagnosis of hyperthyroidism were excluded. Details on the applicable diagnostic codes and blinded chart review validation of the AF phenotype are provided in Table 1 below. Atrial flutter was grouped with atrial fibrillation because the clinical consequences of the two rhythms are similar, including the risk of embolization and stroke, and because the two rhythms often coexist. In some embodiments, differing data may be selected for training, validation, and/or test sets of the model.

Table 1 shows performance measures for the blinded chart review of the AF phenotype definition. Diagnostic codes (ICD 9, 10 and EDG) and corresponding description may be used in defining AF phenotype.

TABLE 1

| Blinded chart review validation (AF phenotype) | |
| --- | --- |
| Positive Predictive Value | 94.4% |
| Negative Predictive Value | 100% |
| Sensitivity | 100% |
| Specificity | 91.6% |
| True Positive | 117 |
| True Negative | 76 |
| False Positive | 7 |
| False Negative | 0 |

AF was considered "new onset" if it occurred at least one day after the baseline ECG at which time the patient had no history of current or prior AF. EHR data were used to identify the most recent qualifying encounter date for censorship. Qualifying encounters were restricted to ECG, echocardiography, outpatient visit with internal medicine, family medicine or cardiology, any inpatient encounter, or any surgical procedure.

For all experiments, data were divided into training, internal validation, and test sets. The composition of the training and test sets varied by experiment, as described below; however, the internal validation set in all cases was defined as a 20% subset of the training data to track validation area under the receiver operating characteristic curve (AUROC) during training to avoid overfitting by early stopping. The patience for early stopping was set to 9 and the learning rate was set to decay after 3 epochs when there was no improvement in the AUROC of the internal validation set during training.

The models were evaluated using the AUROC, which is a robust metric of model performance that represents the ability to discriminate between two classes, although it will be appreciated that other metrics may be used in order to evaluate model performance. Higher AUROC suggests higher performance (with perfect discrimination represented by an AUROC of 1 and an AUROC of 0.5 being equivalent to a random guess). Multiple AUROCs were compared by bootstrapping 1000 instances (using random and variable sampling with replacement). Differences between models were considered statistically significant if the absolute difference in the 95% CI was greater than zero. The models were also evaluated using area under the precision recall curve (AUPRC) as average precision score by computing weighted average of precisions achieved at each threshold by the increase in recall.

Study Design

Two separate modeling experiments were performed as illustrated in FIG. 5A.

DNN Prediction Proof-of-Concept (POC)

Using all ECGs from a 15-year period, patients were randomly split into a training set (D0 dataset: 80% of qualifying studies) and a holdout test set (20%) without overlap of patients between sets. Two versions of the model architecture were compared (as described above): one with ECG voltage versus time traces alone as inputs, and a second with ECG traces as well as age and sex. Results derived from the holdout test set were denoted as model 'M0'. For comparison, a boosted decision-tree based model using only age and sex as inputs and the published CHARGE-AF 5-year risk prediction model were implemented in patients with all necessary data available (requiring age, race, height, weight, systolic and diastolic blood pressure, smoking status, use of antihypertensive medications, and presence or absence of diabetes, heart failure, and history of myocardial infarction. In some embodiments, race and/or smoking status may not be used. To further evaluate model generalizability, 5-fold cross validation (CV) was performed within the D0 dataset to derive models M1-M5. There was no overlap of patients between the train and test sets in each fold. All ECGs with known time-to-event or follow-up were used during model training and a single random ECG for a patient was chosen from the test set in all models (M0 and M1-M5) so as not to overweight patients with multiple ECGs.

To demonstrate that there was no bias from selecting a single random ECG from each patient in the POC model, the performance of the M0 model was determined to be stable without bias across 100 random iterations of selections with mean and standard deviation of AUROCs and AUPRCs of 0.834±0.002 and 0.209±0.004, respectively, for the model with input of ECG traces only; and, 0.845±0.002 and 0.220±0.004 for the model with input of ECG traces with age and sex.

Kaplan-Meier incidence-free survival analysis was also performed based on the POC model with the available follow-up data stratified by the DNN model prediction, using an optimal operating point to stratify the population into low and high-risk groups. The optimal operating point for the M0 model was defined as the point on the ROC curve on the highest iso-performance line (equal cost to misclassification of positives and negatives) in the internal validation set, and that threshold was applied to the test set. The data were censored based on the most recent encounter or development of AF. A Cox Proportional Hazard model regressing time to incidence of AF on the DNN model-predicted classification of low-risk and high-risk in the subset of normal ECGs and the subset of abnormal ECGs was fit. The hazard ratios with 95% confidence intervals (CI) were reported for all data and the normal and abnormal subsets for models M0 and M1-M5 (mean value with lower and upper bounds of 95% CI). The lifelines package (version: 0.24.1) in Python was used for survival analysis.

Simulated Deployment Model

To simulate a real-world deployment scenario—using the model to predict incident AF and potentially prevent AF-related strokes—a second modeling approach was used. All ECGs from a 15-year period were used as a training set. All ECGs from a five-year period were used as a test set.

To account for potential variability in the clinical implementation of such a model (matching the performance to the scope of available resources and desired screening characteristics), performance was evaluated across a range of operating points. An operating point can be the threshold of the model risk that was used to classify high or low risk for developing incident AF. For example, an operating point of 0.7 would indicate that model risk scores equal to and above 0.7 are considered high risk, and risk scores below 0.7 are low risk. Thus, overall model performance can be measured using AUROC and AUPRC scores that aggregate multiple operating point performances into a single metric. These points were defined based on maxima of the Fb score (for b=0.15, 0.5, 1, and 2) within the internal validation set. Fb scores are functions of precision and recall. A b value of 1 is the harmonic mean of precision and recall (e.g. sensitivity), a value of 2 emphasizes recall, and values of 0.15 and 0.5 attenuate the influence of recall correspondingly. Given the substantial variation in incidence of AF with age, the operating point was varied by age. The ECG with the highest risk for each patient acquired between the five-year period mentioned above was selected as the test set.

Figure 6A:
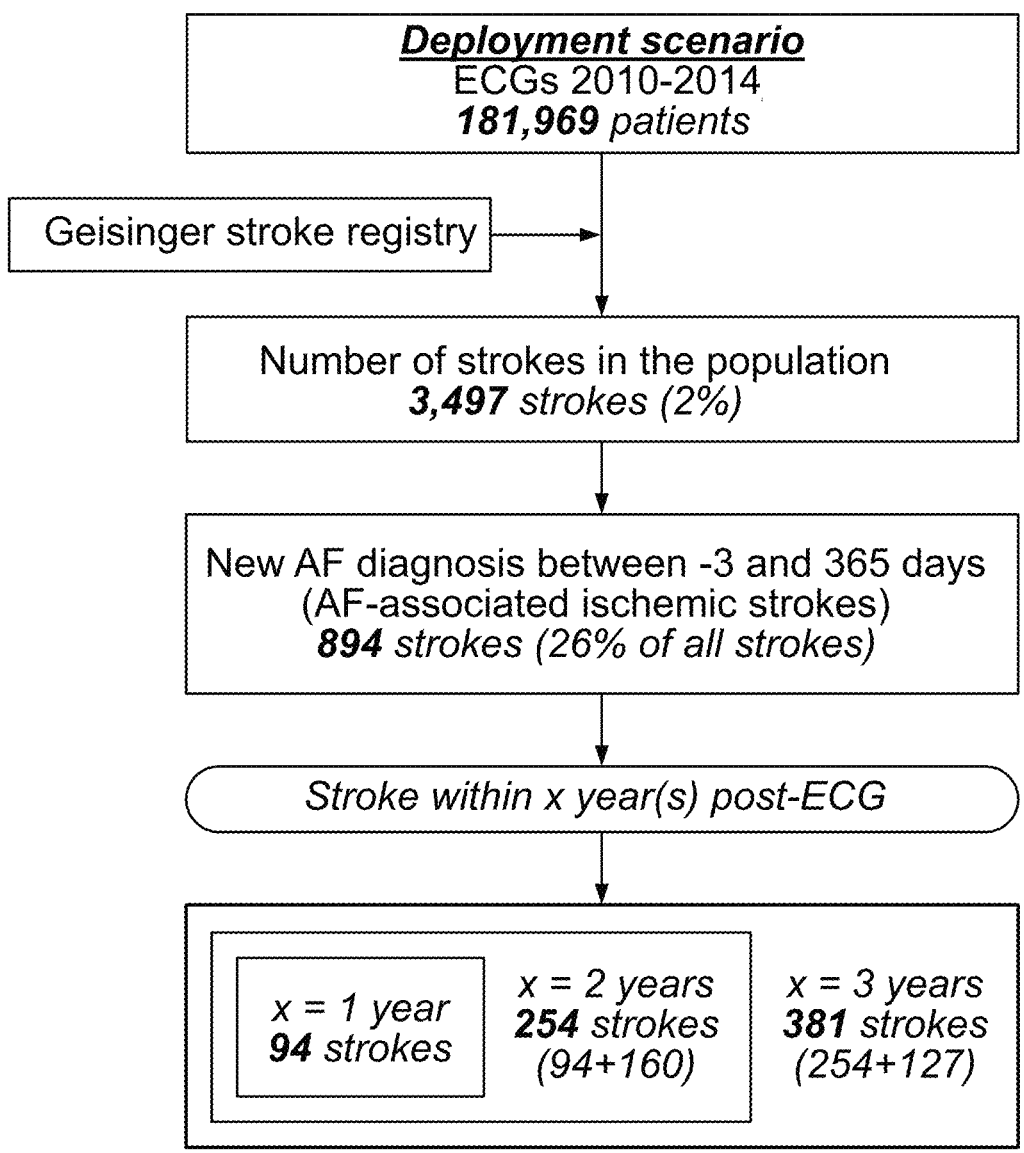
FIG. 6A is a flow including steps employed in identification of potentially preventable AF-related strokes among all recorded ischemic strokes in a stroke registry.
Figure 6B:
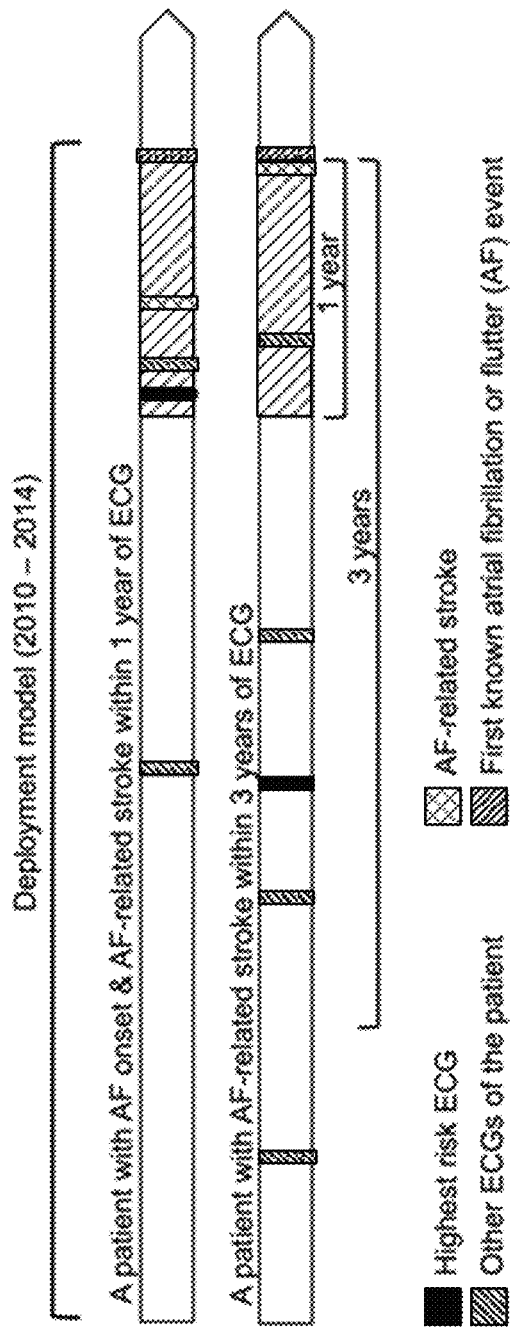
FIG. 6B is a timeline for ECG selection in accordance with FIG. 6A.

To link deployment model predictions with potentially preventable stroke events, an internal registry of patients diagnosed with acute ischemic stroke was used. Through an eight-year period, representing the time interval included in this analysis, there were 6,569 patients in this registry who were treated for ischemic stroke. This registry was used to identify patients within the deployment model test set with an ischemic stroke subsequent to the test set ECG. A stroke was considered potentially preventable if the following criteria were met: 1) the patient had at least one ECG prior to the stroke that predicted a high risk of AF for the given operating point, 2) new onset AF was identified between 3 days prior to the stroke or up to 365 days after the stroke, and 3) the patient was not on anticoagulation at the time of the stroke. To allow for adequate follow-up, strokes that occurred within 3 years of the ECG were included as shown in FIG. 6A. FIG. 6A is a flow 600 including steps employed in identification of potentially preventable AF-related strokes among all recorded ischemic strokes in the stroke registry. FIG. 6B shows a timeline for ECG selection in accordance with FIG. 6A.

Results

Figure 7D:
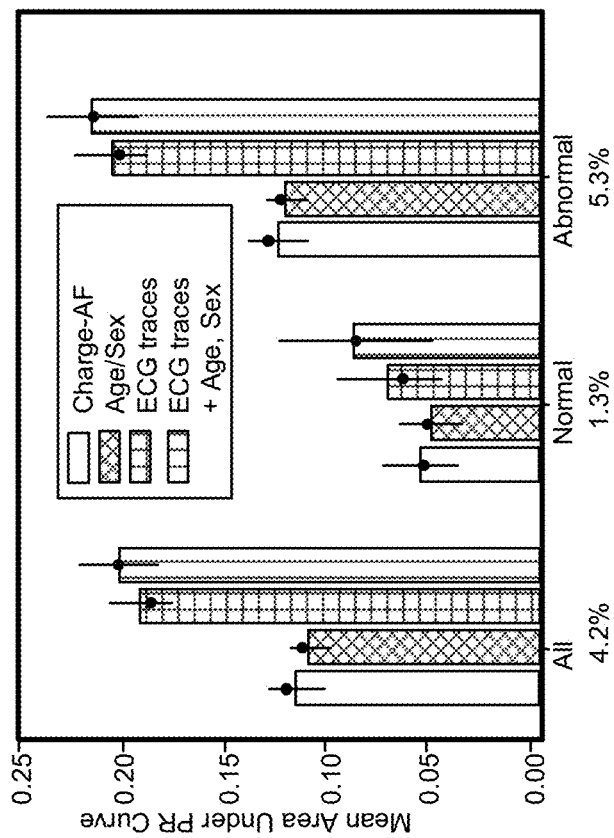
FIG. 7D is a bar graph of precision-recall curves for the population with sufficient data for computation of the CHARGE-AF score.
Figure 7C:
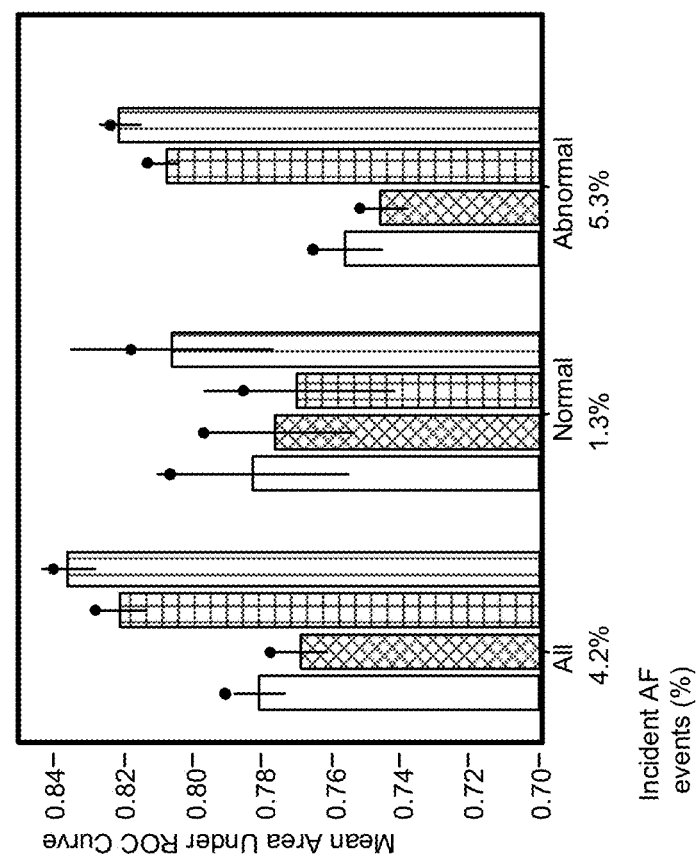
FIG. 7C is a bar graph of model performance as area under the receiver operating characteristic.

The AUROC and AUPRC of the POC DNN models for the prediction of new onset AF within 1 year in the holdout set (M0) were 0.83, 95% CI [0.83, 0.84] and 0.21 [0.20, 0.22], respectively, for DNN-ECG and 0.85 [0.84, 0.85] and 0.22 [0.21, 0.24], respectively, for DNN-ECG-AS. FIG. 7A is a bar chart of model performance as mean area under the receiver operating characteristic. FIG. 7B is a bar chart of model performance as mean area under the precision-recall curve. The bars represent the mean performance across the 5-fold cross-validation with error bars showing standard deviations. The circle represents the M0 model performance on the holdout set. The three bars represent model performance for (i) Extreme gradient boosting (XGB) model with age and sex as inputs; (ii) DNN model with ECG voltage-time traces as input and (iii) DNN model with ECG voltage-time traces, age and sex as inputs. Within the holdout set there was sufficient data to calculate CHARGE-AF scores for 65% of the patients. Within this subset, the DNN-ECG-AS showed superior performance (AUROC=0.84, [0.83, 0.85]; AUPRC=0.20 [0.19, 0.22] compared to the CHARGE-AF score (AUROC=0.79 [0.78, 0.80]; AUPRC=0.12 [0.11, 0.13]. FIG. 7C is a bar graph of model performance (proof-of-concept model) as area under the receiver operating characteristic, and FIG. 7D is a bar graph of precision-recall curves for the population with sufficient data for computation of the CHARGE-AF score. The bars represent the mean performance across the 5-fold cross-validation with error bars showing 95% confidence intervals. The circle represents the M0 model performance on the holdout set. The three bars represent model performance for (i) Extreme gradient boosting (XGB) model with age and sex as inputs; (ii) DNN model with digital ECG traces as input and (iii) DNN model with digital ECG traces, age and sex as inputs.

This performance represents a significant improvement compared to the XGBoost model using only age and sex (AUROC=0.78; AUPRC=0.13; p<0.05 for difference in 95% CI by bootstrapping for both DNN models). Similarly, within the 65% of patients in the holdout test set for whom the CHARGE-AF score could be computed (AUROC=0.78; AUPRC=0.13), the DNN showed superior performance as well (AUROC=0.79; AUPRC=0.12; see FIG. 7B).

Figure 7E:
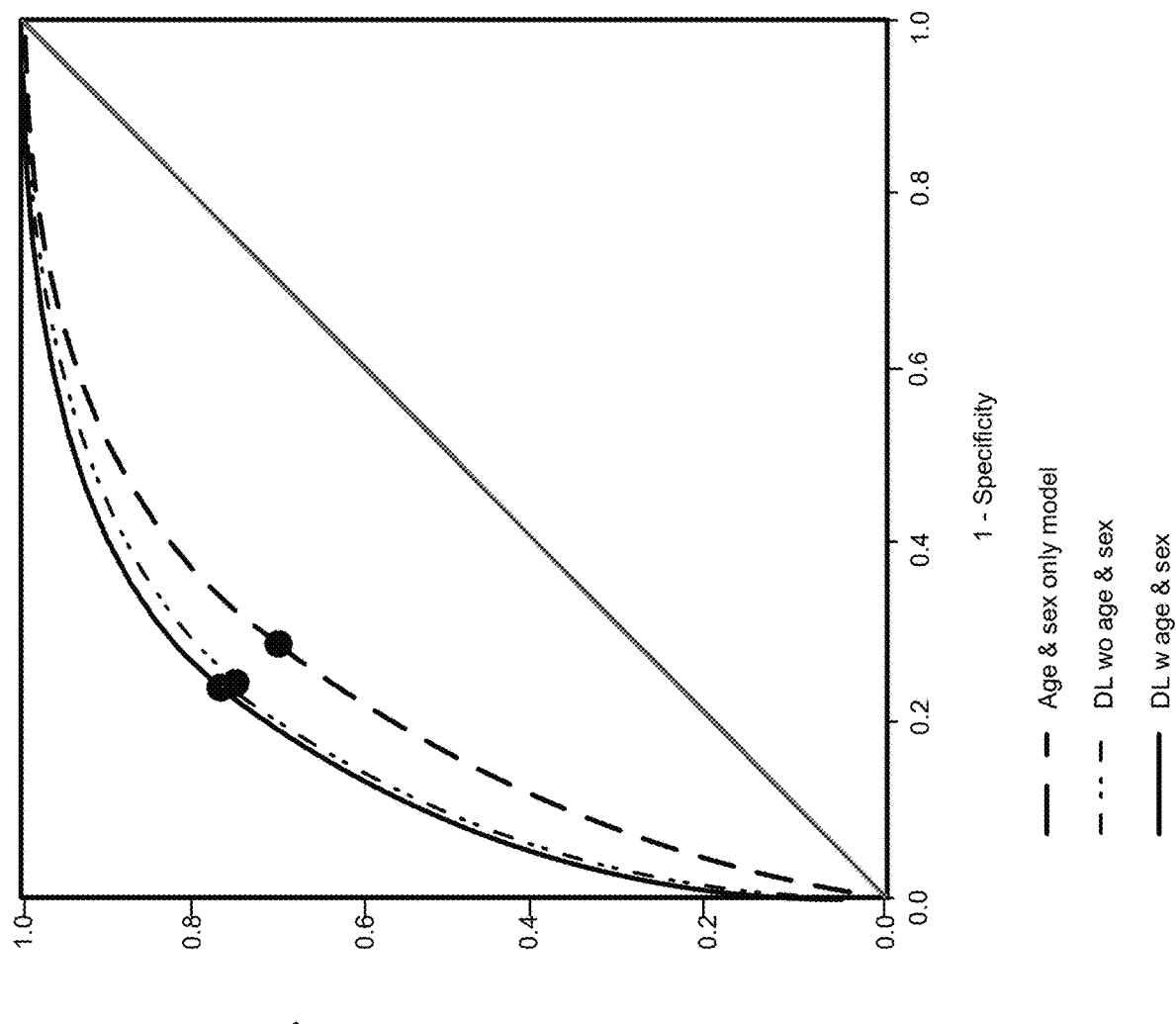
FIG. 7E is a graph of ROC curves with operating points marked for the three models.
Figure 7F:
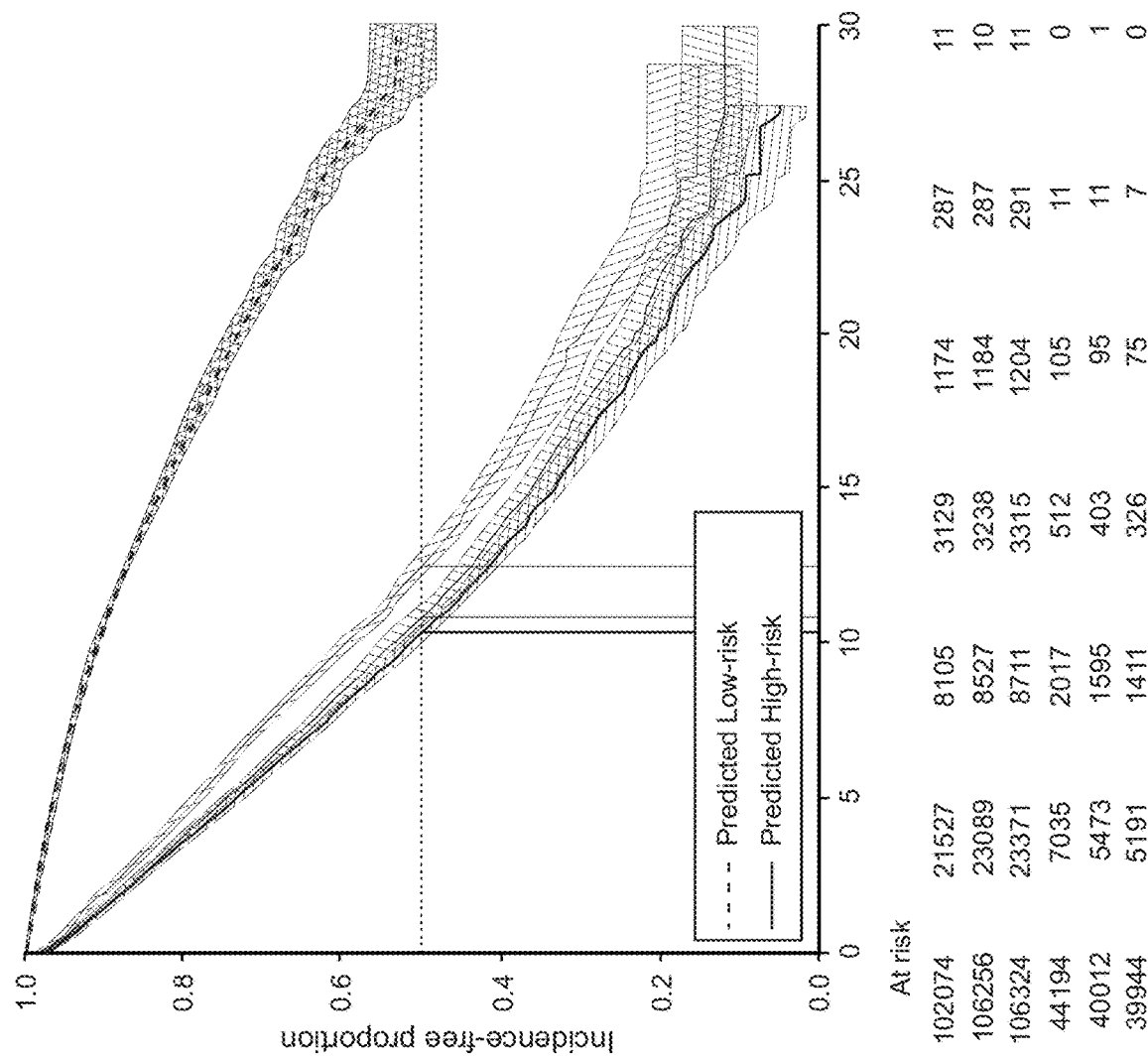
FIG. 7F is a graph of incidence-free survival curves for the high- and low-risk groups for the operating point shown in A for a follow-up of 30 years.
Figure 7G:
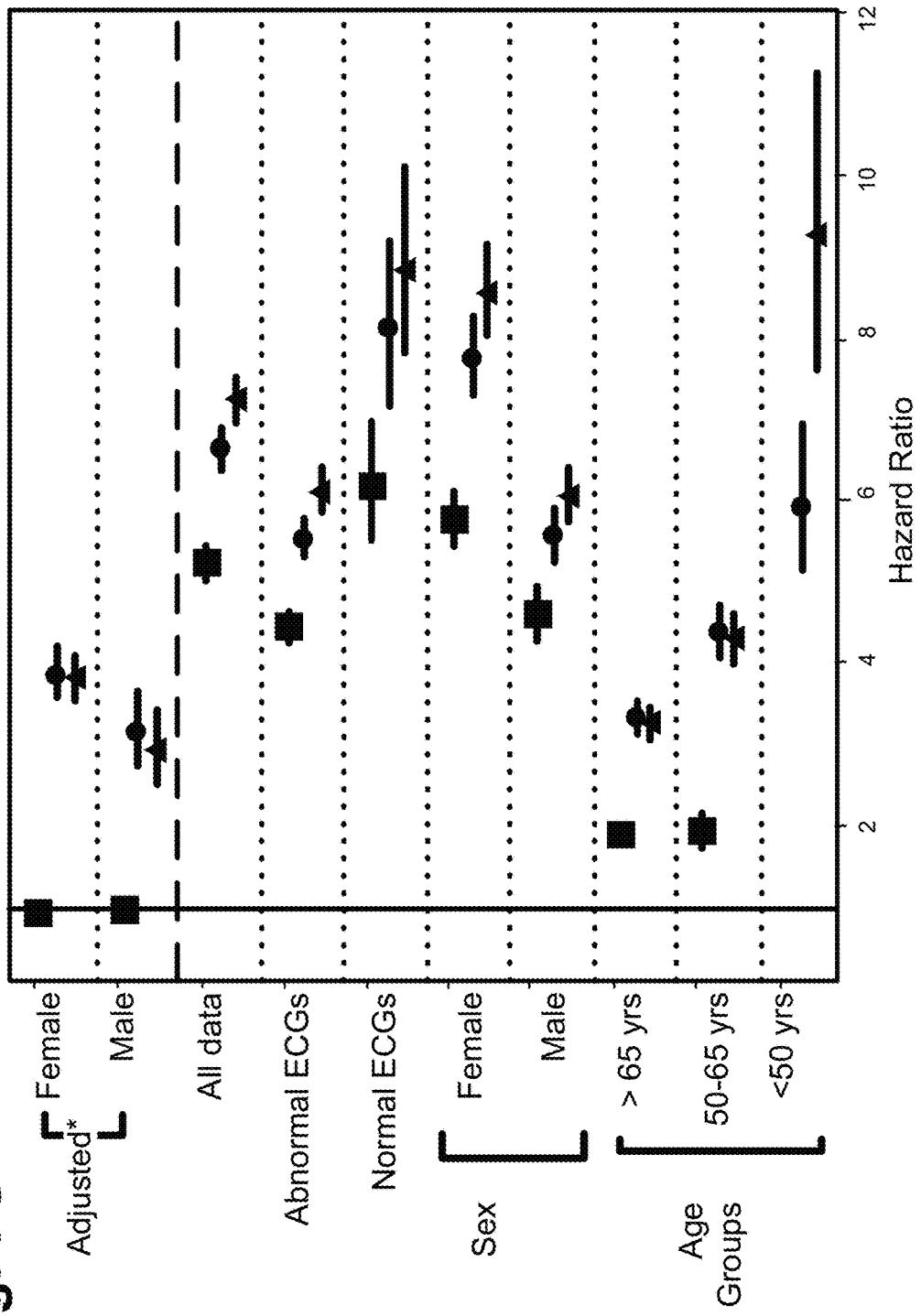
FIG. 7G is a plot of hazard ratios (HR) with 95% confidence intervals (CI) for the three models in subpopulations defined by age groups, sex and normal or abnormal ECG label.

The KM curves and HR for the three AF-prediction models in FIGS. 7A-D are illustrated in FIGS. 7E-G with the operating points marked on the corresponding ROC curves. Generally, FIGS. 7E-G illustrate receiver operating characteristic (ROC), incidence-free survival curves and hazard ratios in subpopulations for the following three models evaluated on the holdout set: (1) age & sex only (the inner dash-dot line); (2) DNN model with ECG traces only (outer dashed line) and (3) DNN model with ECG traces, age & sex (solid line) for all ECGs in the holdout set. FIG. 7E illustrates ROC curves with operating points marked for the three models. FIG. 7F illustrates incidence-free survival curves for the high- and low-risk groups for the operating point shown in A for a follow-up of 30 years. FIG. 7G shows a plot of hazard ratios (HR) with 95% confidence intervals (CI) for the three models in subpopulations defined by age groups, sex and normal or abnormal ECG label. Note that there is no HR for Age <50 years for model (1) as there was no subject classified as high-risk for new onset AF by the model for that subpopulation.

The DNN models showed significant HR of 6.7 [6.4, 7.0] and 7.2 [6.9, 7.6] in DNN-ECG and DNN-ECG-AS, respectively. Adjusting for age (in increments of 10 years) and sex (interactions with sex and model were significant) the HR were still significant: 3.7 [3.6, 4.1] and 3.1 [2.7, 3.4] in females and males, respectively, for the DNN-ECG model and 3.8 [3.6, 4.1] and 2.9 [2.5, 3.4] in females and males, respectively, in the DNN-ECG-AS model in FIG. 7F. For unadjusted comparisons, the DNN models had higher HR than the XGBoost model (age and sex) within all subsets defined by sex, age groups and ECG type (normal or abnormal).

Figure 7H:
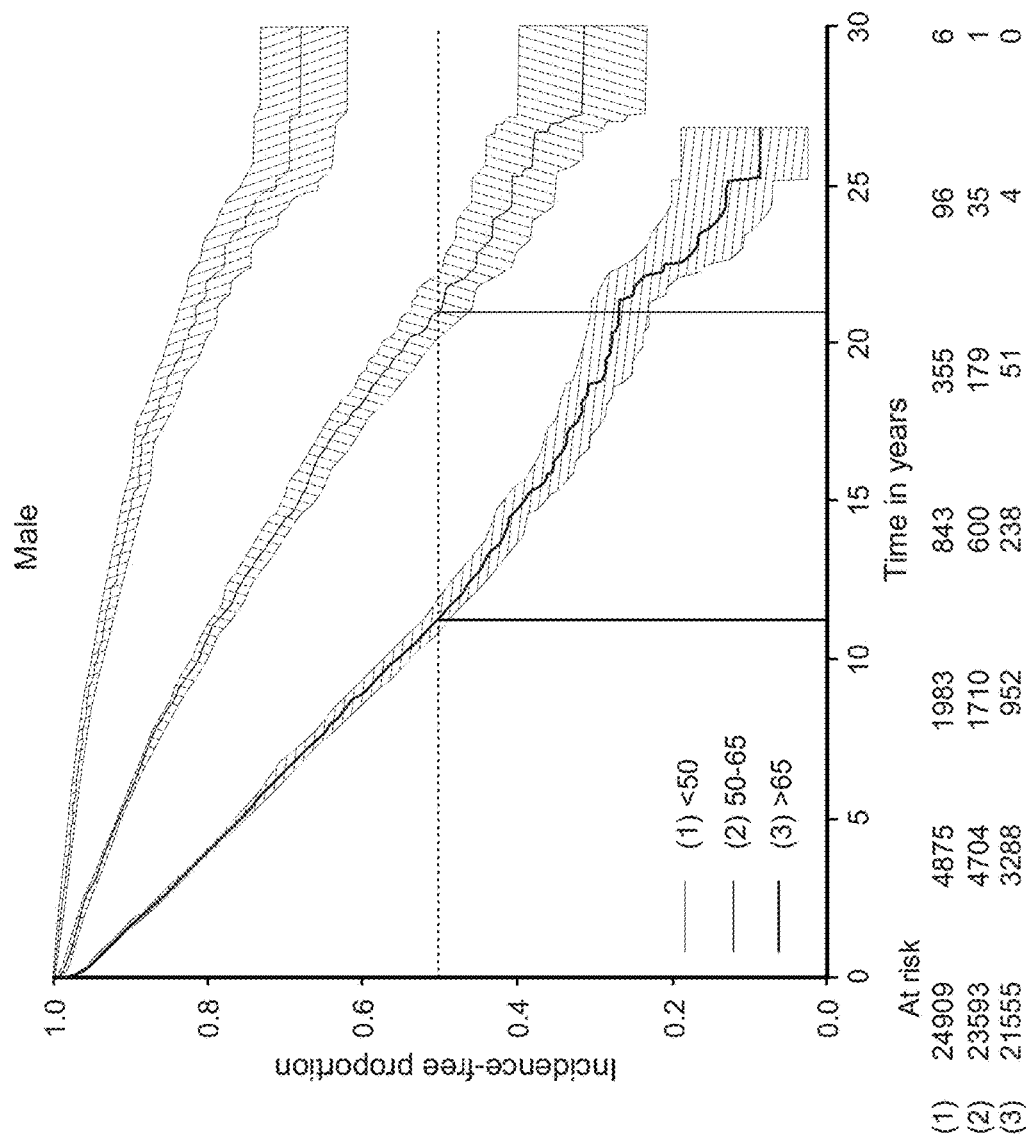
FIG. 7H is a plot of Kaplan-Meier (KM) incidence-free survival curves within the holdout set for males in age groups <50 years, 50-65 years and >65 years.
Figure 7I:
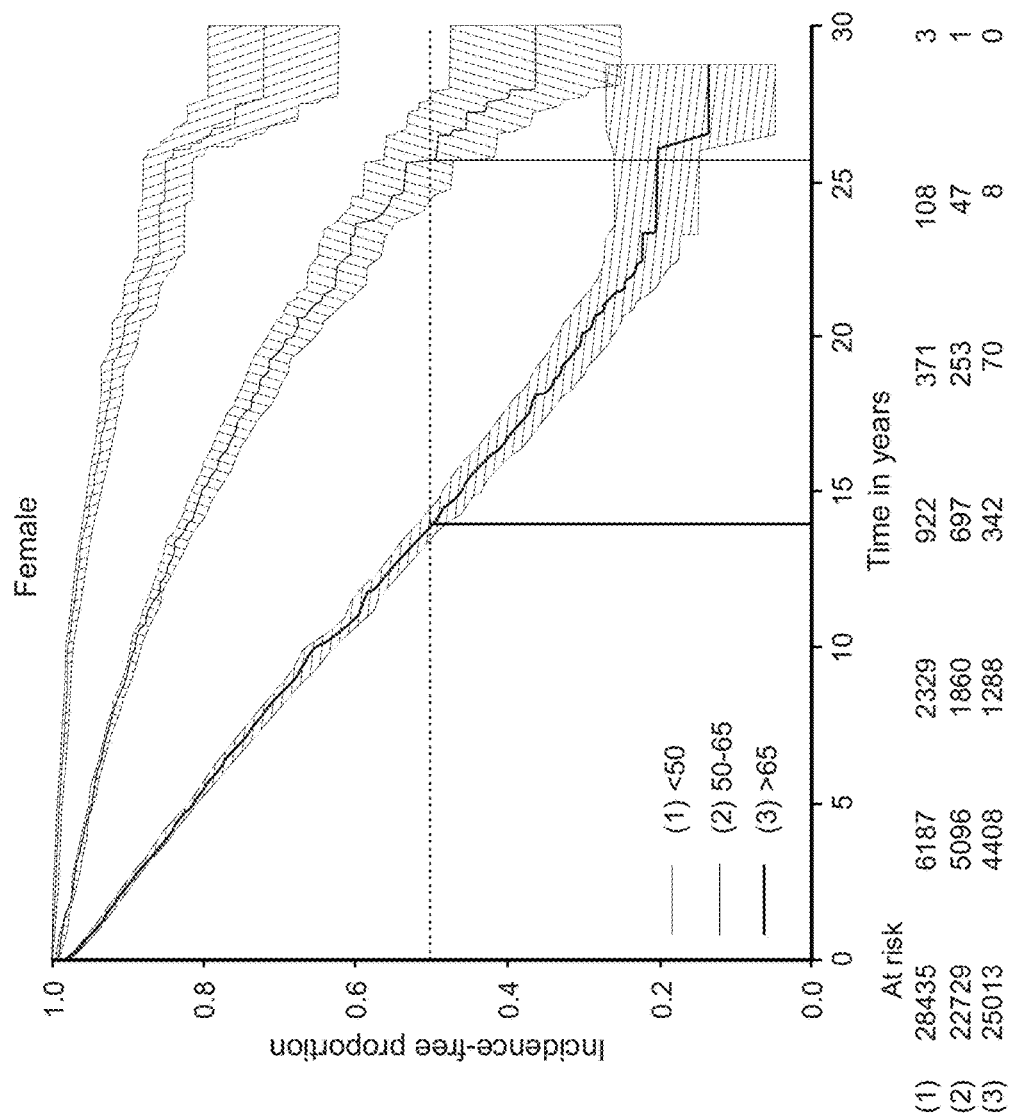
FIG. 7I is a plot of Kaplan-Meier (KM) incidence-free survival curves within the holdout set for females in age groups <50 years, 50-65 years and >65 years.

FIG. 7H shows Kaplan-Meier (KM) incidence-free survival curves within the holdout set for males in age groups <50 years, 50-65 years and >65 years. FIG. 7I shows Kaplan-Meier (KM) incidence-free survival curves within the holdout set for females in age groups <50 years, 50-65 years and >65 years.

Figure 7J:
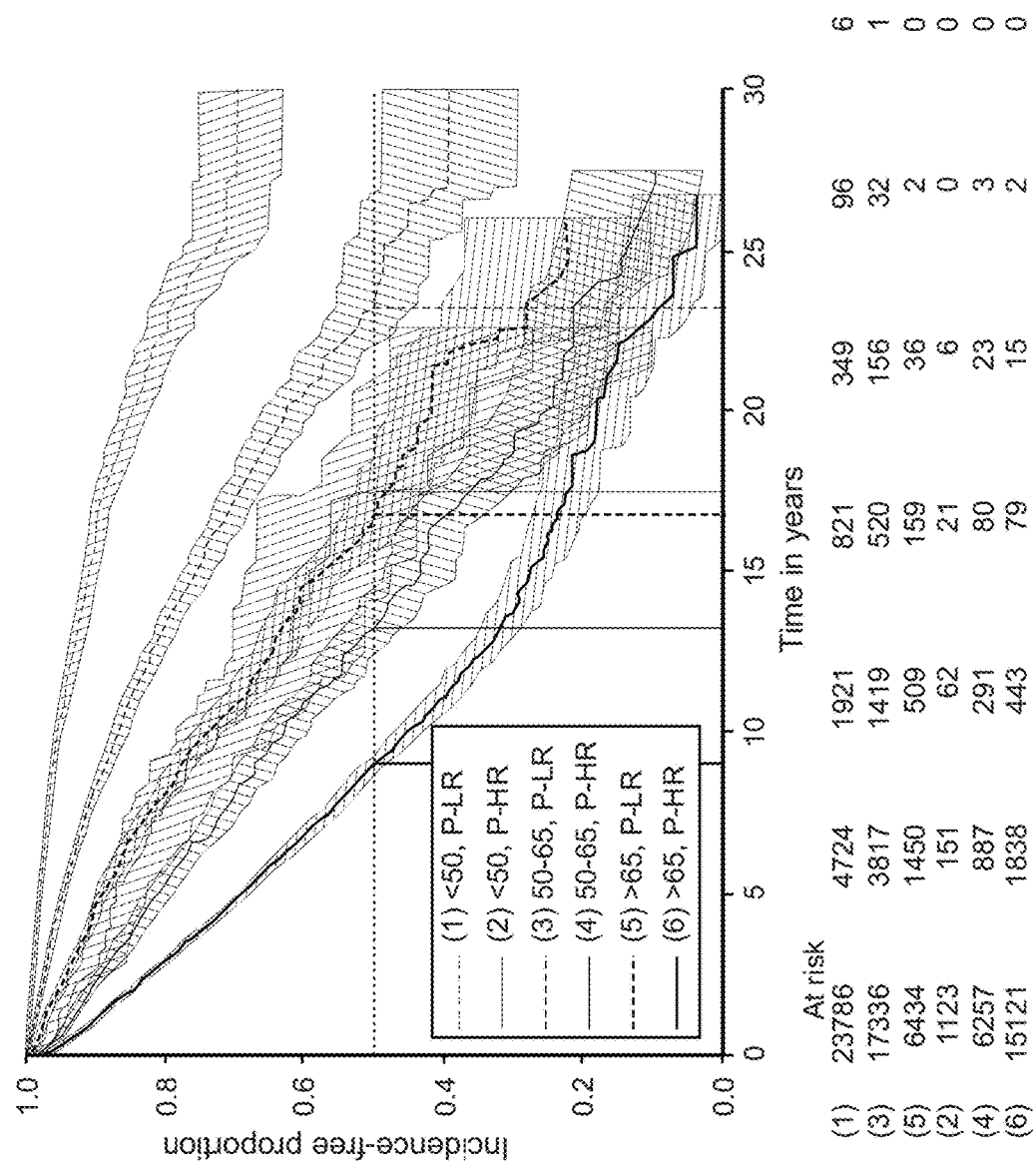
FIG. 7J is a plot of KM curves for the model (model M0 trained with ECG traces, age & sex) predicted low-risk and high-risk groups for new onset AF for males in age groups <50 years, 50-65 years and >65 years
Figure 7K:
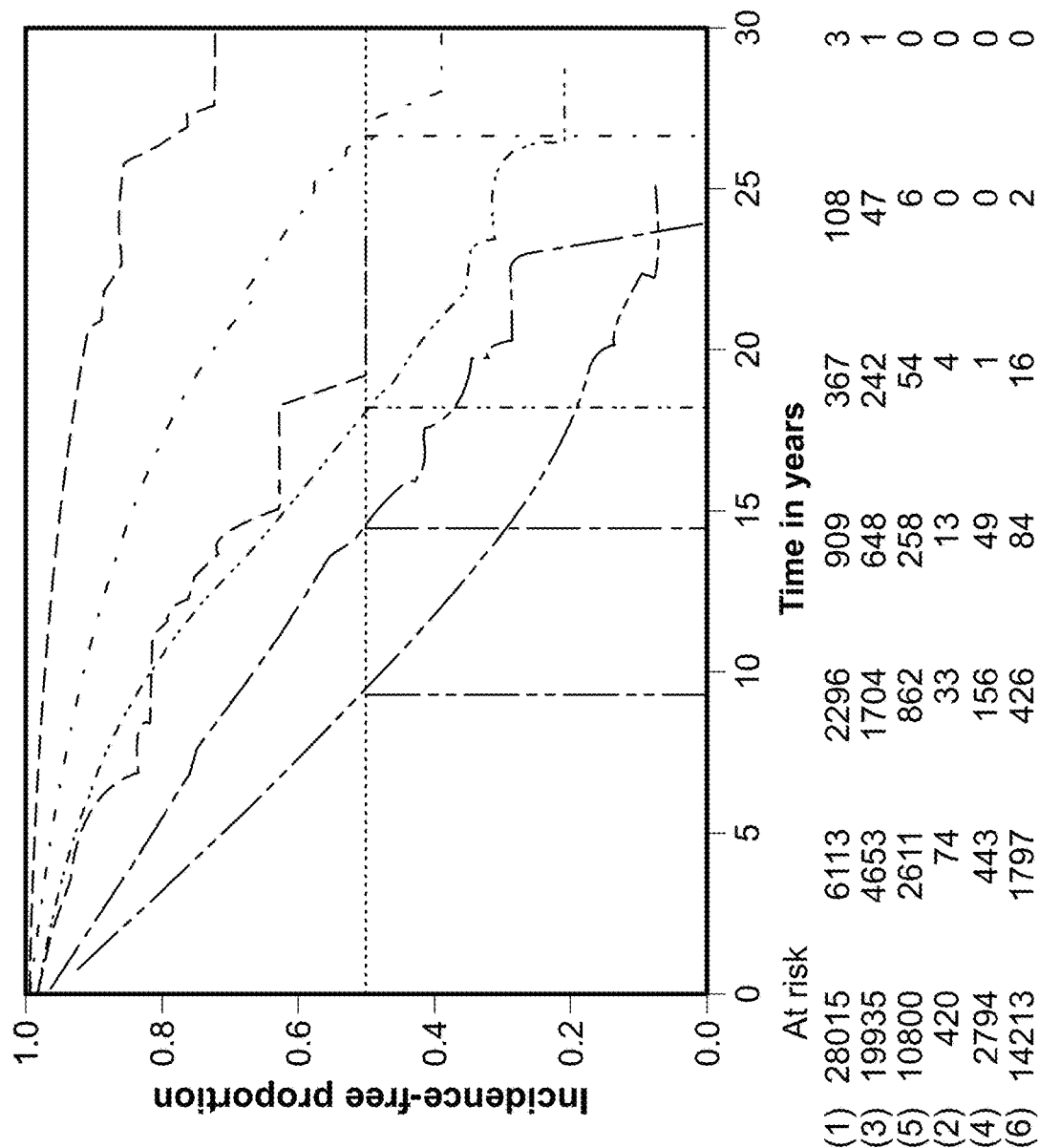
FIG. 7K is a plot of KM curves for the model predicted low-risk and high-risk groups for new onset AF for females in age groups <50 years, 50-65 years and >65 years.

FIG. 7J shows KM curves for the model (model M0 trained with ECG traces, age & sex) predicted low-risk and high-risk groups for new onset AF for males in age groups <50 years, 50-65 years and >65 years. FIG. 7K shows KM curves for the model predicted low-risk and high-risk groups for new onset AF for females in age groups <50 years, 50-65 years and >65 years.

FIGS. 7H and 7I show the KM curves for age groups <50, 50-65, and >65 years in males and females respectively. As expected, in both sexes, the survival curves are substantially different in each age group. However, FIGS. 7J and 7K show that in each age group the DNN model retains its ability to discriminate between a high risk and low risk population for the development of new onset AF for males and females respectively. Specifically, FIGS. 7J and 7K show the incidence of AF that occurs in a cohort of patients over time, where at time zero, no one has AF (100% incidence free), and at time N, shows how many patients had an AF incident. The model shows is sensitive to age as a driving feature because older patients typically predict higher incidence of AF over time than younger patients in the cohort. The superiority of the DNN model over age and sex alone is most evident in younger age groups and it is noted that no patient under 58 was predicted as high risk by the XGBoost model.

Figure 7L:
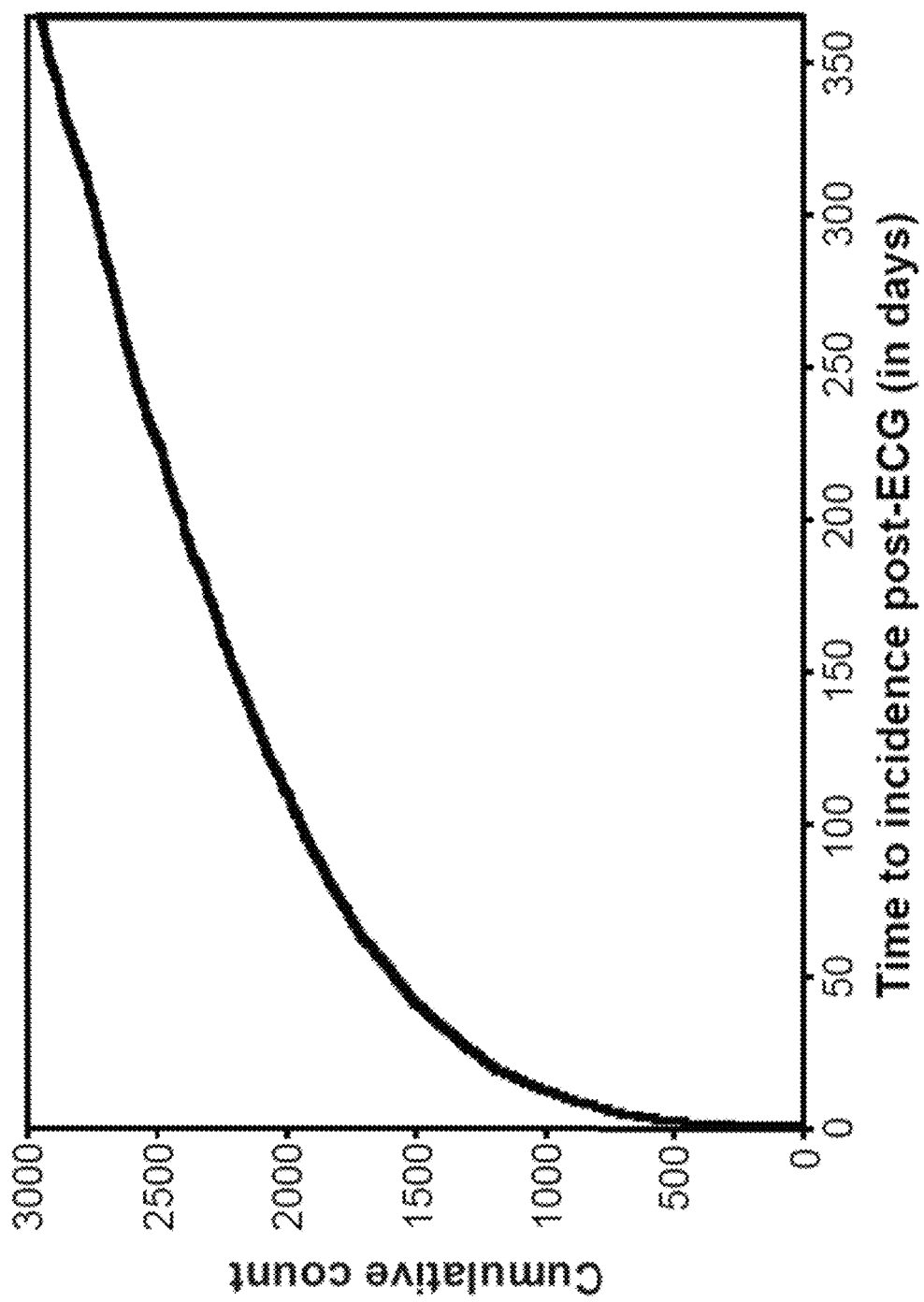
FIG. 7L is a plot showing a cumulative distribution of time to AF incidence after ECG in the holdout set of a proof-of-concept model.
Figure 8A:
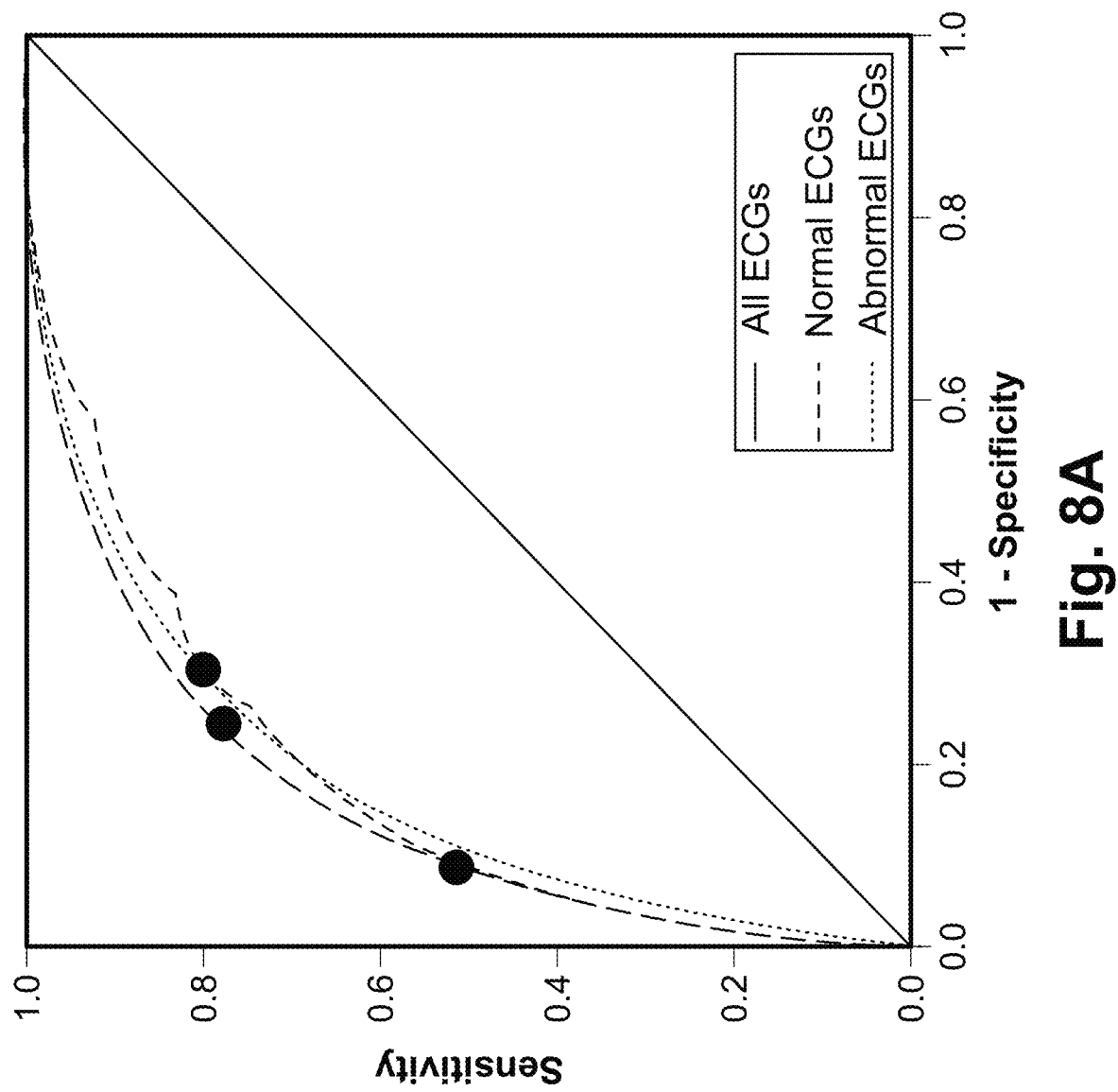
FIG. 8A is a graph of receiver operating characteristic curves with chosen operating points.
Figure 8B:
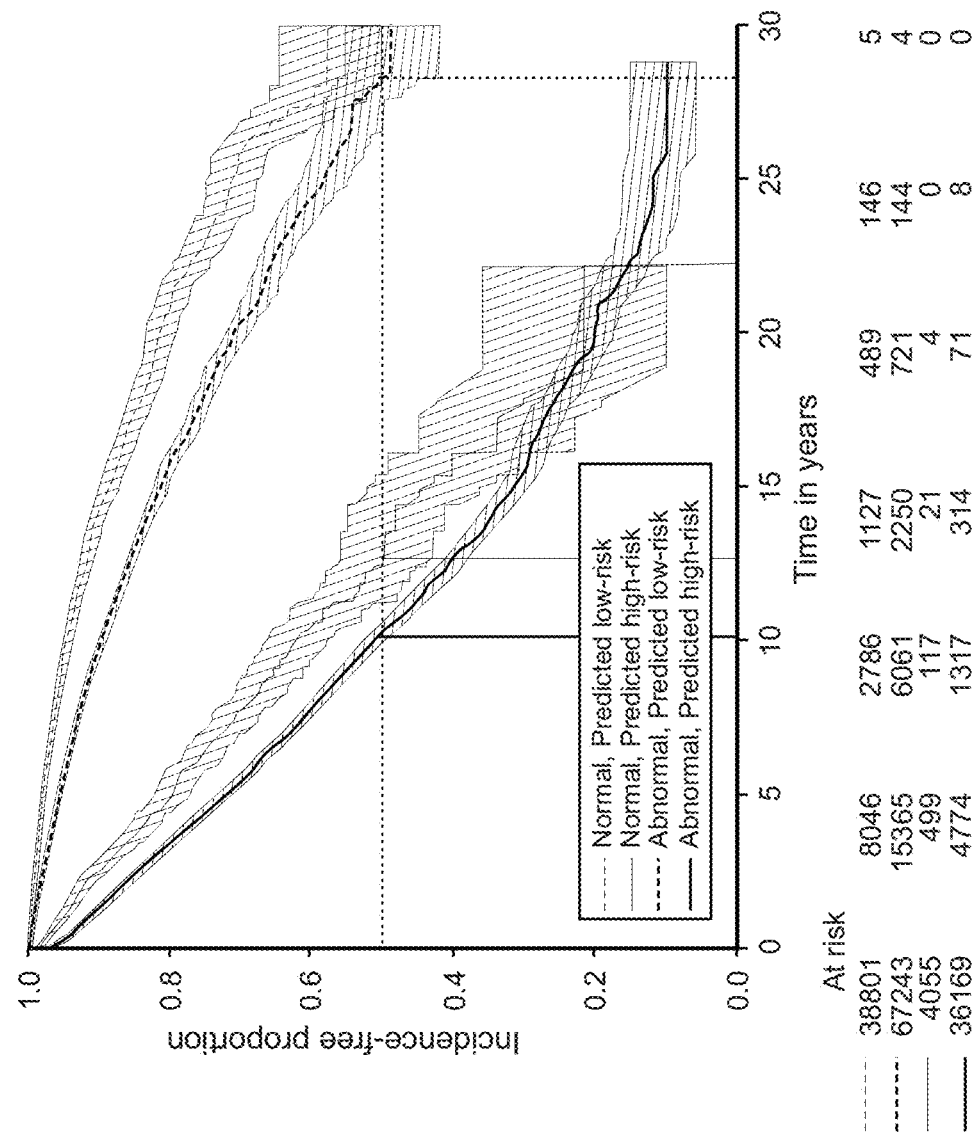
FIG. 8B is a graph of a Kaplan-Meier curve for predicted low and high-risk groups in the normal and abnormal ECG subsets at the operating points in FIG. 8A.
Figure 9:
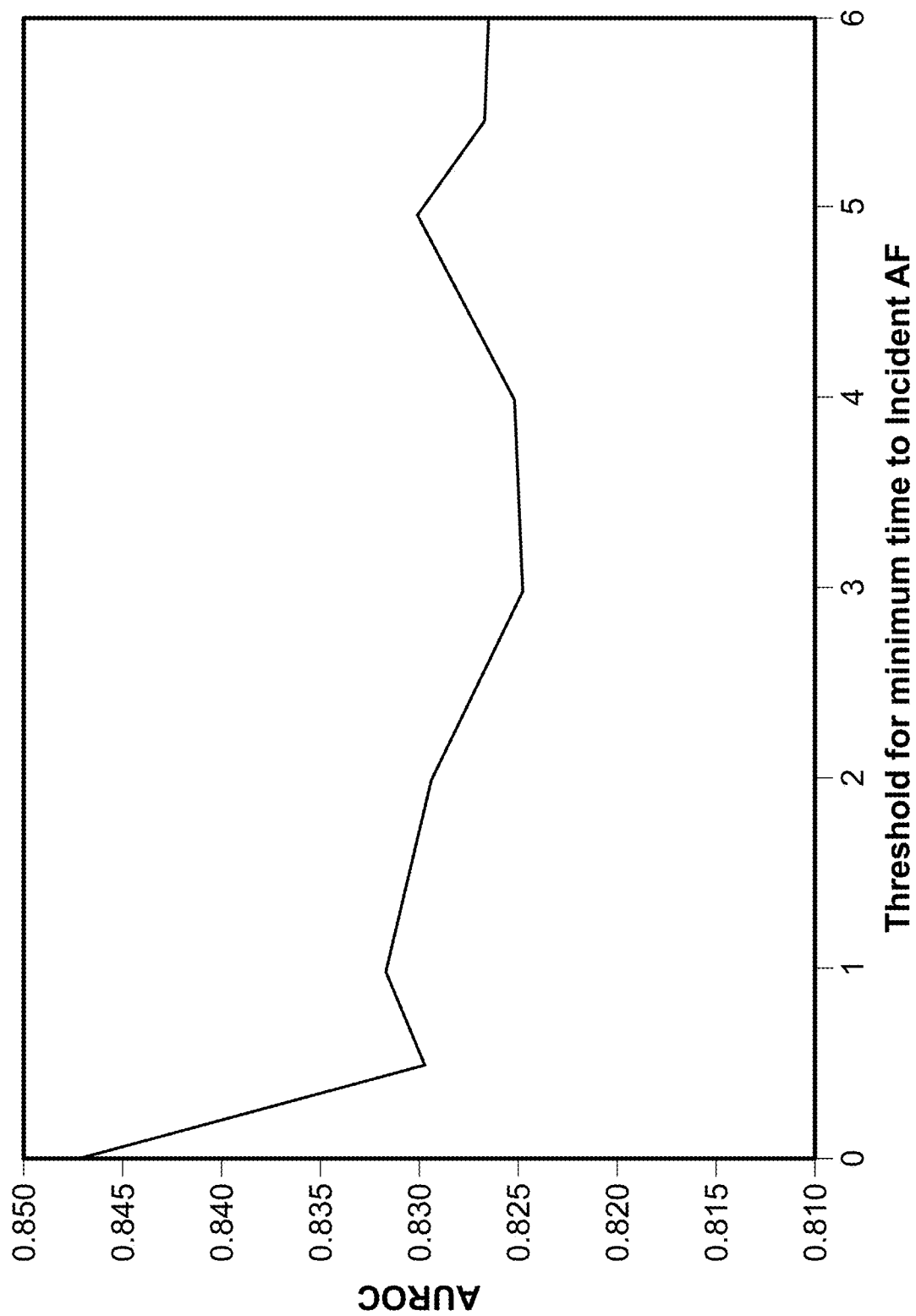
FIG. 9 is a graph of model performance as a function of the definition of time to incident AF after an ECG.

FIG. 8A is a graph of ROC curves with operating points marked for all the data (black circle on solid line), the normal ECG subset (black circle on dashed line) and the abnormal ECG subset (black circle on dotted line). FIG. 8B is a graph of a KM curve for predicted low and high-risk groups in the normal and abnormal ECG subsets at the operating points in FIG. 8A. The shaded area is the 95% confidence interval. The table below the graph shows the at-risk population for the given time intervals in the holdout test set. Moreover, the DNN maintained high performance even within the subgroup of ECGs clinically reported as 'normal', as well as the abnormal ECGs (FIG. 7; FIG. 8A). These results were observed to be both generalizable and robust based on the comparable performance of the cross-validation models (M1-M5) to M0, and the stability of the M0 metrics with repeated iteration of random sampling within the holdout set. Finally, the model maintained high performance even in the data subset who developed AF 6 months after ECG (these represent true incident cases, such as potentially paroxysmal cases that manifested quickly from 1 day to 6 months after ECG were excluded) with AUROC of 0.83 (FIG. 9). FIG. 9 is a graph of model performance as a function of the definition of time to incident AF after the ECG. The y-axis represents the area under the receiver operating characteristic curve (AUROC) and the x-axis represents different thresholds for defining incident AF. For example, cases corresponding to the "2" on the x-axis are those who developed AF at least 2 months after the baseline ECG (those developing AF within the first 2 months after ECG were excluded). An AUROC of 0.87 for AF presenting exclusively between 1-31 days following the sinus rhythm ECG was computed, consistent with the findings of others for identification of paroxysmal AF from sinus rhythm.

DNN 1-Year AF Risk Prediction is Associated with Long-Term AF Hazard

Survival free of AF as a function of DNN prediction (low risk vs. high risk for incident AF) is shown in FIG. 8B. While the proportion of patients predicted as high risk, 1 year incidence free AF was high, the high-risk prediction was associated with a significant increase in longer term hazard for AF over the next 3 decades. Specifically, the hazard ratios were 7.2 (95% CI: 6.9-7.56) in all ECGs, 8.2 (7.2–9.3) in normal ECGs, and 6.2 (5.9–6.5) in abnormal ECGs comparing those predicted high risk versus low risk for the development of AF within 1 year. Furthermore, the median incidence-free survival times of the two groups identified as low risk and high risk were 13 years and greater than 30 years, respectively, for normal ECGs and 10 and 28 years, respectively, for abnormal ECGs.

Prediction of New Onset AF can Enable Prevention of Future Stroke

Figure 10:
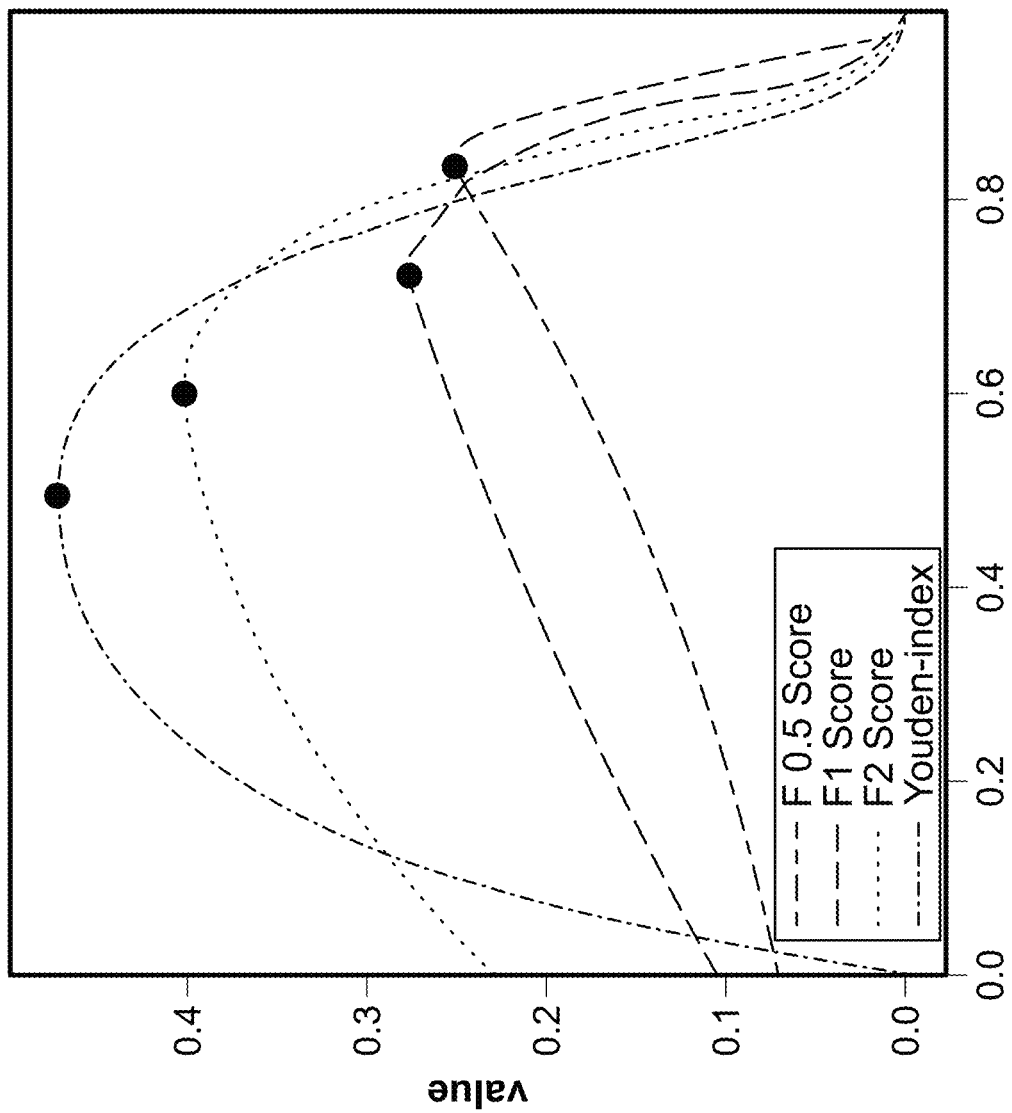
FIG. 10 is graph of a selection of an operating point on an internal validation set in a simulated deployment model.

In the deployment experiment, the model trained on data prior to 2010 and tested on data from 2010-2014 exhibited high performance overall for 1-year incident AF prediction, with AUROC and AUPRC of 0.83 and 0.17, respectively. Table 2 summarizes additional model performance characteristics at specific operating points dictated by maximal F0.15, F0.5, F1, and F2 scores (with progressively increased emphasis on recall e.g., sensitivity) (FIG. 10). FIG. 10 is a graph of the selection of the operating point on the internal validation set in the simulated deployment model using the Fb score or Youden index. These different points resulted in 1, 4, 12 and 20% of the overall population being flagged as high risk, corresponding with 28, 21, 15 and 12% positive predictive values and 4, 17, 45 and 62% strokes within 3 years of ECG were potentially preventable, respectively. In each of these cases, the number needed to screen (NNS) to find one new AF case at one year was low (4-9).

Table 2 is summary of the performance of the model trained with ECGs and age and sex to predict one-year incident atrial fibrillation (AF) in the deployment scenario for four different operating points defined in the independent internal validation set.

TABLE 2

| | Model predicted risk for new onset AF within 1 year of ECG | | | | | | | |
|---|---|---|---|---|---|---|---|---|
| Operating Point | # of ECGs flagged high risk | % of all ECGs flagged high risk | NNS to find 1 new onset AF | Sensitivity (Recall) (%) | Specificity (%) | Number of patients predicted high risk for AF who developed an AF-related stroke within x years of ECG (NNS) | | |
| | | | | | | x = 1 | x = 2 | x = 3 |
| $F_{0.5}$ score | 7958 | 4.4 | 5 | 26.9 | 96.4 | 17 (468) | 41 (194) | 65 (122) |
| $F_1$ score | 21831 | 12.1 | 7 | 52 | 89.3 | 51 (428) | 115 (190) | 167 (131) |
| $F_2$ score | 37428 | 20.7 | 9 | 68.7 | 81 | 69 (542) | 158 (237) | 231 (162) |
| Youden index | 50995 | 28.3 | 11 | 77.8 | 73.5 | 75 (680) | 182 (280) | 269 (190) |

Independent of the model, 3,497 patients out of 181,969 (1.9%) were observed to have a stroke following an ECG within the deployment test set. Of these, 96, 250 and 375 patients had a stroke within 1, 2 and 3 years, respectively, of the ECG and received a diagnosis of new AF between −3 and 365 days of the stroke. Of those 96, 250, and 375 patients, 84, 229, and 342 were not on an anticoagulant at the time of the stroke and represent potentially preventable AF-related strokes (FIG. 6A).

Figure 11:
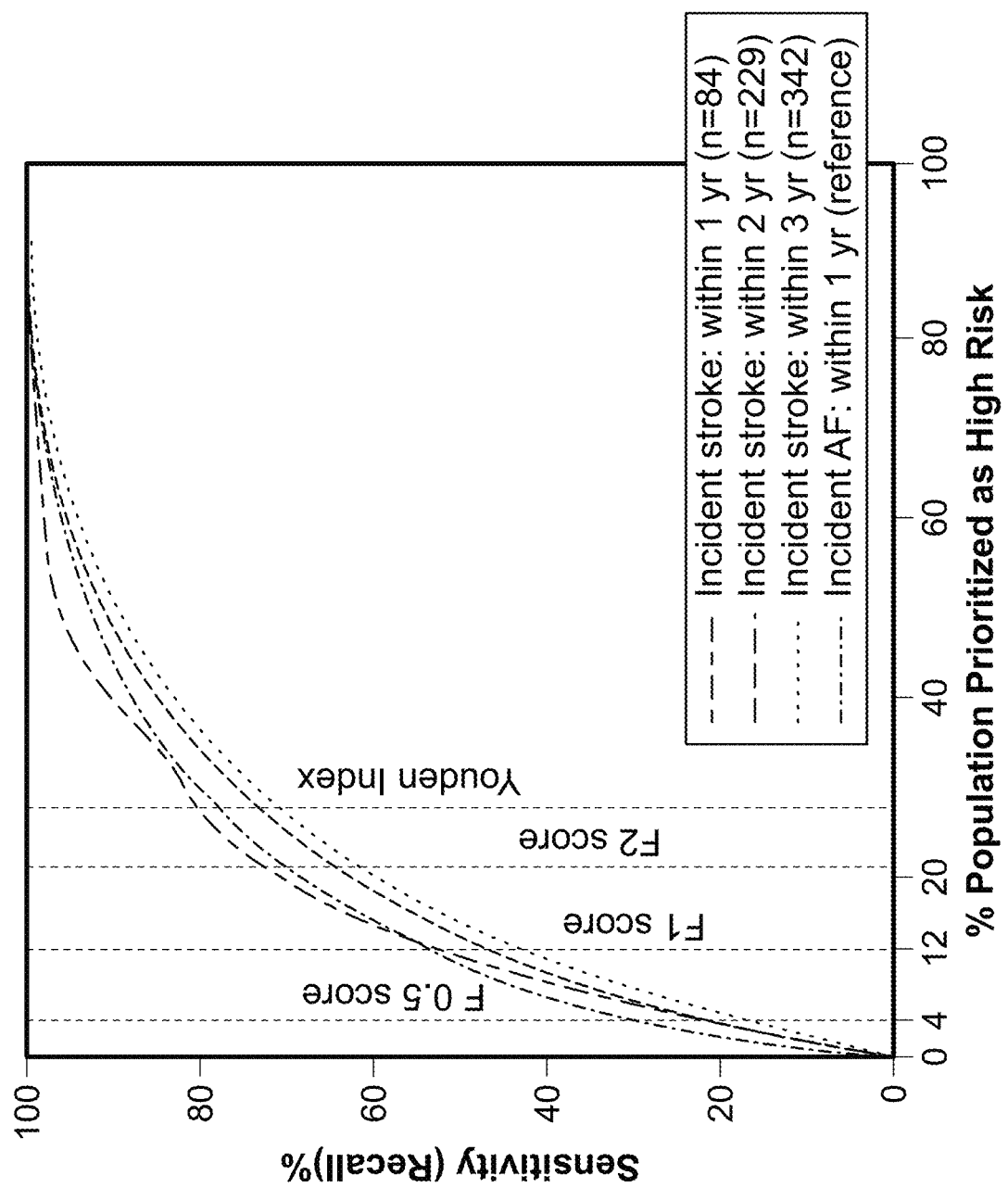
FIG. 11 is a graph of sensitivity of a model to potentially prevent AF-related strokes that developed within 1, 2 and 3 years after ECG generation as a function of the percentage of the population targeted as high risk to develop incident AF.

FIG. 11 is a graph of sensitivity of the model to potentially prevent AF-related strokes that developed within 1, 2 and 3 years after ECG as a function of the percentage of the population targeted as high risk to develop incident AF. Grey dotted lines represent the corresponding optimal operating thresholds from Table 2. FIG. 11 shows the model's potential for selecting a high-risk population that can then be screened for new onset AF with the goal of stroke prevention. Three conclusions can be drawn from FIG. 11. One, the ability to identify potentially preventable AF-related strokes is proportional to the ability to identify new AF. Two, a substantial amount of incident AF can be identified by screening a relatively small percentage of the population. Three, a variable operating point allows for tradeoffs between precision and recall that can be tailored to varying priorities.

3,497 patients out of 181,969 (1.9%) with ischemic stroke following an ECG within the deployment test set (2010-2014) were observed. Of these, 96, 250 and 375 patients had a stroke within 1, 2 and 3 years, respectively, of an ECG and received a new diagnosis of AF within 365 days following the stroke. Of those 375 patients, 342 were not on an anticoagulant at the time of the stroke, 31 were on anticoagulant medications for reasons other than AF, and 2 patients had insufficient records to determine if they were being treated with anticoagulants at the time of the stroke. Hence, these 375 represent a cohort at risk of AF-related strokes at the time of ECG.

Applying the model (trained on data prior to 2010) to this deployment test set, good performance for the prediction of new onset AF at one year (AUROC=0.83, AUPRC=0.17) was observed. Using an operating point determined by the F2 score, the sensitivity was 69%, specificity 81%, and number needed to screen (NNS) to find one case of new onset AF at one year was 9. 62% (231 of 375) of patients who had an AF-related stroke within 3 years of an ECG were predicted high risk for new onset AF (FIG. 11). The NNS to identify AF in one patient who developed an AF related stroke within 3 years of a high-risk prediction was 162. Table 3 is a performance summary of the DNN model (with age and sex) for predicting one-year new onset AF in a deployment scenario and potential to identify patients at risk for AF-related stroke within 3 years of ECG. Results are shown based on model predictions using the full test set, as well as specified population subsets with varying demographic, clinical setting, or comorbidity characteristics. Table 3 shows favorable test characteristics in subgroups defined by age, sex, race, comorbidities, clinical setting and $CHA_2DS_2VASc$ score.

TABLE 3

| Data | Method/ Subgroup | Data (%) | AF incidence (%) | New onset AF within 1 year of ECG | | | | Number predicted high risk for AF who developed an AF related stroke within 3 years (NNS) |
|---|---|---|---|---|---|---|---|---|
| | | | | Proportion of ECGs flagged high risk (%) | NNS to find 1 new onset AF | Ss (Recall) (%) | Sp (%) | |
| Full Test Set | F2 score | 100 | 3.5 | 21 | 9 | 69 | 81 | 231 (162) |
| Sex | Male | 45 | 4.1 | 25 | 9 | 70 | 77 | 109 (106) |
| | Female | 55 | 2.9 | 17 | 9 | 67 | 84 | 122 (141) |
| Race | White | 97 | 3.5 | 21 | 9 | 69 | 81 | 227 (162) |
| | Black | 2.3 | 1.7 | 11 | 13 | 49 | 90 | 3 (156) |
| | Others | 0.8 | 1.2 | 11 | 12 | 75 | 90 | 1 (179) |
| Comorbidities | CHD | 9 | 7.8 | 52 | 8 | 84 | 50 | 66 (129) |
| | HF | 1.3 | 18.8 | 77 | 4 | 92 | 27 | 17 (109) |
| | HT | 46.7 | 4.6 | 28 | 9 | 70 | 74 | 162 (146) |
| | T2DM | 14.4 | 5.3 | 33 | 8 | 74 | 69 | 63 (137) |
| | None above | 49 | 2.2 | 13 | 9 | 65 | 88 | 57 (202) |
| Patient setting | Outpatient | 49 | 2.1 | 13 | 13 | 51 | 87 | 63 (189) |
| | Emergency | 26 | 5.2 | 26 | 6 | 77 | 77 | 117 (105) |
| | Inpatient | 6 | 7.3 | 41 | 7 | 78 | 62 | 20 (232) |
| | Unknown | 18 | 3.4 | 27 | 11 | 73 | 75 | 31 (279) |
| Age groups | <50 years | 32 | 0.5 | 2 | 15 | 23 | 98 | 2 (551) |
| | 50-65 years | 33 | 2.2 | 12 | 12 | 47 | 89 | 23 (308) |
| | ≥65 males | 15 | 8.4 | 54 | 8 | 81 | 48 | 91 (164) |
| | ≥65 females | 19 | 6.7 | 42 | 8 | 76 | 61 | 115 (125) |
| $CHA_2DS_2$ VASc score | <2 | 53 | 1.4 | 7 | 12 | 43 | 93 | 18 (382) |
| | ≥2 | 47 | 5.8 | 36 | 8 | 76 | 66 | 213 (143) |

AF: Atrial Fibrillation/Flutter;
NNS: Number needed to screen;
CHD: Coronary Heart Disease;
HF: Heart Failure;
HT: Hypertension;
T2DM: Type II Diabetes Mellitus;
Ss: sensitivity;
Sp: Specificity This disclosure describes a deep neural network that, trained on 12-lead resting ECG data, can predict incident AF within 1 year, in patients without a history of AF, with high performance (AUROC=0.85). Moreover, it is demonstrated that this DNN outperformed both a clinical model (CHARGE-AF) and a machine learning model using age and sex within the same dataset. The superiority of the performance of the model compared with the reported performances of other models is noted: CHARGE-AF (AUROC=0.77), ARIC (AUROC=0.78), and Framingham (AUROC=0.78). It is also noted that the shorter prediction interval of the model 400 (1 year compared to 5-10 years) allows for a more actionable prediction, and that this prediction retains significant prognostic potential over the next 3 decades. Finally, by identifying a high-risk population that can be targeted for screening (e.g. with wearable devices or continuous monitors), the data demonstrate that a significant proportion of AF-related strokes can likely be prevented.

Over 25% of all strokes are thought to be due to AF, and ~20% of strokes due to AF occur in individuals not previously diagnosed with AF. A real-world scenario was simulated by applying the model 400 to ECGs acquired over a 5-year period and cross-referencing predicted high risk ECGs with future ischemic stroke incidences that were deemed potentially preventable (concurrent/subsequent identification of AF and no current use of anticoagulation). A range of different model operating points were considered based on the expectation that implementation of such screening initiatives would differ in scope across different health care settings. These differences would be reflected in varied preferences for total screening numbers vs. proportion of AF identified and number of strokes potentially prevented.

At one end of this performance spectrum, in which only the top 1% of the population is identified as high risk, positive predictive values approaching 28% were observed for the detection of 1-year AF (NNS for AF=4). This precision translated to screening volumes (NNS) of 120-361 for incident strokes occurring between 0 and 3 years from baseline. However, this lower screening volume was offset by a lower total recall (sensitivity) of preventable strokes (4% for strokes within 3 years post-ECG). At the other end of the spectrum in which 21% of the population was identified as high risk for developing AF, the preventable stroke recall improved substantially (62% for strokes within 3 years post-ECG), but at the expense of considerable increases in screening volume for both AF (NNS=9) and stroke (NNS=162-542 for 3-year or 1-year incidences, respectively). These numbers for screening volumes compare favorably with other well accepted screening tests including mammography (NNS 476 to prevent 1 breast cancer death ages 60-69), prostate specific antigen (NNS 1410 to prevent one death from prostate cancer), and cholesterol (NNS 418 to prevent one death from cardiovascular disease).

The model 400 can be incorporated into routine screening such that every ECG is evaluated and high-risk studies could be flagged for follow-up and surveillance. Such increased surveillance could take many different forms, including systematic pulse palpation, systematic ECG screening, continuous patch monitors worn once or multiple times, intermittent home screening with a device such as Kardia mobile, or wearable monitors such as the Apple Watch. While these methods could be used in isolation to screen for AF, combination with a DNN predictive model may help to overcome the challenges associated with the overall low incidence of AF in the general population, especially in younger age groups. Age is generally thought to be the predominant risk factor in guiding AF screening strategies, yet in this study 38% of all new AF (within a year of ECG) and 36% of all potentially preventable strokes (within 3 years of ECG) occurred under the age of 70.

Figure 12:
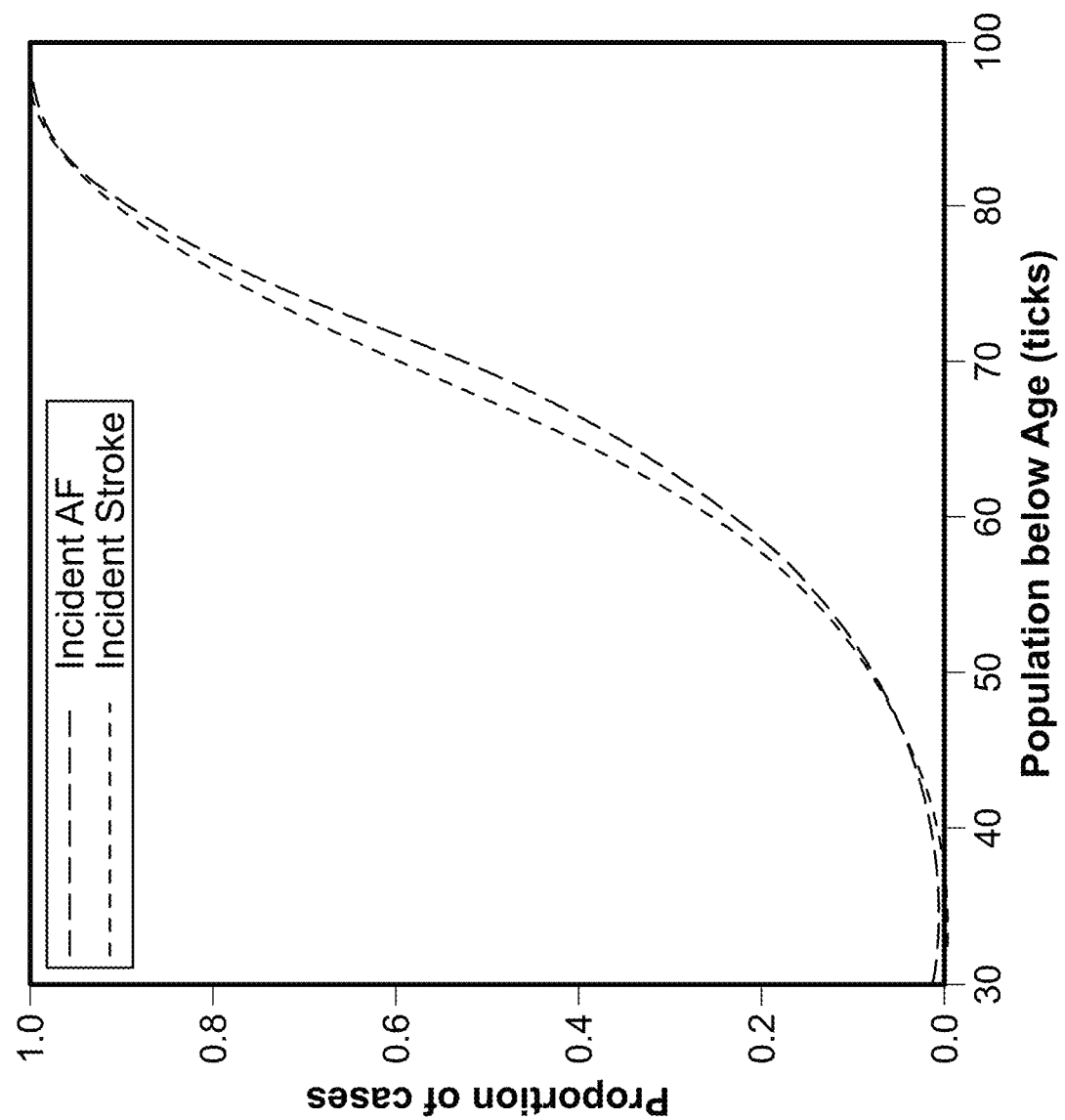
FIG. 12 is a graph of percent of all incident AF (within 1 year post-ECG) and strokes (within 3 years post-ECG) in the population as a function of patients below the given age threshold.

FIG. 12 is a graph of percent of all incident AF (within 1-year post-ECG) and strokes (within 3 years post-ECG) in the population as a function of patients below the given age threshold. The model 400 can be used in all patients over the age of 18 and has outperformed a model that uses age and sex alone.

The model 400 may detect paroxysmal AF and predicting new onset AF. This is in distinction to other techniques that focus solely on the identification of paroxysmal AF without the ability to predict incident AF. As noted above, the results indicate that the model 400 is doing both. One piece of evidence supporting our assertion that the DNN model can predict truly new onset AF is the continued separation of the Kaplan Meier curves up to thirty years after the index ECG as noted in FIGS. 7H-K.

Over 25% of all strokes are thought to be due to AF, and ~20% of strokes due to AF occur in individuals not previously diagnosed with AF. Once AF is detected anticoagulation is effective at preventing stroke but screening for AF is difficult due to the paroxysmal nature of AF and the fact that it is often asymptomatic. Screening strategies involving patch monitors, wearables, and other devices can be used to detect AF but are most effective in populations with a high prevalence of AF. The underlying goal for developing this prediction model is to identify a high-risk population that can then be selected for additional monitoring with the goal of finding AF prior to a stroke.

Figure 13:
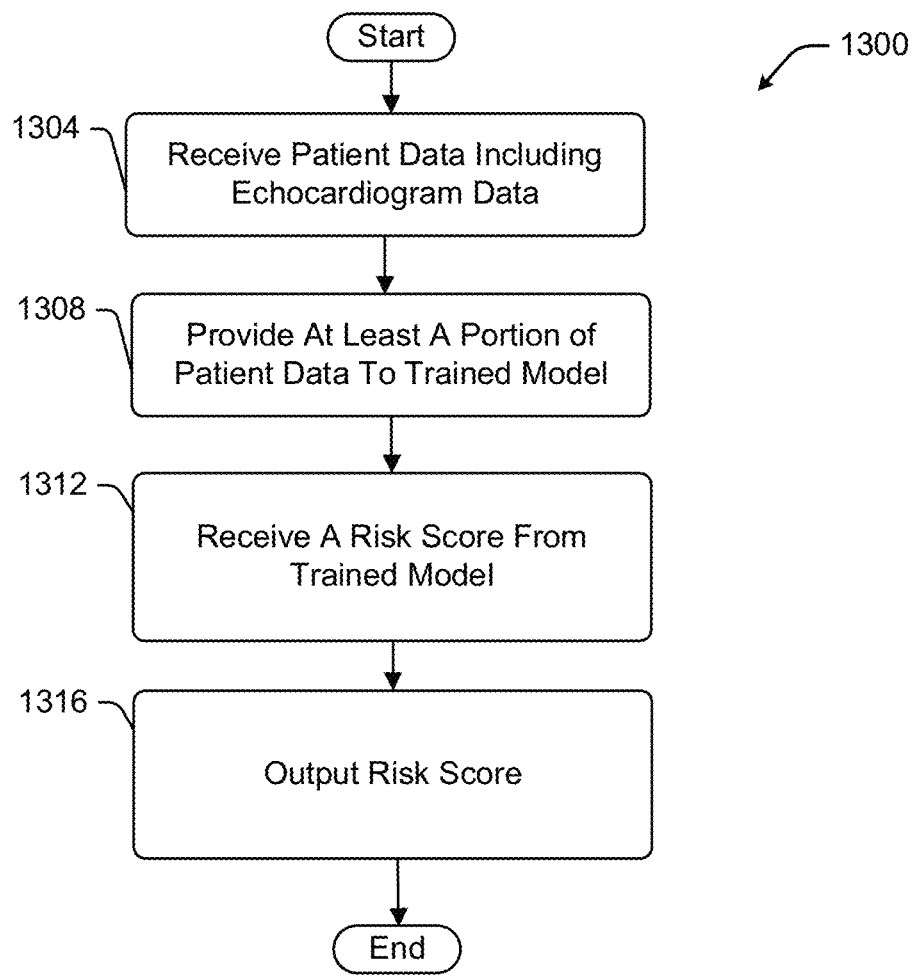
FIG. 13 is an exemplary process for generating risk scores using a model, such as the model in FIG. 4A.

A real-world scenario was simulated by applying our model to all ECGs acquired within a large regional health system over a 5-year period by cross-referencing predicted high-risk ECGs with future ischemic stroke incidences that were deemed potentially preventable (concurrent/subsequent identification of AF). It was found that a high proportion (62%) of patients who suffered an AF-related stroke were correctly predicted as high risk for AF. The NNS to identify AF in one patient who later suffered an AF-related stroke was 162. This compares favorably with other well accepted screening tests including mammography (NNS 476 to prevent 1 breast cancer death ages 60-69), prostate specific antigen (NNS 1410 to prevent one death from prostate cancer), and cholesterol (NNS 418 to prevent one death from cardiovascular disease). Not all patients with AF are at high risk for stroke and scoring systems such as $CHA_2DS_2VASc$ are commonly used to determine the need for anticoagulation. A $CHA_2DS_2VASc$ score of 2 or greater is the cupoint most commonly used to start an anticoagulant and Table 3 shows that the model performs well within that subgroup with a NNS of 8 to find 1 new case of AF. Table 3 also shows that 92% of patients predicted high risk for AF who later suffered an AF-related stroke had a $CHA_2DS_2VASc$ score of 2 or greater and were potentially eligible for anticoagulation FIG. 13 is an exemplary process 1300 for generating risk scores using a model. In some embodiments, the model can be the model 400 in FIG. 4A. In some embodiments, the model can be the model 424 in FIG. 4B. The risk score can be indicative of whether or not a patient will suffer from and/or develop a condition within a predetermined time period (e.g., six months, one year, ten years, etc.). In some embodiments, the process 1300 can be included in the ECG analysis application 132 in FIG. 1. In some embodiments, the process 1300 can be implemented as computer readable instructions on one or more memories or other non-transitory computer readable medium, and executed by one or more processors in communication with the one or more memories or media. In some embodiments, the process 1300 can be implemented as computer readable instructions on the memory 220 and/or the memory 240 and executed by the processor 204 and/or the processor 224.

At 1304, the process 1300 can receive patient data including ECG data. The ECG data can be associated with the patient. In some embodiments, the ECG data can include the ECG voltage input data 300. In some embodiments, the ECG data can be associated with an electrocardiogram configuration including a plurality of leads and a time interval. The ECG data can include, for each lead included in the plurality of leads, voltage data associated with at least a portion of the time interval. In some embodiments, the ECG data can include first voltage data associated with the lead I and a first portion of the time interval, second voltage data associated with the lead V2 and a second portion of the time interval, third voltage data associated with the lead V4 and a third portion of the time interval, fourth voltage data associated with the lead V3 and the second portion of the time interval, fifth voltage data associated with the lead V6 and the third portion of the time interval, sixth voltage data associated with the lead II and the first portion of the time interval, seventh voltage data associated with the lead II and the second portion of the time interval, eighth voltage data associated with the lead II and the third portion of the time interval, ninth voltage data associated with the lead VI and the first portion of the time interval, tenth voltage data associated with the lead VI and the second portion of the time interval, eleventh voltage data associated with the lead VI and the third portion of the time interval, twelfth voltage data associated with the lead V5 and the first portion of the time interval, thirteenth voltage data associated with the lead V5 and the second portion of the time interval, and fourteenth voltage data associated with the lead V5 and the third portion of the time interval.

The ECG data can include a first branch (e.g., "branch 1") including leads I, II, V1, and V5, acquired from time (t)=0 (start of data acquisition) to t=5 seconds, a second branch (e.g., "branch 2") including leads V1, V2, V3, II, and V5 from t=5 to t=7.5 seconds, and a third branch (e.g., "branch 3") including leads V4, V5, V6, II, and V1 from t=7.5 to t=10 seconds as shown in FIG. 3. In some embodiments the process 1300 may also receive demographic data and/or other patient information associated with the patient. The demographic data can include an age value and a sex value of the patient or additional variables (e.g., race, weight, height, smoking status, etc.) for example from the electronic health record. In some embodiments, the process 1300 can receive one or more EHR data points. In some embodiments, the EHR data points can include laboratory values (blood cholesterol measurements such as LDL/HDL/total cholesterol, blood counts such as hemoglobin/hematocrit/white blood cell count, blood chemistries such as glucose/sodium/potassium/liver and kidney function labs, and additional cardiovascular markers such as troponins and natriuretic peptides), vital signs (blood pressures, heart rate, respiratory rate, oxygen saturation), imaging metrics (such as cardiac ejection fractions, cardiac chamber volumes, heart muscle thickness, heart valve function), patient diagnoses (such as diabetes, chronic kidney disease, congenital heart defects, cancer, etc.), treatments (including procedures, medications, referrals for services such as cardiac rehabilitation, dietary counseling, etc.), echo measurements, ICD codes, and/or care gaps.

In some embodiments, the ECG data can be generated over a single time interval (e.g., ten seconds). In some embodiments, the ECG data can include the ECG voltage input data 428. In some embodiments, the ECG voltage input data can include five thousand data points collected over a period of 10 seconds and 8 leads including leads I, II, V1, V2, V3, V4, V5, and V6.

In some embodiments, the ECG data can include leads originally sampled at 500 Hz. In some embodiments, the ECG data can include leads originally sampled at 250 Hz and linearly interpolated to 500 Hz. In some embodiments, the ECG data can include leads originally sampled at 1000 Hz and downsampled to 500 Hz. Thus, a variety of ECG systems and/or sampling settings can be used with the same trained model.

At 1308, the process can provide at least a portion of the patient data to a trained model. In some embodiments, the trained model can be the model 400. In some embodiments, the process 1308 can provide the ECG data to the model. In some embodiments, the process 1300 can include providing the first voltage data, the sixth voltage data, the ninth voltage data, and the twelfth voltage data to the first channel, providing the second voltage data, the fourth voltage data, the seventh voltage data, the tenth voltage data, and the thirteenth voltage data to the second channel, and providing the third voltage data, the fifth voltage data, the eighth voltage data, the eleventh voltage data, and the fourteenth voltage data to the third channel. In some embodiments, the ECG data can include voltage data for all leads over the entire time interval, and the process 1300 can include providing the voltage data to a single channel included in the trained model. In some embodiments, the process 1308 can provide the ECG data and the demographic data and/or the EHR data points to the model.

At 1312, the process 1300 can receive a risk score from the model. In some embodiments, the risk score can be an AF risk score that indicates a predicted risk of a patient developing AF within a predetermined time period from when the electrocardiogram data was generated. In some embodiments, the predetermined time period can be three months, six months, one year, five years, ten years, thirty years, or any other time period selected from the range of six months to thirty years. In some embodiments, the predetermined time period can be at least three months (e.g., three months, six months, etc.). In some embodiments, the predetermined time period can be at least six months (e.g., six months, one year, etc.). In some embodiments, the predetermined time period can be at least one year (e.g., one year, five years, etc.). In some embodiments, the predetermined time period can be at least five years (e.g., five years, ten years, etc.)

At 1316, the process can output the risk score to at least one of a memory (e.g., the memory 220 and/or the memory 240) or a display (e.g., the display 116, the display 208, and/or the display 228). In some embodiments, the display can be in view of a medical practitioner or healthcare administrator. In some embodiments, the process 1300 can generate and output a report based on the risk score. In some embodiments, the report can include the raw risk score and/or graphics related to the risk score. In some embodiments, the process 1300 can determine that the risk score is above a predetermined threshold associated with the condition (e.g., risk scores above the threshold can be indicative that the patient will suffer from the conditions within the predetermined time period). The process 1300 can then generate the report based on the determination that the risk score is above a predetermined threshold. In some embodiments, in response to determining that the risk score is above the predetermined threshold, the process 1300 can generate the report to include information (e.g., text) and/or links to sources (e.g., one or more hyperlinks) about treatments for the condition, causes of the condition, and/or other clinical information about the condition. In some embodiments, the process 1300 can generate the report from intermediate results stored in a standardized format, such as a standardized JavaScript Object Notation (JSON) format. The standardized format may also be converted to a different format for presentation to healthcare providers using format conversion software, such as for conversion into a healthcare providers' electronic health record system. In some embodiments, the process 1300 can generate the report to include name of the test, patient sex, patient date of birth, patient name, institution/physician name, and/or medical record number. In some embodiments, the process 1300 can generate the report to include an ECG waveform, which may, for instance, be a re-display of the original waveform data produced by the ECG or a re-drawn waveform that is validated for similarity to the original waveform. In some embodiments, the process 1300 can generate the report to include a recommendation, such as a treatment recommendation or a monitoring recommendation. For example, the report may include a recommendation that the patient be subject to additional cardiac monitoring, a significant step forward in detecting undiagnosed disease. As other examples, the report may include one or more recommendations for lifestyle modifications shown to reduce AF or other conditions (e.g., weight loss, alcohol abstinence, etc.), screen for undiagnosed AF or other condition triggers like sleep apnea, conduct more frequent follow-up, conduct future ECGs, assess heart rhythm via pulse palpation, or prescribe remote cardiac monitors. Physicians may proceed with any or none of these actions, or other appropriate patient management strategy, based on information from the device in combination with other symptoms and clinical factors. The process 1300 can then end.

A Deep Neural Network for Predicting Incident Atrial Fibrillation Directly from 12-Lead Electrocardiogram Traces An example of a neural network trained on clinically acquired ECGs is now described. From 2.7 million clinically-acquired 12-lead ECGs, 1.1 million ECGs without Afib (from 237,060 patients) were extracted. Presence or absence of future incident Afib was determined for each of the extracted ECGs via subsequent ECG studies and problem list diagnoses prepared by attending physicians. The prevalence of incident Afib was 7% in the entire population and 3% in the subset of 61,142 patients with ECGs clinically interpreted as normal.

A multi-class deep convolutional neural network, using 5-fold cross-validation, was trained to predict 1-year incident Afib (e.g., the target output variable) with 15 traces per ECG as input. We assessed model performance with area under a receiver operating characteristic curve (AUC) and performed Cox Proportional Hazard analysis on incidence-free curves of the predicted groups. To additionally evaluate model performance in the context of opportunistic population screening, we estimated the positive predictive value (PPV) of the model as a function of the number of patients with highest model-predicted risk to be screened.

Figure 14:
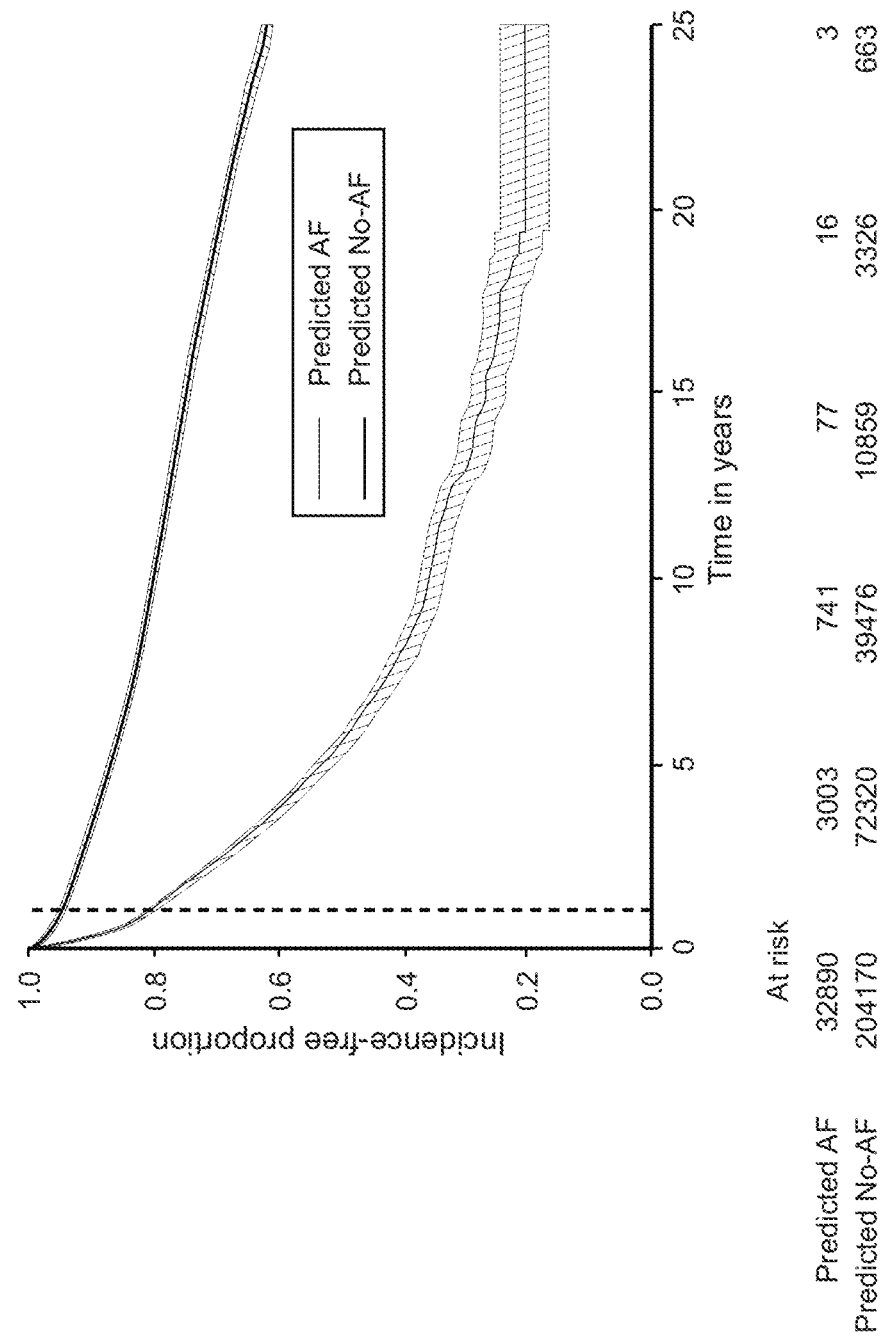
FIG. 14 is a graph illustrating the incidence-free proportion curve for predicted Afib and predicted no-Afib groups (likelihood threshold=0.5) with the available follow-up.

FIG. 14 is a graph illustrating the incidence-free proportion curve for predicted Afib and predicted no-Afib groups (likelihood threshold=0.5) with the available follow-up. The mean AUC of the predictive model was 0.75±0.02. Unit risk score increase was equivalent to 45% increased odds of developing AF within a year (Odds Ratio: 1.45 [95% confidence interval (CI): 1.15-1.66]). Even in the subset of ECGs interpreted as "normal" (e.g., physician was unable to visually identify irregularities), the AUC was 0.72±0.02.

Figure 15:
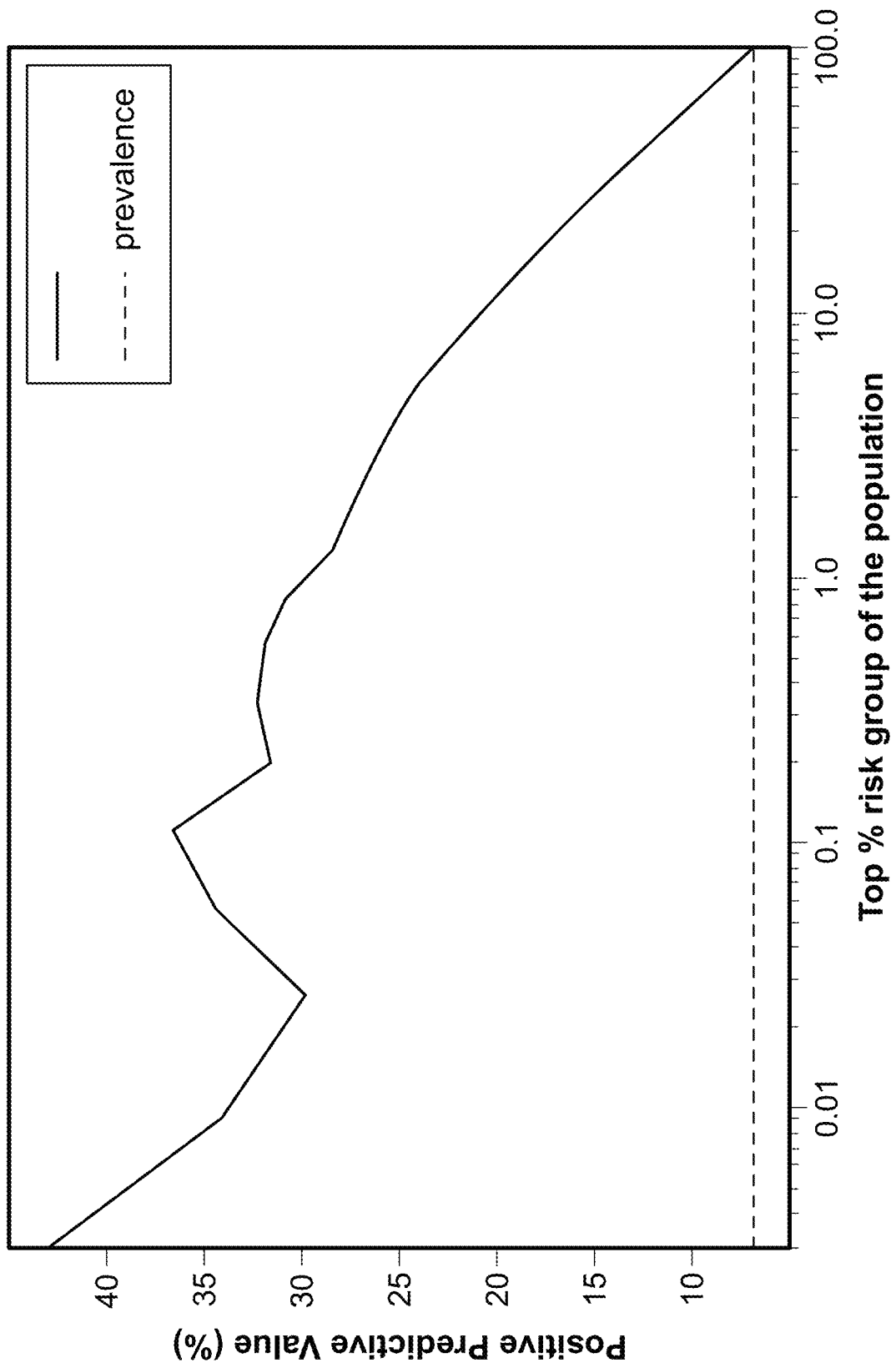
FIG. 15 is a graph illustrating the top % patients with highest risk and the positive predictive value across all the operating points of the future Afib predictive system.

FIG. 15 is a graph illustrating the top % patients with highest risk and the positive predictive value across all the operating points of the future Afib predictive system. In the setting of potential population screening, the interpretation performance corresponds to a PPV of 0.3 for screening the highest 1% at risk.

Deep Neural Networks can Predict 1-Year Mortality Directly from ECG Signal, Even when Clinically Interpreted as Normal 1,775,926 12-lead resting ECGs collected from 397,840 patients over 34 years, as well as age, sex and survival status were extracted from a single medical institution's electronic health records. 15 voltage-time 250-500 Hz traces (3 standard "long" 10 sec and 12 "short" 2.5 sec acquisitions) were extracted from each ECG along with 'ECG measures' (30 diagnostic patterns and 9 standard measurements). A deep neural network was trained to predict 1-year mortality (e.g., a variable output) directly from the ECG traces. A 5-fold cross-validated model using different variable inputs and Cox Proportional Hazard survival analysis were performed on the predicted groups to compare performance. Good predictive accuracy was identified within the subset of 297,548 ECGs called "normal" by the physician. A blinded survey of 3 cardiologists was performed to determine whether they were capable of seeing features indicative of mortality risk within the ECG data.

Figure 16:
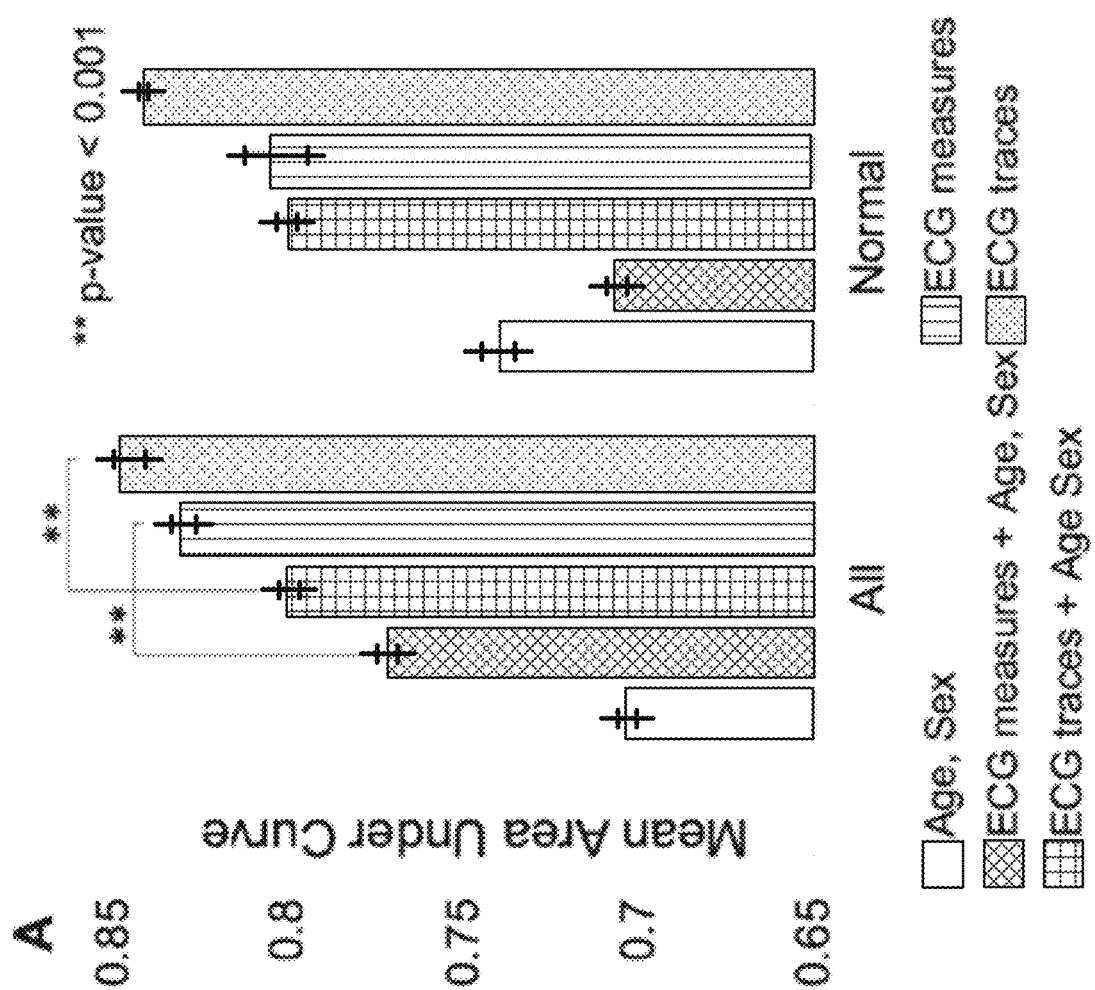
FIG. 16 is a bar plot of the mortality predicting model or system performance to predict 1-year mortality with ECG measures and ECG traces, with and without age and sex as additional features.

FIG. 16 is a bar plot of the mortality predicting model or system performance to predict 1-year mortality with ECG measures and ECG traces, with and without age and sex as additional features.

Figure 17:
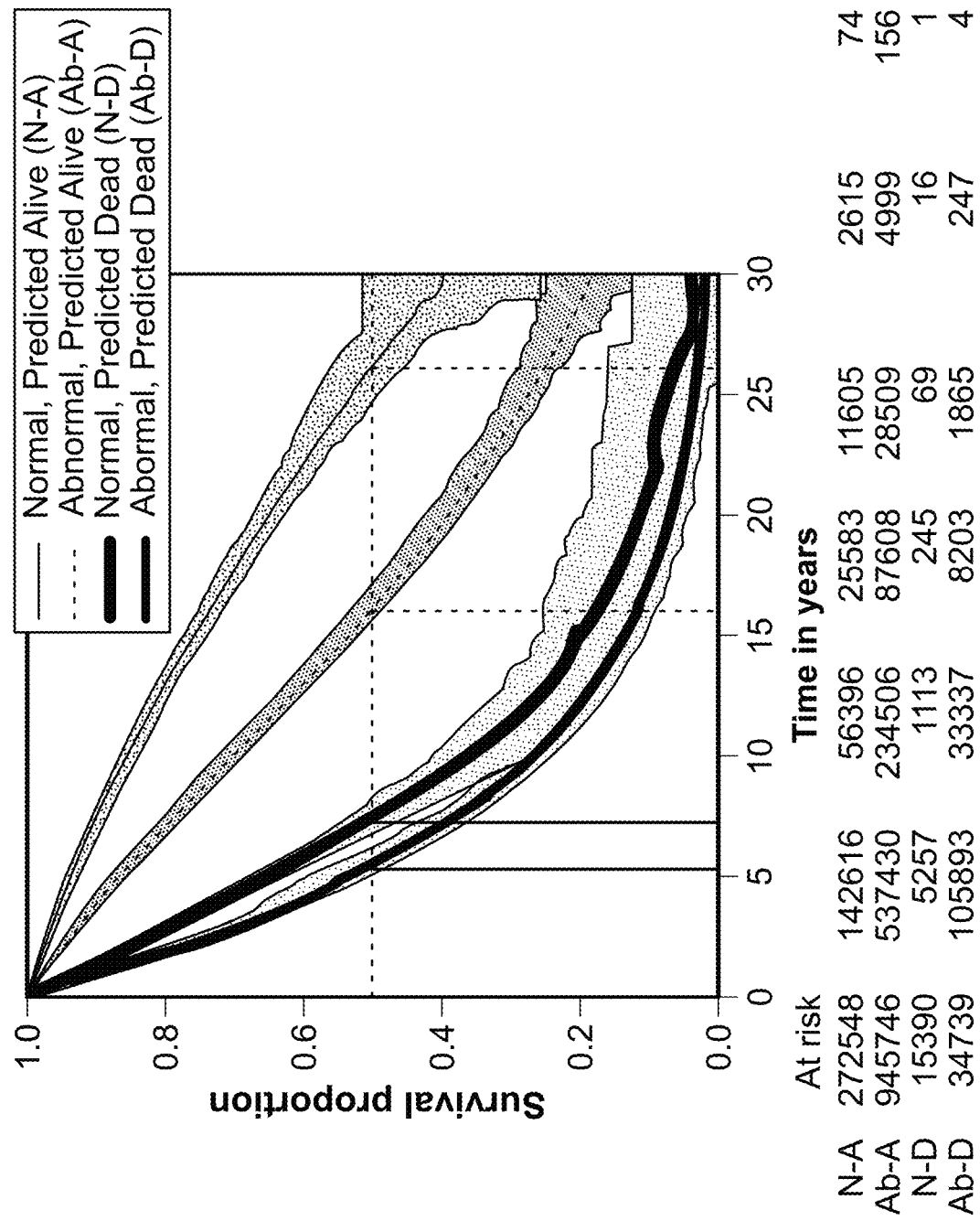
FIG. 17 is a graph illustrating the mean KM curves for predicted alive and dead groups in normal and abnormal ECG subsets beyond 1-year post-ECG.

FIG. 17 is a graph illustrating the mean KM curves for predicted alive and dead groups in normal and abnormal ECG subsets beyond 1-year post-ECG.

The model trained with the 15 traces alone yielded an average AUC of 0.83, which improved to 0.85 after adding age and sex. This model was superior to a separate, non-linear model created from the 39 ECG measures (AUC=0.77 and 0.81 without and with age and sex, respectively, p<0.001, see FIG. 16). Even within the "normal" ECGs, the model performance remained high (AUC=0.84), and the hazard ratio was 6.6 (p<0.005) beyond 1-year post-ECG (see FIG. 17). In the blinded survey, the patterns captured by the model were not visually apparent to cardiologists, even after being shown labeled true positives (dead) and true negatives (alive).

In some embodiments, the trained model can be included in the ECG analysis application 132, and can be used to predict 1-year mortality using a process similar to the process 1300 in FIG. 13.

Many ECG machines create a "portable document format" (PDF) from the voltage-time traces which may then be stored in the medical record. The underlying voltage data may be extracted from these PDFs by first converting the PDF to XML and then parsing the XML file for the underlying data points which make up each of the voltage-time traces. The XML, may also be parsed to determine the patient's age, sex, nine continuous numerical measurements output by the ECG machine (QRS duration, QT, QTC, PR interval, ventricular rate, average RR interval and P, Q and T-wave axes) and thirty categorical ECG patterns, including: a normal, left bundle branch block, incomplete left bundle branch block, right bundle branch block, incomplete right bundle branch block, atrial fibrillation, atrial flutter, acute myocardial infarction, left ventricular hypertrophy, premature ventricular contractions, premature atrial contractions, first degree block, second degree block, fascicular block, sinus bradycardia, other bradycardia, sinus tachycardia, ventricular tachycardia, supraventricular tachycardia, prolonged QT, pacemaker, ischemia, low QRS voltage, intra-atrioventricular block, prior infarct, nonspecific t-wave abnormality, nonspecific ST wave abnormality, left axis deviation, right axis deviation, and an early repolarization which may be diagnosed by a physician. Example code is presented below in APPENDIX A for converting from PDF to SVG format and from SVG to parsed data points.

Inclusion/Exclusion and Outputs from the Method of Reading the ECG

In some embodiments, a predictive model may be trained using a series of input variables, such as the ECG PDF, the variables extracted from the PDF, and the targeted output variables, such as a 1-year mortality rate. During the model training phase, labeled data is provided (in which both the inputs and outputs are known) to allow the model to learn how best to predict the output variables. Once the model has been trained, it may be deployed in a situation where only the input variables are known and the output may include a prediction target of interest. An exemplary target of interest may include a risk of 1-year mortality given the current ECG.

For model training, a series of 12-lead ECG traces may be extracted from an institutional clinical database. Such a database may include over 2.6 million traces, such as traces acquired of a period of time, including a period of time of months, years, or decades. In an example, the resting 12-lead ECGs with voltage-time traces of 2.5 seconds for 12 leads and 10 seconds for 3 leads (V1, II, V5) that did not have significant artifacts and were associated with at-least a year of follow-up or death within a year, may be extracted. Artifacts may include those identified by ECG software at the time of ECG; for example, ECG outputs that include "technically limited", "motion/baseline artifact", "Warning: interpretation of this ECG, although attempted, may be adversely affected by data quality", "Acquisition hardware fault prevents reliable analysis", "Suggest repeat tracing", "chest leads probably not well placed", "electrical/somatic/power line interference", or "Defective ECG". Extraction may further include 15 voltage-time traces (three 10-second leads and twelve 2.5-second leads). As such, a final dataset may include 1.8 million ECGs where 51% of them were stored at 500 Hz (Hz=samples per second) and the remaining were stored at 250 Hz. A preprocessing stage may include resampling the 250 Hz ECGs to 500 Hz by linear interpolation.

Other Inputs for Consideration, Including Additional Endpoints and EHR Data

In instances where additional data may inform the model, extraction may include records from electronic health records having additional patient data such as patient status (alive/dead) which may be generated by combining each patient's most recent clinical encounters from the EHR and a regularly-updated death index registry. Patient status is used as an endpoint to determine predictions for 1-year mortality after an ECG, however, additional clinical outcomes may also be predicted, including, but not limited to, mortality at any interval (1, 2, 3 years, etc.); mortality associated with heart disease, cardiovascular disease, sudden cardiac death; hospitalization for cardiovascular disease; need for intensive care unit admission for cardiovascular disease; emergency department visit for cardiovascular disease; new onset of an abnormal heart rhythm such as atrial fibrillation; need for a heart transplant; need for an implantable cardiac device such as a pacemaker or defibrillator; need for mechanical circulatory support such as a left ventricular/right ventricular/biventricular assist device or a total artificial heart; need for a significant cardiac procedure such as percutaneous coronary intervention or coronary artery bypass graft/surgery; new stroke or transient ischemic attack; new acute coronary syndrome; or new onset of any form of cardiovascular disease such as heart failure; or the likelihood of diagnosis from other diseases which may be informed from an ECG.

Moreover, additional variables may be added into a predictive model for purposes of both improving the prediction accuracy of the endpoints and identifying treatments which can positively impact the predicted bad outcome. For example, by extracting laboratory values (blood cholesterol measurements such as LDL/HDL/total cholesterol, blood counts such as hemoglobin/hematocrit/white blood cell count, blood chemistries such as glucose/sodium/potassium/liver and kidney function labs, and additional cardiovascular markers such as troponins and natriuretic peptides), vital signs (blood pressures, heart rate, respiratory rate, oxygen saturation), imaging metrics (such as cardiac ejection fractions, cardiac chamber volumes, heart muscle thickness, heart valve function), patient diagnoses (such as diabetes, chronic kidney disease, congenital heart defects, cancer, etc.) and treatments (including procedures, medications, referrals for services such as cardiac rehabilitation, dietary counseling, etc.), a model's accuracy may be improved. Some of these variables are "modifiable" risk factors that can then be used as inputs to the models to demonstrate the benefit of using a particular therapy. For example, a prediction may identify a patient as a 40% likelihood of developing atrial fibrillation in the next year, however, if the model was able to identify that the patient was taking a beta blocker, the predicted risk would drop to 20% based on the increased data available to the predictive model. In one example, demographic data 416 and patient data 1304 may be supplemented with these additional variables, such as the extracted laboratory values or modifiable risk factors.

Figure 18:
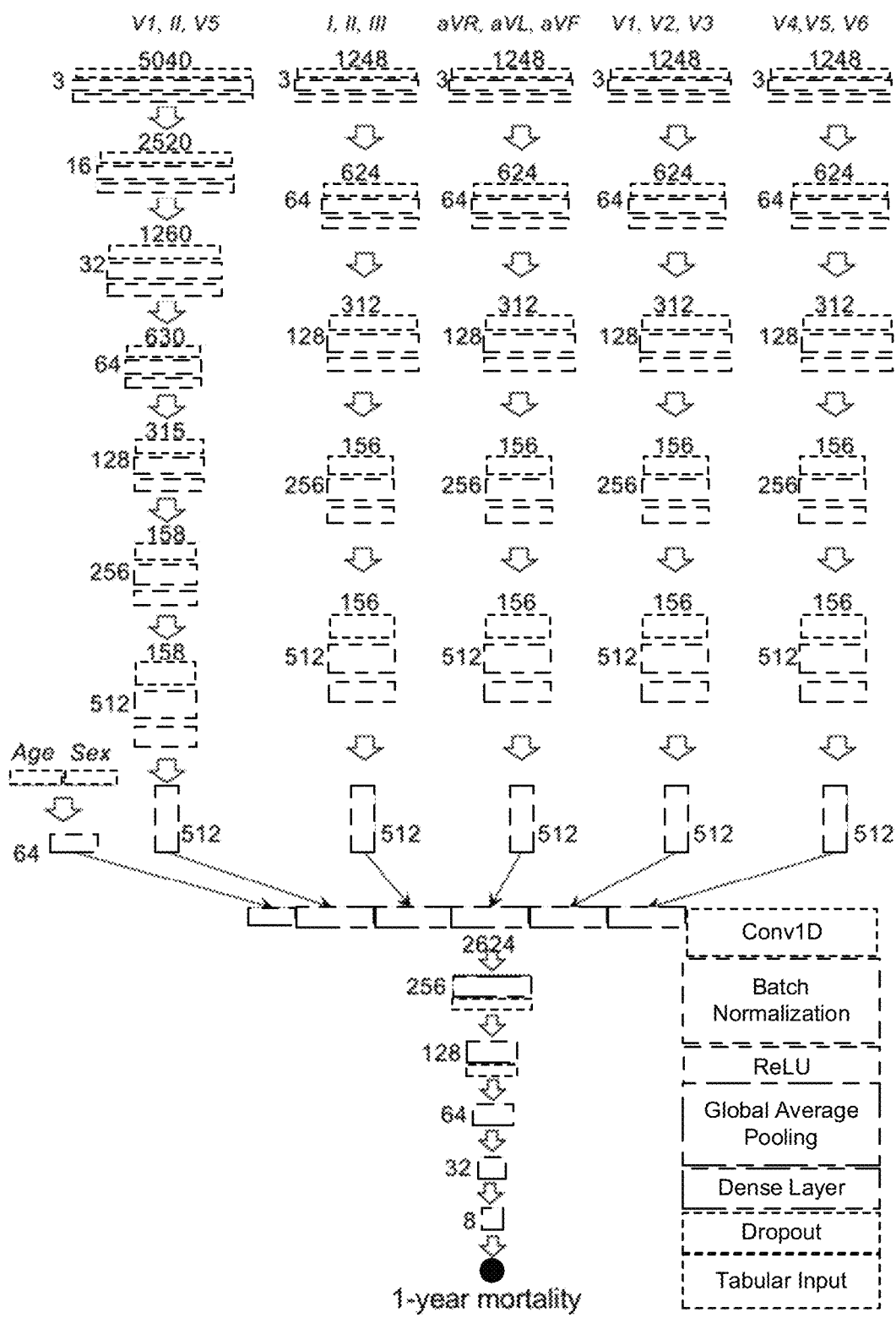
FIG. 18 is a model architecture for a convolutional neural network having a plurality of branches processing a plurality of channels each.

Machine learning models for implementing a predictive model may include a convolutional neural network (model architecture illustrated in FIG. 18 below) having a plurality of branches processing a plurality of channels each. FIG. 18 is a model architecture for a convolutional neural network having a plurality of branches processing a plurality of channels each. As shown, in some embodiments, the model can include five branches from which an input of three leads as channels concurrent in time, (Branch 1: [I, II, III]; Branch 2: [aVR, aVL, aVF]; Branch 3: [V1, V2, V3]; Branch 4: [V4, V5, V6] and Branch 5: [V1-long, II-long, V5-long]) may be utilized to generate predictions. In some multi-branch CNNs, each branch can represent the 3 leads as they were acquired at the same time, or during the same heartbeats. For Branch 5, which can include the "long leads," the leads can be sampled for a duration of 10 seconds. For the other four branches, the leads can be sampled for a duration of 2.5 seconds.

In a typical 12-lead ECG, four of these branches of 3 leads are acquired over a duration of 10 seconds. Concurrently, the "long leads" are recorded over the entire 10 second duration. To improve robustness of the CNN, an architecture may be designed to account for these details since abnormal heart rhythms, in particular, cause the traces to change morphology throughout the standard 10 second clinical acquisition. A traditional model may miss abnormal heart rhythms which present with morphology deviations during a longer, 10-second read.

A convolutional block may include a 1-dimensional convolution layer followed by batch normalization and rectified linear units (ReLU) activations. In one example, the first four branches and last branch may include 4 and 6 convolutional blocks, respectively, followed by a Global Average Pooling (GAP) layer. The outputs of all the branches may then be concatenated and connected to a series of dense layers, such as a series of six layers, including layers having 256 (with dropout), 128 (with dropout), 64, 32, 8 and 1 unit(s) with a sigmoid function as the final layer. An Adam optimizer with a learning rate of 1e−5 and batch size of 2048 may be computed for each model branch in parallel on a separate GPU for faster computation. Additional architectures may include (1) replacing the GAP layer with recurrent neural networks such as long short-term memory and gated recurrent units; (2) changing the number of convolutional layers with varying filter sizes in all or number of branches in the present architecture or in addition, changing the number of branches in the architecture; (3) addition of derived signals from the time-voltage traces such as power spectral densities to the model training; and (4) addition of tabular or derived features from EHR such as laboratory values, echo measurements, ICD codes, and/or care gaps in addition to age and sex. In one example, demographic data 416 and patient data 1304 may be supplemented with these additional tabular or derived features from the EHR of the subject.

Training Method

The training data may be divided into a plurality of folds with a last fold set aside as a validation set. An exemplary distribution may include five folds with five percent of the training data set aside as a validation set. The data may be split such that the same patient is not in both training and testing sets for cross-validation. The outcomes may be approximately balanced in the validation set. Training timing may be based upon validation loss which may be evaluated upon each training interval. Evaluated loss (binary cross-entropy) on the validation set for each epoch may be sufficient as a criteria. For example, training may be terminated if the validation loss fails to decrease for 10 epochs (as an early-stopping criteria), and the maximum number of epochs may be set to 500. An exemplary model may be implemented using Keras with a TensorFlow backend in python and default training parameters may be used. In other embodiments, other models, programming languages, and parameters may be used. If all leads are sampled for a single common time period (e.g., twelve leads sampled from 0-10 seconds), then a single branch of the abovementioned model may be used. Demographic variables may be added to the model to boost robustness and improve predictions. As an example, demographic variables of age and sex may be added to the model by concatenating with the other branches a 64 hidden unit layer following. In one example training may be performed on an NVIDIA DGX1 platform with eight V100 GPUs and 32 GB of RAM per GPU. Training, however, may be performed via any computing devices, CPUs, GPUs, FPGAs, ASICs, and the like with variations in duration based upon the available computer power available at each training device. In on example, fitting a fold on 5 GPUs and each epoch took approximately 10 minutes.

For additional external validation, it may be advantageous to utilize data acquired at a certain hospital or other provider for training, and then test the model on all data acquired at the other hospitals/other providers. Segmenting training and validation sets by institutions allows formation of an additional independent validation of model accuracy.

Model Operation

Once a model is sufficiently trained, the model may be used to predict one or more status associated with a patient based on the patient's ECG. As such, inputs to the trained model include, at a minimum, an ECG. The model's accuracy may be increased, and as such add additional utility (with the capability to recommend treatment changes) by having additional clinical variable inputs as described in detail above.

Outputs of the trained model may include the likelihood of a future adverse outcome (potential outcomes are listed in detail above) and potential interventions that may be performed to reduce the likelihood of the adverse outcome. An exemplary intervention that may be suggested includes notifying the attending physician that if a patient receives a beta blocker medication, their risk of hospitalization may decrease from 10% to 5%.

Generating predictions from these models may include satisfying an objective to determine the future risk of an adverse clinical outcome, in order to ultimately assist clinicians and patients with earlier treatment and potentially even prevention as a result of the earlier intervention. The duration between the ECG and the ultimate prediction (for example 1 year in the case of predicting 1-year mortality) may vary depending on the clinical outcome of interest and the intervention that may ultimately be suggested and/or performed. As references above, the models may be trained for any relevant time duration after the ECG acquisition, such as a period of time including 1, 2, 3, 4 or 5 years (or more), and for any relevant clinical prediction. Additionally, for each relevant clinical prediction, an intervention may be similarly suggested based upon either a model learned correlation, or publications of interventions. An example may include predicting that a patient has a 40% chance of a-fib in the next year; however, if the patient is prescribed (and takes) a beta blocker, that same patient may instead have a reduced, 20% chance of developing a-fib in the next year. Incorporating precision medicine at the earliest stages in treatment, such as when the patient incurs a first ECG, allows treating physicians to make recommendations that may improve the patient's overall quality of life and prevent unfavorable outcomes before the patient's health deteriorates to the point where they seek advanced medical treatment. Furthermore, by incorporating additional variables above and beyond the ECG into the training phase of development, the models will learn how certain treatments/interventions can positively impact patient outcomes, so as to reduce the chance of the adverse clinical outcome of interest. During the operation phase, the model can ingest the ECG and any relevant clinical variable inputs and then output predicted likelihood of the adverse clinical outcome either without or with certain treatments/interventions. Even if the patient's current treatments are unknown, the model can make suggestions such as: "If this patient happens to be diabetic, then their chance of 1-year mortality is reduced by 10% if their blood glucose is adequately controlled according to clinical guidelines."

Additional Exemplary Model Operations

In one embodiment, a sufficiently trained model may predict likelihood of Afib and include a further suggestion, based upon the patient's height, weight, or BMI, that weight loss is needed to improve the patient's overall response to therapy. A sufficiently trained model may include a model that ingests a PDF of a clinically-acquired 12-lead resting ECG and outputs the precise risk of mortality at 1 year as a likelihood ranging from 0 to 1 where the model also received a patient height, weight, or BMI and the patient's clinical updates over the course of at least a year.

Figures 19A, 19B:
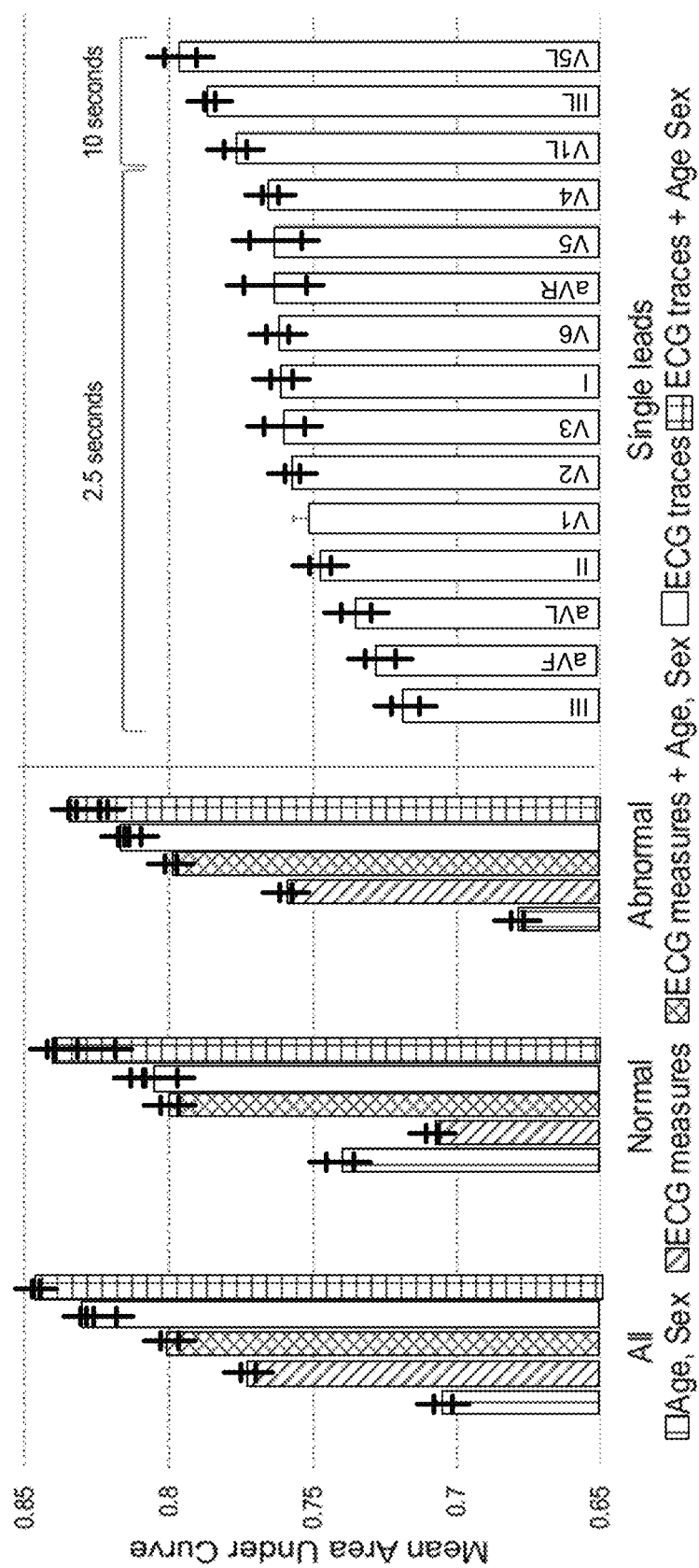
FIG. 19A is a graph of area under a receiver operating characteristic curve (AUC) for predicting 1-year all-cause mortality.
FIG. 19B is a bar graph indicating the AUC for various lead locations derived from 2.5-second or 10-second tracings.

FIG. 19A is a graph of area under a receiver operating characteristic curve (AUC) for predicting 1-year all-cause mortality. FIG. 19B is a bar graph indicating the AUC for various lead locations derived from 2.5-second or 10-second tracings.

Using the inclusion/exclusion criteria described above and a 5-fold cross-validation scheme, it may be demonstrated that the area under the receiver operating characteristic curve (AUC) for predicting 1-year all-cause mortality is 0.830 using the ECG voltage-time traces alone (taken directly from the PDF) and improved to 0.847 when age and sex were added as additional input variables (see the far-right bars in each grouping in FIG. 19A). Note that AUC is a measure of model accuracy that ranges from 0.5 (worst predictive accuracy equivalent to random chance) to 1 (perfect prediction). During a 12-lead ECG acquisition, all leads are acquired for a duration of 2.5 seconds and three of those 12-leads (V1, II and V5) are additionally acquired for a duration of 10 seconds. The model with all 15 ECG voltage-time traces from the 12 standard leads together (3 leads acquired for 2.5 seconds plus 12-leads acquired for 10 seconds) provided the best AUC compared to models derived from each single lead as input. Models derived from the 10-second tracings had higher AUCs than the models derived from the 2.5-second tracings, demonstrating that a longer duration of data provides more informative features to the model.

Figure 20B:
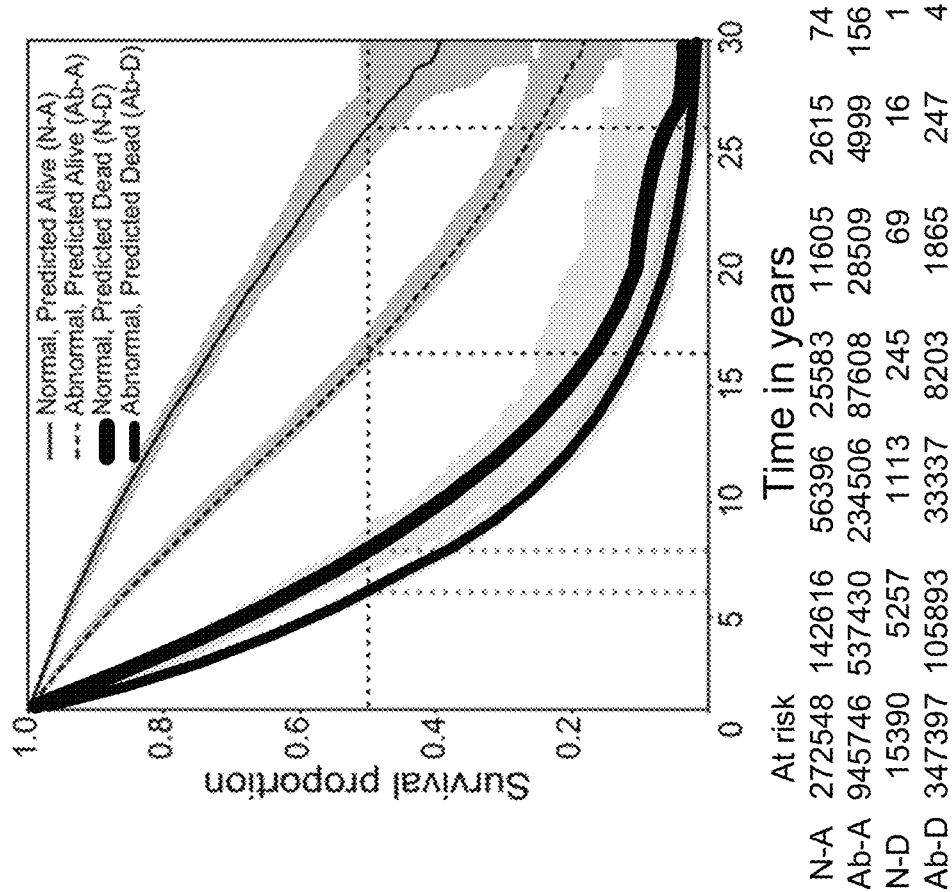
FIG. 20B is a Kaplan-Meier survival analysis plot of survival proportion vs. time in years at a chose operating point (likelihood threshold=0.5; sensitivity: 0.76; specificity: 0.77)
Figure 20A:
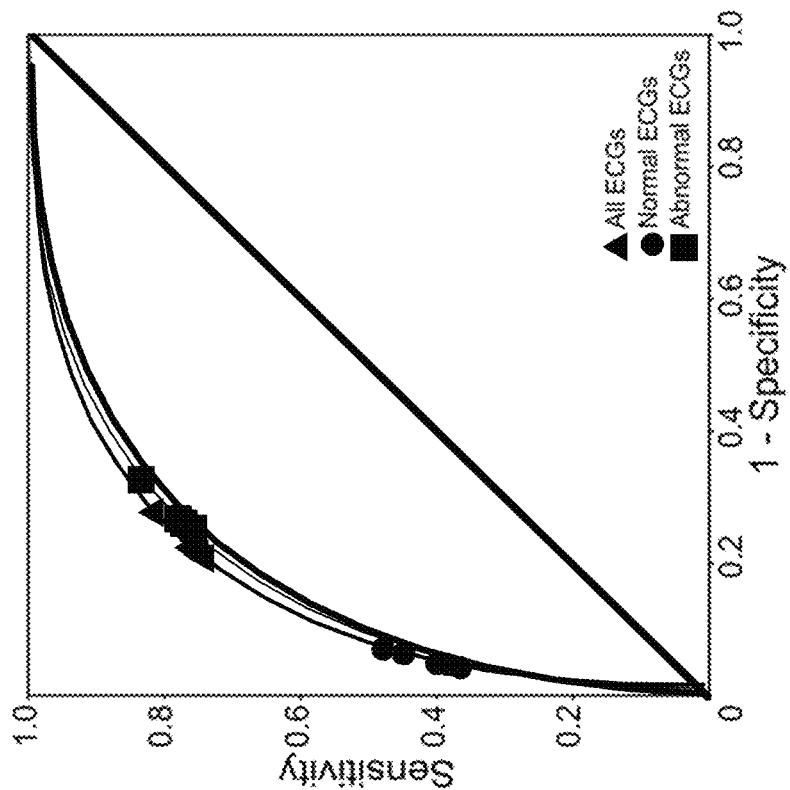
FIG. 20A is a plot of ECG sensitivity vs. specificity.

FIG. 20A is a plot of ECG sensitivity vs. specificity. FIG. 20B is a Kaplan-Meier survival analysis plot of survival proportion vs. time in years at a chose operating point (likelihood threshold=0.5; sensitivity: 0.76; specificity: 0.77);

To further investigate predictive performance within the overall dataset and the subsets of ECGs interpreted as either "normal" or "abnormal" by a physician, Kaplan-Meier survival analysis was performed using follow-up data available in the EHR for the two groups predicted by the model (alive/dead in 1-year) at the chosen operating point (likelihood threshold=0.5; sensitivity: 0.76; specificity: 0.77). For normal ECGs, the median survival times (for the mean survival curves of five-folds) of the two groups predicted alive and dead at 1-year were 26 and 8 years, respectively, and for abnormal ECGs, 16 and 6 years, respectively (see FIG. 20B). A Cox Proportional Hazard regression model was fit for each of the five folds and mean hazard ratios (with lower and upper bounds of 95% confidence intervals) were: 4.4 [4.0-4.5] in all ECGs, 3.9 [3.6-4.0] in abnormal ECGs and 6.6 [5.8-7.6] in normal ECGs (all p<0.005) comparing those predicted by the model to be alive versus dead at 1-year post-ECG. Thus, the hazard ratio was largest in the subset of normal ECGs, and the prediction of 1-year mortality from the model was a significant discriminator of long-term survival for 30 years after the clinical acquisition of the ECG.

Figure 21:
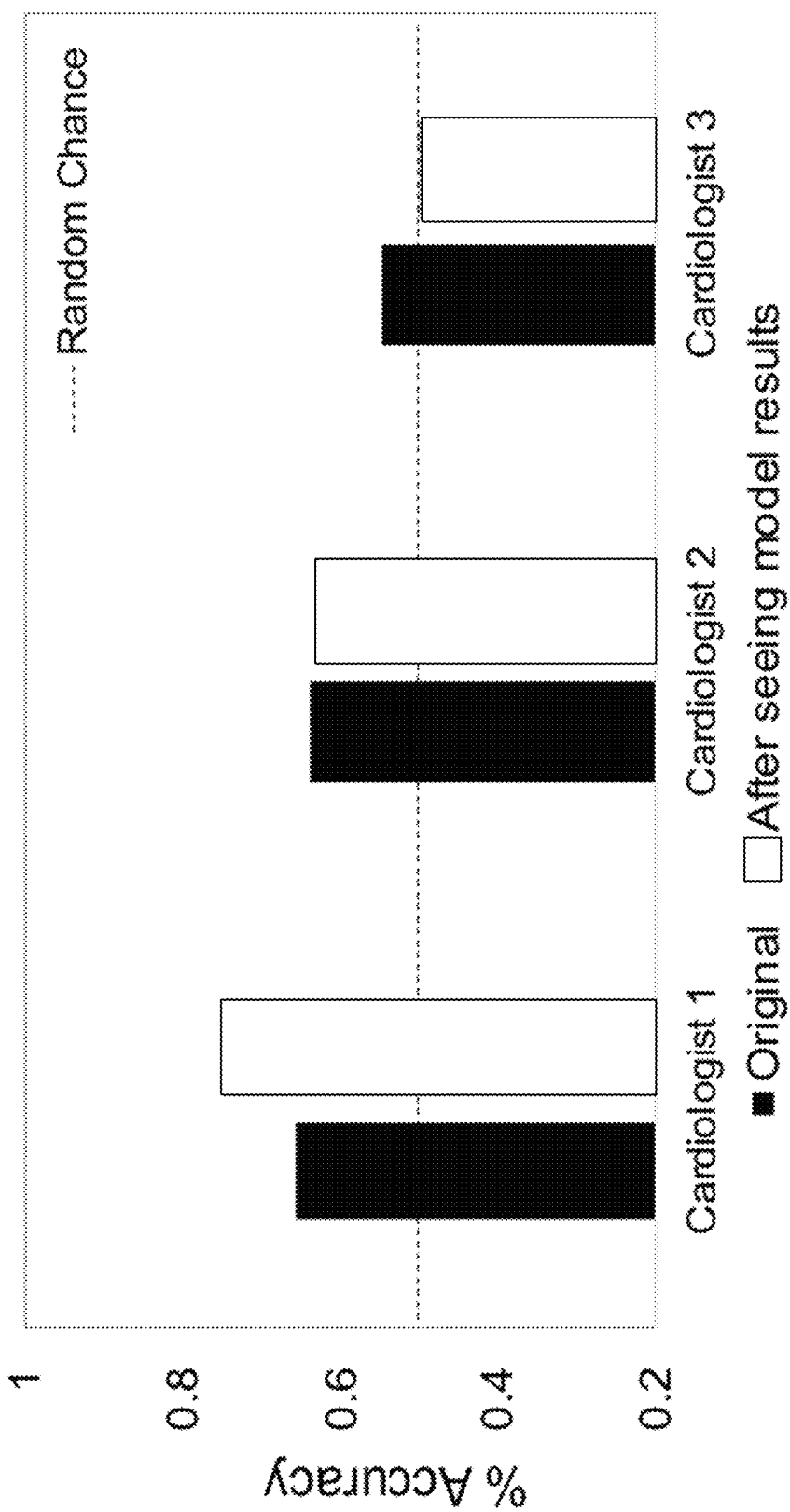
FIG. 21 is a graph of predicted mortality outcomes by three different cardiologists before and after seeing model results.
Figure 22A:
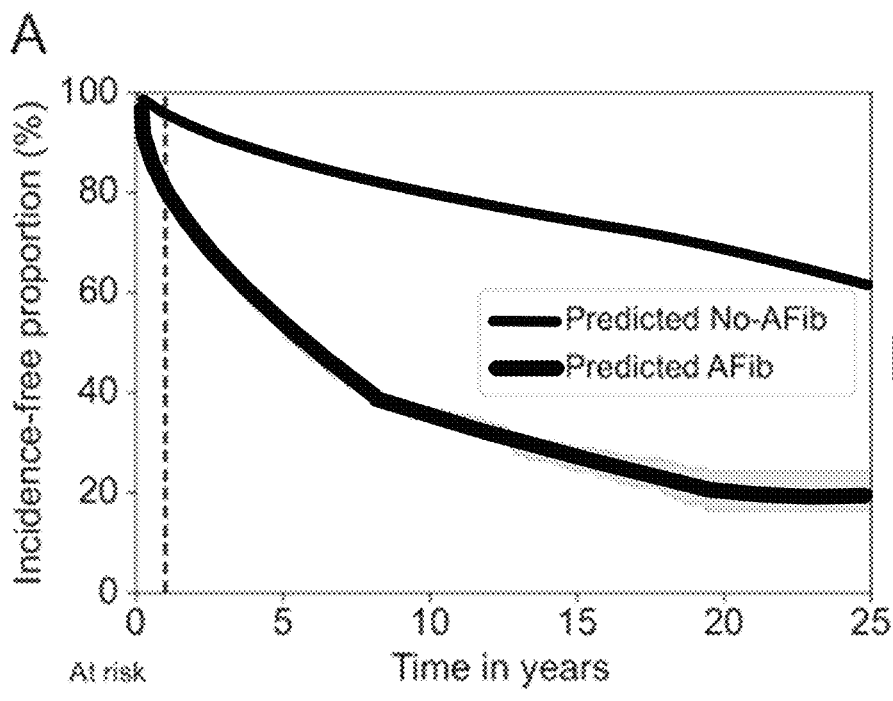
FIG. 22A is a graph of incidence-free proportion vs. time in years.
Figure 22B:
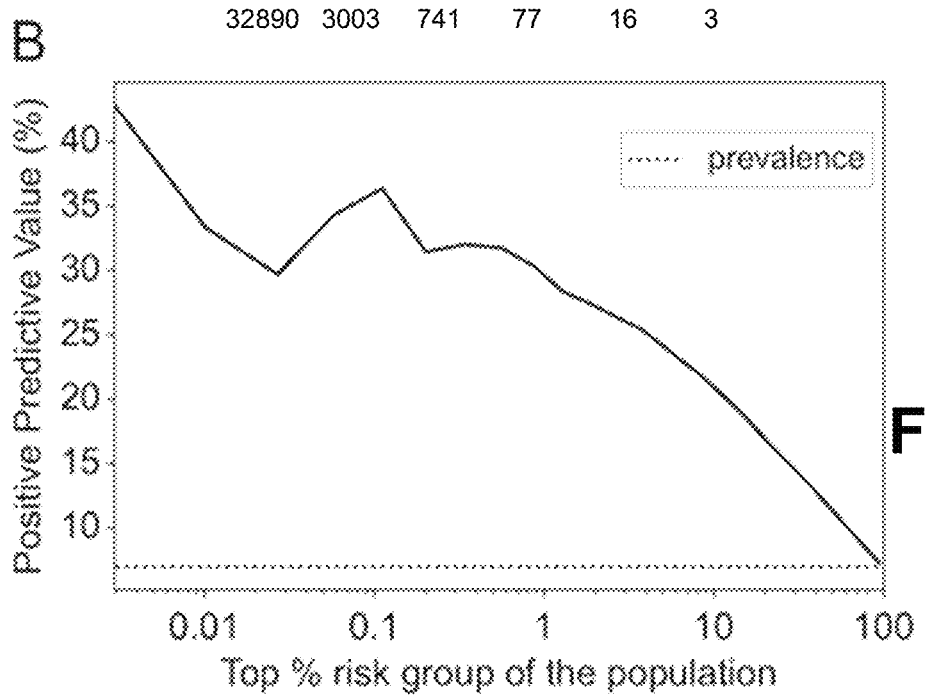
FIG. 22B is a graph of positive predictive value vs. top percentage risk group of a population.

FIG. 21 is a graph of predicted mortality outcomes by three different cardiologists before and after seeing model results. Another consideration of a sufficiently trained model may include if the features learned by the model are visually apparent to cardiologists. For example, if four hundred and one sets of paired normal ECGs are selected and provided to a blinded survey with three cardiologists, a measure of model performance against cardiologist visual inspection may be generated. Each pair may consist of a true positive (normal ECG correctly predicted by the model as dead at one year) and a true negative (normal ECG correctly predicted by the model as alive at one year), matched for age and sex. FIG. 22A is a graph of incidence-free proportion vs. time in years. FIG. 22B is a graph of positive predictive value vs. top percentage risk group of a population. In one study cardiologists generally had poor accuracy of 55-68% (10-36% above random chance) to correctly identify the normal ECG linked to 1-year mortality. After allowing each cardiologist to study a separate dataset of 240 paired ECGs labeled to show the outcome, their prediction accuracy in repeating the original blinded survey of 401 paired ECGs remained low (50-75% accuracy or 0-50% above random chance) (see FIG. 21). This suggests that the above models are able to identify features predictive of important clinical outcomes that, importantly, cardiologists are not able to visually identify despite many years of clinical training.

Note that the reported accuracies for predicting outcomes can likely be slightly improved by testing against only a single ECG from each patient. The above numbers report test data accuracies (AUCs) from all ECGs from a patient, which ends up over-weighting patients who receive more ECGs (patients who receive 20 ECGs in a lifetime contribute more to the assessment of accuracy than a patient who only received 1 ECG in his/her lifetime). Since patients who have more ECGs are typically sicker, it is more difficult to predict their clinical outcomes and thus over-weighting those patients can slightly reduce the perceived accuracies (AUCs).

Prediction of Atrial fibrillation

Atrial fibrillation (AF) is an abnormal rhythm in the heart that increases the risk of stroke. Predictive strategies for detecting the onset of AF, before stroke occurs, are therefore highly clinically important. In one embodiment, a deep learning model may predict future AF directly from 12-lead resting electrocardiogram (ECG) voltage-time traces as extracted from a clinically-acquired PDF.

For example, a dataset including 2.7 million clinically-acquired 12-lead ECGs, may include 1.1 million ECGs without AF (from 237,060 patients). The presence or absence of future incident AF may be determined via subsequent ECG studies and problem list diagnoses in the electronic health record. The prevalence of incident AF was 7% in the entire population and 3% in a subset of 61,142 patients with ECGs clinically interpreted as normal. A model, such as a multi-class deep convolutional neural network using 5-fold cross-validation, may be trained to predict 1-year incident AF with 15 ECG traces as input. In one instance, model performance may be measured from the area under the receiver operating characteristic curve (AUC) and Cox Proportional Hazard analysis on incidence-free curves of the predicted groups. Additional evaluation of model performance may be performed in the context of opportunistic population screening. For example, the positive predictive value (PPV) of the model as a function of the number of patients with highest model-predicted risk to be screened may be calculated. In the multi-class deep CNN with 15 ECG traces as input instance, the mean AUC of the predictive model was 0.75 and patients predicted to develop AF within the next year had a significant long-term increased risk for developing AF that extended over 25 years after the ECG acquisition (see FIG. 22A). Even in the subset of ECGs interpreted as 'normal' by a physician, the AUC was 0.720. In the setting of potential population screening, this performance corresponded to a positive predictive value of 0.3 for screening the highest 1% at risk (see FIG. 22B). This means that, of the top 1% at risk, approximately 30% will end up developing AF within the first year, and many more will develop AF over the next 25 years.

In summary, this is another example of using a model to predict the onset of a future clinically relevant event (atrial fibrillation within the next year). This prediction maintains modest accuracy even when the ECG is clinically interpreted as 'normal' by a physician. Providing predictions to the physician, especially in instances where the physician's 'normal' clinical interpretation of the ECG occurs, will greatly improve patient care. The predictive and therapeutic implications of the model may be even further improved with the inclusion of additional features to the training phase of the model development, allowing even further relevant predictions about how treatments/interventions reduce the risk of developing AF (for example, if a patient is taking a beta-blocker medication or has his/her blood pressure within a normal range it will likely reduce the risk of developing AF, and the model can make these predictions) may be included in a patient's treatment.

In some embodiments, the results reported by model 400 reflect detection of paroxysmal AF and prediction of incident AF. Intuitively, the characteristics of the ECG that lead to a high-risk prediction by the DNN will be more prevalent in patients who already have AF but are currently in sinus rhythm. With this in mind a higher model performance for identification of paroxysmal AF compared to prediction of incident AF was expected, and this is exactly what was seen. A declining rate of new onset AF over the course of one year also was expected. This is seen in FIG. 7L and is consistent with rapid identification of paroxysmal AF followed by a slower identification of cases that represent incident AF. The largest piece of evidence supporting the assertion that the DNN model can predict incident AF is the continued separation of the KM incidence-free survival curves up to thirty years after the index ECG as noted in FIGS. 7E through 7K. In other embodiments, the results from model 400 may reflect structural changes that occur in the atria of patients with AF, such that the model 400 uses ECG manifestations of this atrial myopathy to guide the predictive results it provides.

There are many different settings in which the system 100 may be utilized and the methods disclosed herein may be performed. With regard to setting, one promising opportunity—particularly for integrated care delivery systems—is the systematic screening of all ECGs in a health system. For example, the model 400 could be incorporated into an existing clinical workflow (such as through an EHR system) such that every ECG is evaluated, and high-risk studies could be flagged for follow-up and surveillance. Such increased surveillance could take many different forms, including systematic pulse palpation, systematic ECG screening, continuous patch monitors worn once or multiple times, intermittent home screening with a device such as Kardia mobile, or wearable monitors such as the Apple Watch.

APPENDIX A

```
CODE: (Method of reading ECG)
def convert_pdf_to_svg(fname, outname, verbose=0):
'''
Input:
    fname : PDF file name
    outname : SVG file name
Output:
    outname : return outname (file saved to disk)
This will convert PDF into SVG format and save it in the given outpath.
'''
(status, out) = subprocess.getstatusoutput(''.join(['pdftocairo -svg', fname,' ', outname]))
if (status != 0):
 logging. error('Error in converting PDF to SVG: { }'.format(out))
return outname
def process_svg_to_pd_perdata(svgfile, pdffile=None):
'''
Input:
svgfile - datapath for svg file
Output (returns):
data : data for 12 leads(available 15 or 12 traces), scale_vales and resolution units in a pandas
dataframe
Hard coded values :
1) length of signal = 6 is assumed to be the calibration tracing at the beginning of the
trace (by experiment)
'''
columnnames = np.array(['I', 'II','III','aVR',',','aVF',',','V2','V3','V4', \
    'V5', 'V6', 'VIL','IIL','V5L'])
doc = parse(svgfile)
if pdffile is None:
  strn = os.path.splitext(os.path.basename(svgfile))[0]
else:
  strn = os.path.splitext(os.path.basename(pdffile))[0]
arrayindex = [np.array([strn, strn]), np.array(['x','y'])]
data    =    pd.DataFrame(columns    =    ['PT_MRN','TEST_ID','filename','lead','x','y'])
#,'scale_x','scale_y'])
a = 0
spacingvals = [ ]
scale_vals = [ ]
try:
  siglen = [ ]
  for path in doc.getElementsByTagName('path'):
    tmp = path.getAttribute('d')
    tmp split = tmp.split(' ')
signal np = np.asarray([float(x) for x in tmp_split if (x != 'M' and x != 'L' and x != 'C' and x != 'Z' and x !=''))
  signalx = signal_np[0::2]
  signaly = signal_np[1::2]
  siglen. append(len(signalx))
siglen = np.array(siglen)
# these are the calibration signals
cali6sigs = np.where(siglen == 6)[0]
minposcali = np.min(cali6sigs)
  tmpstart = list(range(minposcali, len(siglen)))
last15sigs = np.array(list(set(tmpstart)- set(cali6sigs)))
# index for leads
a = 0
```

APPENDIX A-continued

```
for ind, path in enumerate(doc.getElementsByTagName('path')):
 if ind in last15sigs:
   if a > 14:
     continue
   tmp = path.getAttribute('d')
   tmp split = tmp.split(' ')
   signal np = np.asarray([float(x) for x in tmp split if (x != 'M' and x != 'L' and x != 'C' and x !=
'Z' and x !='')])
   signalx = signal_np[0::2]
   signaly = signal_np[1::2]
   # expect the name of the file to be ptmrn_testid format.
   tmp = strn.split('_')
   try:
     pid, testid = tmp[0], tmp[1]
   except:
     pid = tmp[0]
     testid = tmp[0]
   data.loc[data.shape[0]] = [pid, testid, strn, columnnames [a], signalx, signaly]
   spacingx = [t -s for s,t in zip(signalx, signalx[1:])]
   spacingvals.append(np.min(spacingx))
   a += 1
 elif ind in cali6sigs:
   tmp = path.getAttribute('d')
   tmp split = tmp.split(' ')
   signal np = np.asarray([float(x) for x in tmp split if (x != 'M' and x != 'L' and x != 'C' and x !
=
'Z' and x != ' ')])
   signalx = signal_np[0::2]
   signaly = signal_np[1::2]
   scale_vals.append([np.min(signaly), np.max(signaly)])
 if len(scale_vals) == 0:
   data = None
   return data
 sx = [x[0] for x in scale_vals]
 sy = [x[1] for x in scale_vals]
 startloc = [d[0] for d in data.x.values]
 leadsip = len(startloc)
 a = np.sum(startloc[0:3] == startloc[0])
 b = np.sum(startloc[3:6] == startloc[3])
 c = np.sum(startloc[6:9] == startloc[6])
 d = np.sum(startloc[9:12] == startloc[9])
 if data.shape[0] ==15:
   e = np.sum(startloc[12:15] == startloc[12])
   checkrhs = [3,3,3,3,3]
   checklhs = [a,b,c,d,e]
   assert checklhs == checkrhs
   scale_x= [sx[0:3],sx[0:3],sx[0:3],sx[0:3], sx[3:6]]
   scale y = [sy[0:3],sy[0:3],sy[0:3],sy[0:3], sy[3:6]]
 elif data.shape[O] ==12:
   checkrhs = [3,3,3,3]
   checklhs = [a,b,c,d]
   assert checklhs == checkrhs
   scale_x = [sx[0:3],sx[0:3],sx[0:3],sx[0:3]]
   scale y = [sy[0:3],sy[0:3],sy[0:3],sy[0:3]]
 else:
   data=None
   return data
 scale x = [y for x in scale x for y in x]
 data['scale_x'] = scale_x[0:data.shape[0]]
 scale_y = [y for x in scale_y for y in x]
 data['scale_y'] = scale_y[0:data.shape[0]]
 data['minspacing'] = spacingvals[0:data.shape[0]]
except:
 data = None
return data
```

Thus, a properly trained deep neural network can predict incident AF directly from 12-lead ECG traces, even when the ECG is clinically interpreted as "normal". This approach has significant potential for targeted screening and monitoring of new onset AF to potentially minimize the risk of stroke.

In addition, deep learning can be a powerful tool for identifying patients with potential adverse outcomes (e.g., death) who may benefit from early interventions, even in cases interpreted as "normal" by physicians.

In one embodiment, systems and methods described herein for prediction of atrial fibrillation from an ECG may further be adapted to predict other cardiac events from received ECG data. For example, of the received ECG data, measurements may record abnormal variations which are meaningful in additional cardiac event analytics. The QT interval is one such measurement made on an ECG used to assess some of the electrical properties of the heart. It is calculated as the time from the start of the Q wave to the end of the T wave, and approximates to the time taken from when the cardiac ventricles start to contract to when they finish relaxing. An abnormally long or abnormally short QT interval is associated with an increased risk of developing abnormal heart rhythms and sudden cardiac death. Abnormalities in the QT interval can be caused by genetic conditions such as long QT syndrome, by certain medications such as sotalol or pitolisant, by disturbances in the concentrations of certain salts within the blood such as hypokalaemia, by hormonal imbalances such as hypothyroidism, or they may be induced by certain medications. QT prolongation is a measure of delayed ventricular repolarization. Excessive QT prolongation can predispose the myocardium to the development of early after-depolarisations, which in turn can trigger re-entrant tachycardias such as torsades de pointes (TdP). Although the relationship between QT interval duration and the risk of TdP is not fully understood, a corrected QT interval (QTc) of >500 ms or an increase in the QTc of >60 ms may be considered to confer a high risk of TdP in an individual patient. Prolongation of the corrected QT (QTc) interval becomes an even further concern, for example, with patients who receive psychotropic medications. Such patients may have baseline clinical risk factors for QTc prolongation, and many psychotropic medications may further prolong this interval. Analytics may identify over 200 medications having known or suspected association with QTc prolongation (LQT), which can lead to the rare but potentially catastrophic event, TdP.

Models herein generate predictions based upon the combination of ECG data, patient age, and patient sex, although it will be appreciated that models may be generated by combining ECG data with other or additional demographic data or EHR-derived patient data. Prediction of drug-induced LQT using an ECG-based machine learning model is feasible and may outperform a model trained on baseline QTc, age, and sex alone. In one example, ECG inputs having a baseline 12-lead ECGs with QTc values <500 ms for patients who had not received any known, conditional, or possible QTc prolonging medication at the time of ECG or within the past 90 days may be matched with ECGs from the same patients while they were taking at least one drug ("on-drug" ECGs), such as one of the over 200 medications having known or suspected associations with LQT. Features from the ECG as a whole may be considered in addition to the presence of abnormal QTc features for each respective patient.

Training may include using 5-fold cross-validation on a plurality of models such as two machine learning models using the baseline ECGs of approximately 92,848 resulting pairs to predict drug-induced LQT (≥500 ms) in the on-drug ECGs. Artificial intelligence engines may be implemented, including, by example, a deep neural network using ECG voltage data and a gradient-boosted tree using the baseline QTc with age and sex as additional inputs to both models. Other models may include one or more inputs as described herein. Other combinations of folds, hold-out patients, validations, and number of models for comparison may be considered without departing from the methodology as described herein.

In one such training on an available patient dataset having paired ECG data for patients with both an off-drug ECG and an on-drug ECG, on-drug LQT prevalence was 16%. The ECG model demonstrated superior performance in predicting on-drug LQT (area under the receiver operating characteristic curve (AUC)=0.756) compared to the QTc model (0.710). At a potential operating point such as depicted in FIG. 23, the ECG model had 89% sensitivity and 95% negative predictive value. Even in the subset of patients with baseline QTc <470/480 ms (male/female; post-drug LQT prevalence=14%), the ECG model demonstrated good performance (AUC=0.736). An ECG-based machine learning model can stratify patients by risk of developing drug induced LQT better than a model using baseline QTc alone. This model may have clinical value to identify high-risk drug starts that would benefit from closer monitoring and others who are at low risk of drug induced LQT.

Patients having been identified as high risk for drug-induced LQT may then be reported to their respective physicians for additional monitoring, potential therapy and treatment modifications, or other risk-reduction steps as determined by the physician. In one example, the reporting may include additional risk-reduction steps based upon one or more personal characteristics of the patient, the patient's medical history, the patient's ECG, or publications identified as being pertinent to the patient based upon available data. In another embodiment, the high-risk identification may be generated real-time from the ECG equipment itself based upon the ongoing ECG and the patient characteristics uploaded to the equipment either manually by diagnostic personnel or retrieved from the patient's EMR linked to the ECG equipment.

For systems, methods, and devices described herein, additional cardiac events may be considered for modeling and/or predictions independently or together with Afib. In one example, a composite model architecture may be considered which provides an architecture for each cardiac event prediction that a composite model system may operate.

Composite Model

A system and method for generating and applying a composite model is disclosed herein. In some embodiments, the composite model is an ECG-based machine-learning composite model. In some embodiments, the composite model can predict a composite heart disease endpoint or cardiac event. In some embodiments, a composite model yields a higher positive outcome metric, such as a positive predictive value (PPV), to facilitate more practical recommendation of echocardiography to improve under-diagnosis of heart disease. In some embodiments, the composite model comprises an electrocardiogram (ECG)-based machine learning approach to predict multiple heart disease endpoints simultaneously.

A composite model may be used, for example, to identify high-risk patients. The composite model may use data more ubiquitously available than transthoracic echocardiograms (TTEs), such as 12-lead electrocardiograms (ECGs). ECGs are far more common, inexpensive, and performed for a much broader range of indications, including on asymptomatic patients (for example in the preoperative setting). The composite model may thus serve as a screening tool such that patients identified as high risk could be referred for diagnostic TTE.

In some embodiments, the composite model may be used to identify patients at high risk for any one of numerous heart disease endpoints within a single ECG platform, including moderate or severe valvular disease (aortic stenosis [AS], aortic regurgitation [AR], mitral stenosis [M5], mitral regurgitation [MR], tricuspid regurgitation [TR]), reduced left ventricular ejection fraction [EF], and increased interventricular septal [IVS] thickness. The composite model may generate a composite prediction with higher yield/PPV that would facilitate a more practical clinical recommendation for follow-up diagnostic echocardiography.

Clinically, a composite model can enable targeted TTE screening to help detect unrecognized and underdiagnosed diseases. A composite model may have both high sensitivity and precision. The composite model can help guide the decision to obtain a TTE even for asymptomatic patients, shifting the balance to a scenario where TTE can be effective as a screening tool downstream of an ECG, and helping clinicians diagnose patients at the right time to prevent downstream adverse events, optimize the timing of interventions, and better implement evidence-based monitoring or management.

A machine-learning composite model using only ECG-based inputs can predict multiple important cardiac endpoints within a single platform with both good performance and high PPV, thereby representing a practical tool with which to better target TTE to detect undiagnosed disease. As shown in Example 1, below, an exemplary composite model is described and confirmatory results through retrospective real-world deployment scenarios are provided, to show the large impact that such a model can have on patients when deployed across a health system. These approaches to both clinical predictions and simulated deployment represent practical solutions for existing limitations in the implementation of machine learning in healthcare.

In some embodiments, the machine learning composite model may be trained to predict composite echocardiography-confirmed disease within a certain period of time. For example, the composite model may be trained to predict composite disease within 1 year. In some embodiments, the machine learning composite model may be trained to predict 2, 3, 4, 5, 6, 7, or more diseases. For example, an exemplary composite model may be trained to predict moderate or severe valvular disease. As another example, a composite model may be trained to predict one or more of aortic stenosis, aortic regurgitation, mitral stenosis, mitral regurgitation, tricuspid regurgitation, abnormally reduced ejection fraction, and abnormal interventricular septal thickness.

A composite model may be employed as part of a system described, for instance, in U.S. Patent Publication No. 2021/0076960, titled ECG Based Future Atrial Fibrillation Predictor Systems and Methods, the contents of which are incorporated herein by reference in their entirety for all purposes.

Example 1

In one example, an ECG-based cardiovascular disease detection system may employ a machine-learning platform comprising a composite model which can effectively predict clinically significant valvular disease, reduced left ventricular EF, and increased septal thickness with excellent performance (AUROC 91.4%) by using only ECG traces, age, and sex. Furthermore, the combination of these distinct endpoints into a single platform tied to a recommendation for a singular, practical clinical response—follow-up echocardiography—resulted in an overall PPV of 52.2% for a clinically meaningful disease while maintaining high sensitivity (90%) and specificity (75.5%). This novel approach of combining multiple endpoints which align in the same recommended clinical action enables the model to leverage the increased prevalence and probability of any one disease state occurring to improve our predictive performance for potential clinical implementation.

Moreover, this approach may have potential clinical utility in a retrospective deployment scenario. In one example, a retrospective deployment scenario was trained on data pre-existing relative to a first point in time (e.g., data prior to 2010 until some data endpoint) and deployed on all patients without prior disease who obtained an ECG in 2010, maintaining similarly high performance as compared to the main cross-validation results based only on passive observation and standard clinical care. With an active deployment of the present platform, even higher yields/PPV may be achieved once clinicians can pursue active intervention in the form of follow-up TTE or more detailed history-taking and physical examination based on the model.

Using 2,141,366 ECGs linked to structured echocardiography and electronic health record data from 461,466 adults, a machine learning composite model was trained to predict composite echocardiography-confirmed disease within 1 year. Seven exemplary diseases were included in the composite label: moderate or severe valvular disease (aortic stenosis or regurgitation, mitral stenosis (MS) or regurgitation, tricuspid regurgitation), reduced ejection fraction (EF) <50%, or interventricular septal thickness >15 mm. In other examples, the model may be trained to predict other echocardiography-confirmed diseases, and other clinical thresholds besides 50% for abnormal reduced ejection fraction or 15 mm for abnormal interventricular septal thickness may be used. Composite model performance was evaluated using both 5-fold cross-validation and a simulated retrospective deployment scenario. Various combinations of input variables (demographics, labs, structured ECG data, ECG traces) were also tested. The composite model with age, sex and ECG traces had an AUROC of 91.4% and a PPV of 52.2% at 90% sensitivity. Individual disease model PPVs were lower, ranging from 2.1% for MS to 41.3% for reduced EF. A simulated retrospective deployment model had an AUC of 88.8% on data trained pre-2010 and, when deployed on at-risk patients in 2010, identified 22% of patients as high-risk with a PPV of 40%. The AUROC for different variable inputs ranged from 84.7% to 93.2%.

Data was retrieved and processed from three clinical sources at a large regional US health system (a first entity), including 2,091,158 patients from the health system's electronic health record (EHR) (a first source), 568,802 TTEs from a second source, and 3,487,304 ECG traces from a third source. In another embodiment, it will be understood that data may be obtained from a plurality of sources related to a plurality of different or unrelated entities. From this data, all ECGs after a first point in time (e.g., 1984) from patients 18 years old, sampled at either 250 hz or 500 hz with at least 8 leads, and with a corresponding medical record from the first source were included. This intersection of the first and third sources yielded 2,884,264 ECGs from 623,354 patients.

Vitals, labs, and demographics as of the ECG acquisition time were also obtained. Table 4 lists inputs grouped by category, although it will be appreciated that the model may utilize one or more other inputs within the categories listed or within one or more other categories. Each input is shown with its units in parenthesis. The ECG findings were binary.

TABLE 4

| | List of inputs |
|---|---|
| Demographics and Vitals | Age (years), race (white/other), sex, smoke (ever), BMI (kg/m2), diastolic and systolic blood pressure (mmHg), heart rate (bpm), height (cm), weight (kg). |
| Labs | A1C (%), Bilirubin (mg/dl), BUN (mg/dl), Cholesterol (mg/dl), CKMB (ng/ml), Creatinine (mg/dl), CRP (mg/l), D dimer (mcg/ml FEU), Glucose (mg/dl), HDL (mg/dl), Hemoglobin (g/dl), LDH (u/l), LDL (mg/dl), Lymphocytes (%), Potassium (mmol/l), PRO BNP (pg/ml), Sodium (mmol/l), Troponin I and T (ng/ml), Triglyceride (mg/dl), Uric acid (mg/dl), VLDL (mg/dl), eGFR (ml/min/1.73 m$^2$) |
| ECG findings | Acute MI, Afib, Aflutter, Complete Block, Early rep, Fas block, First deg block, Intrav Block, In Lbbb, In rbbb, Ischemia, Lad, Lbbb, Low QRS, LVH, Non-spec ST, Non-spec T, Normal, Other Brady, PAC, Pacemaker, Poor tracing, Prior infarct, Prior MI anterior, Prolonged QT, PVC, RAD, RBBB, Sec deg block, Sinus Brady, SVT, Tachy, T Inversion, Vtach |
| ECG measurements | Avg RR interval (ms), PR interval (ms), P axis, QRS duration (ms), QT (ms), QTC (ms), R axis, T axis, Ventricular rate (bpm) |

The closest past measurement to the ECG was used unless the measurement was older than a year, in which case a missing value was assigned. TTE measurements and diagnoses (AS, AR, MR, MS, and TR) were extracted from reports from the second source; and ECG structured findings, measurements, and 12-lead traces were extracted from the third source. ECGs were then labeled as detailed in the following sections, and ECGs without a label were discarded for all disease outcomes. Overall, 2,141,366 ECGs with at least 1 label from 461,466 patients were included (FIG. 24).

Figure 24:
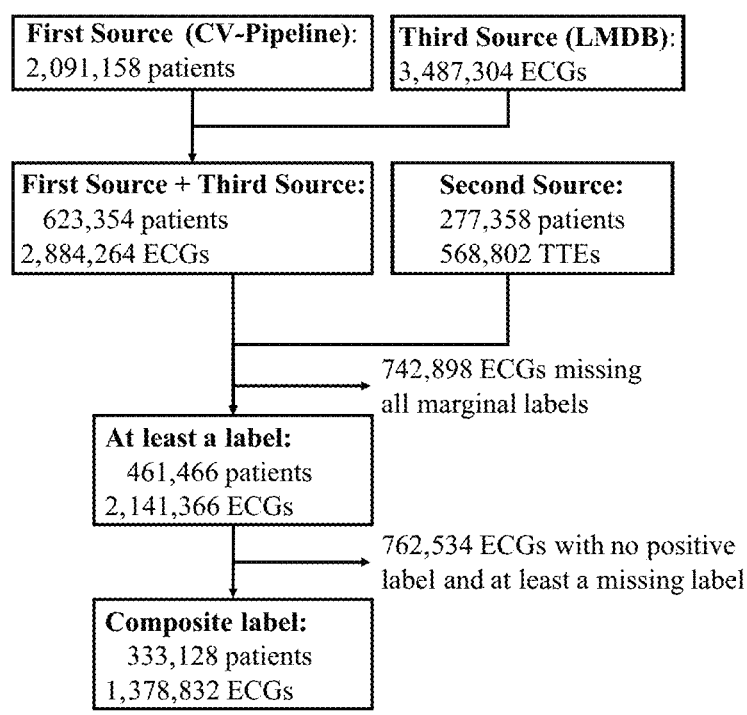
FIG. 24 displays a block diagram of source data to dataset.

Specifically, FIG. 24 displays a block diagram of source data to dataset used for experiments described in this patent. First source (EHR) data was processed into a cardiovascular pipeline to retrieve patients with physical encounters in the first entity health care system or that have records of an ECG or Echocardiography study. The clinical database of data from the third source was processed into a database, such as a lightning memory-mapped (LMDB) database, of ECGs sampled at either 250 hz or 500 hz, having at least 8 leads, having an acquisition date stamp later than 1984, coming from patients older than 18 years (as reported in the ECG), and with a cross-referenced medical record number (checked against an EHR processed list from the first source). The no-label ECGs refer to ECGs that did not meet any labeling criteria (AS, AR, MS, MR, TR, EF<50%, nor IVS>15 mm).

Labeling

TTE-Confirmed Disease Outcome Definitions

A plurality of outcome labels (e.g., 7 outcome labels) using TTE reports, one for each disease outcome of interest (AS, AR, MR, MS, TR, reduced EF, increased IVS thickness). String matching was used on the reports to identify the presence of valvular stenosis or regurgitation, as well as the associated severity level (Table 5). Specifically, Table 5 includes a keyword list for assigning an abnormality and severity to each valve in an Echocardiography report.

TABLE 5

| Abnormality | |
|---|---|
| Stenosis | stenosis, stenotic |
| Regurgitation | regurgitation, regurgitant, insufficiency |
| Severity | |
| Normal | absent, no stenosis, no AS, no MS, not stenotic, no PS, no tricuspid stenosis, no significant, no regurgitation, No TR, No MR, TS excluded, MS excluded, AS excluded, w/o stenosis, no mitral, no AR, trace, no evidence of, no pulmonic, no mitral, without aortic stenosis, stenosis is absent, no mitral regurgitation, physiologic, no hemodynamically, Normal 2-D, Normal MV, not sign, Normal structure and function, normal prosthetic, normal function, function normal, There is a normal amount of, is probably normal, is normal without |
| Mild | mild, valvular, aortic stenosis is present, valve stenosis is present, stenosis is possible, stenosis is possibly present, borderline |
| Moderate | moderate, Mod |
| Severe | severe, possibly, severe, moderate-severe, mod-severe, moderate-severe, moderately severe, moderate to severe, critical, consistent with significant |
| Valve | |
| Aortic | aortic, AS, AR, AV |
| Tricuspid | tricuspid, TR, TS, TV |
| Mitral | mitral, MR, MS, MV |

Each of 5 valvular conditions of interest were labeled as positive if moderate or severe and negative if reported normal or mild in severity, or a missing label was otherwise assigned.

Reduced EF was defined as a TTE-reported EF of <50%, and increased IVS thickness as >15 mm, although it will be appreciated that other ranges for EF and/or IVS thickness may be used to define reduced EF. TTEs not meeting those criteria were labeled as negative, and a missing label was assigned when the measurement was missing.

Outcome labels extracted from TTE reports for AS, AR, MR, MS, and TR were manually validated using chart review of 100-200 random samples where PPVs and NPVs of 98-100% were found.

ECG Labeling

Figure 25A:
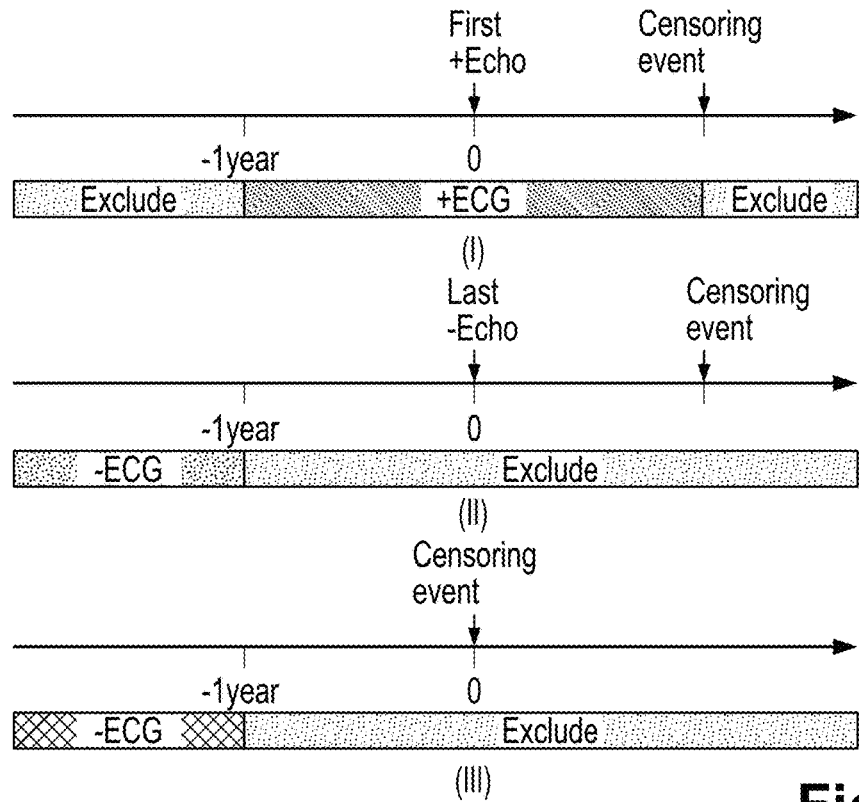
FIG. 25A displays a patient timeline used to label (I) positive ECGs, (II) confirmed negative ECGs, and (III) unconfirmed negative ECGs.

An ECG was labeled as positive for a given outcome if it was acquired up to a first time period, e.g., one year, before or any time after (up to a censoring event) the patient's first positive TTE report. An ECG was labeled as negative if it was acquired more than the first time period, e.g., one year prior to the last negative TTE or a censoring event without any prior positive TTEs (FIG. 25A). Specifically, FIG. 25A displays the patient timeline used to label (I) positive ECGs (+ECG in plot I), (II) confirmed negative ECGs (−ECG in plot II), and (III) unconfirmed negative ECGs (−ECG in plot III). The censoring event in plots I and II in FIG. 25A are any intervention that could modify the underlying physiology of the disease of interest. The last negative Echo ensures no record of prior positive Echo exists. The bottom timeline is used for patients that never got an Echo. The censoring event in plot III in FIG. 25A is defined as the last known patient encounter where physical presence is required.

Also, in the absence of any history of TTE, an ECG was also classified as negative if there was at least 1 year of subsequent follow-up without a censoring event and no coded diagnoses for the relevant disease (Table 6). Specifically, Table 6 lists ICD 10 codes used to search for evidence of diagnosis in ECGs from patients that never had an Echo. A negative label was assigned if none of the codes were ever present in the patient's chart.

TABLE 6

| Diagnosis | ICD10 codes |
| --- | --- |
| AS | I06.0, I06.2, I06.8, I06.9, I08.0, I08.2, I08.3, I08.8, I08.9, I35.0, I35.2, I35.8, I35.9, Z95.4, I33.*, Q20.*, Q21.*, Q22.*, Q23.*, Q24.* |
| AR | I06.I, I06.2, I06.8, I06.9, I08.0, I08.2, I08.3, I08.8, I08.9, I35.1, I35.2, I35.8, I35.9, Z95.4, I33.*, Q20.*, Q21.*, Q22.*, Q23.*, Q24.* |
| MR | I05.1, I05.2, I05.8, I05.9, I08.0, I08.1, I08.3, I08.8, I34.0, I34.1, I34.8, I34.9, Z95.4, I33.*, Q20.*, Q21.*, Q22.*, Q23.*, Q24.* |
| MS | I05.0, I05.2, I05.8, I05.9, I08.0, I08.1, I08.3, I08.8, I34.2, I34.8, I34.9, Z95.4, I33.*, Q20.*, Q21.*, Q22.*, Q23.*, Q24.* |
| TR | I07.I, I07.2, I07.8, I07.9, I08.1, I08.2, I08.3, I08.8, I36.1, I36.2, I36.8, I36.9, Z95.4, I33.*, Q20.*, Q21.*, Q22.*, Q23.*, Q24.* |
| EF <50% | I42.0, I42.6, I42.7, I42.8, I42.9, T86.2, T86.3, Z94.1, Z94.3, I09.81, I97.13, I25.5, B33.2, O90.3, I43.*, I50.*, I51.8* |
| IVS >15 mm | I37.1, I37.2, Z95.4, E83.11, I10.*, I11.*, I12.*, I13.*, I15.*, I16.*, E85.*, I42.1*, I42.2*, Q20.*, Q21.*, Q22.*, Q23.*, Q24.*, Q25.*, E74.*, E75.*, D86.* |

A censoring event was defined as death, end of observation, or an intervention that directly treated the disease and could modify the underlying physiology or impact the ECG signal, such as valve replacement or repair. In other embodiments, heart transplant or LVAD status, for example, may be included as censoring events. A negative TTE report after a positive TTE report also may be used as a censoring event to account for the possibility of such interventions being performed outside of the first entity healthcare system.

For the composite endpoint, an ECG was labeled as positive if any of the seven individual outcomes were positive and as negative if all seven outcomes were negative.

Model Development

A plurality of models, e.g., 8 models, may be developed using different combinations of multiple input sets including structured data (demographics, vitals, labs, structured ECG findings and measurements) and ECG voltage traces.

In one instance, for the ECG trace models, a low-parameter convolutional neural network (CNN) was developed with 18,495 trainable parameters that consisted of six 1D CNN-Batch Normalization-ReLU (CBR) layer blocks followed by a two-layer multilayer perceptron and a final logistic output layer (Table 7). Specifically, Table 7 details a single output low-parameter CNN design for training on 8 non-derived ECG leads. The network contains a total of 18,945 trainable and 384 non-trainable parameters. Both Dropout layers were set at 25% drop rate. CBR is a brief notation for a sequence of 1D CNN, batch normalization, and ReLU layers.

TABLE 7

| Layer | Output Shape | # Parameters |
| --- | --- | --- |
| Input | (5000, 8) | 0 |
| Rescaling | (5000, 8) | 0 |
| CBR-1 | (5000, 16) | 656 + 64 |
| CBR-2 | (5000, 16) | 1,296 + 64 |
| MaxPool1D | (1666, 16) | 0 |
| CBR-3 | (1666, 16) | 1,296 + 64 |
| CBR-4 | (1666, 16) | 1,296 + 64 |
| MaxPool1D | (555, 16) | 0 |
| CBR-5 | (555, 16) | 1,296 + 64 |
| CBR-6 | (555, 16) | 1,296 + 64 |
| MaxPool1D | (185, 16) | 0 |
| CBR-7 | (185, 16) | 1,296 + 64 |
| CBR-8 | (185, 16) | 1,296 + 64 |
| MaxPool1D | (61, 16) | 0 |
| CBR-9 | (61, 16) | 1,296 + 64 |
| CBR-10 | (61, 16) | 1,296 + 64 |
| MaxPool1D | (20, 16) | 0 |

TABLE 7-continued

| Layer | Output Shape | # Parameters |
| --- | --- | --- |
| CBR-11 | (20, 16) | 1,296 + 64 |
| CBR-12 | (20, 16) | 1,296 + 64 |
| MaxPool1D | (6, 16) | 0 |
| Flatten | (96,) | 0 |
| Dense + Dropout | (32,) | 3104 |
| Dense + Dropout | (16,) | 528 |
| Dense | (1,) | 17 |

Figure 25B:
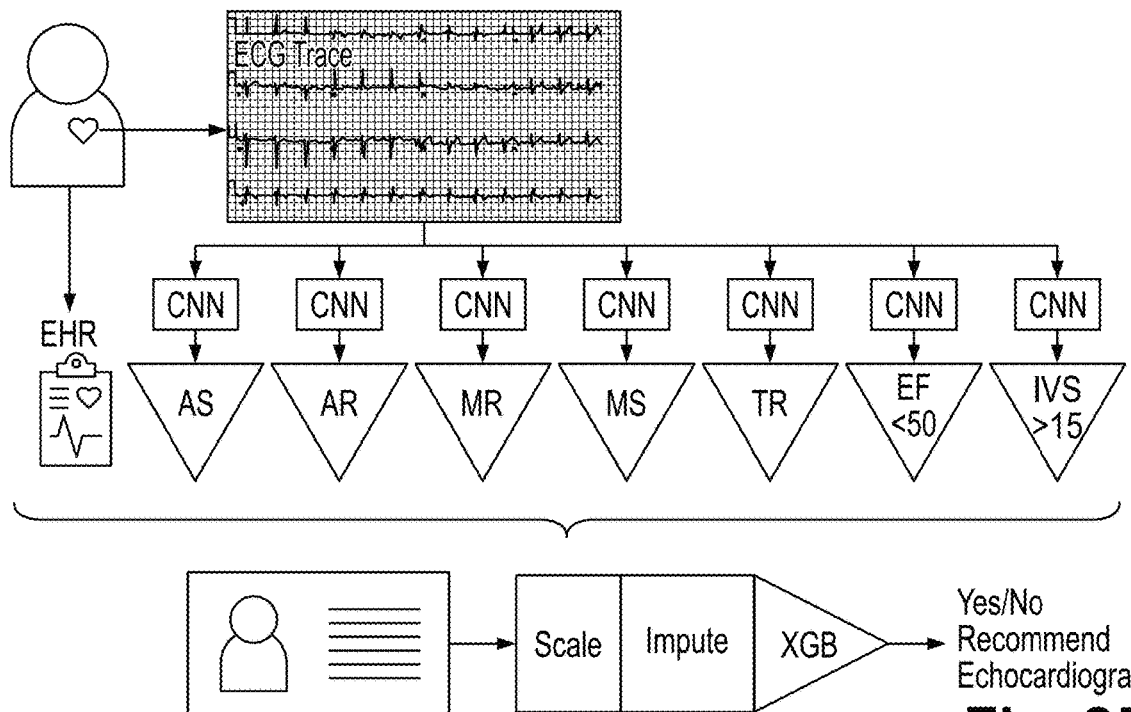
FIG. 25B displays a block diagram for a composite model that shows the classification pipeline for ECG trace and other EHR data.

Each CNN layer consisted of 16 kernels of size 5. The same network configuration was used to train one model per clinical outcome, resulting in 7 independently trained CNN models (FIG. 25B). Specifically, FIG. 25B displays a block diagram for a composite model that shows the classification pipeline for ECG trace and other EHR data. The output of each neural network (the triangles in FIG. 25B) applied to ECG trace data is concatenated to labs, vitals, and demographics to form a feature vector. The vector is the input to a classification pipeline (min-max scaling, mean imputation, and XGBoost classifier), which outputs a recommendation score for the patient.

To form the final composite model and combine ECG trace-based models with structured data, the risk scores resulting from the individual CNNs were concatenated with the structured data. The concatenated feature vector was used to train a classification pipeline consisting of a min-max scaler (min 0, max 1), mean imputation, and a machine learning model or gradient boosting library classifier such as an XGBoost classifier, as shown in FIG. 25B.

Model Evaluation. The models were evaluated using two approaches, 1) a traditional random cross-validation partition, and 2) a retrospective deployment scenario where, using 2010 as the simulated deployment year, past data was used to train and future data was used to test. Area under receiver operating characteristic curve (AUROC), area under the precision-recall curve (AUPRC), and other performance metrics (sensitivity, specificity, positive and negative predictive values) were measured at multiple operating points (Youden, F1, F2, at 90% and 50% sensitivity, at 25% and 33% PPV).

Cross validation. A 5-fold cross-validation was followed by randomly sampling 5 mutually exclusive sets of patients. Each set was expanded to all ECGs from each patient to form the training and test ECG sets. When training the CNN models for each individual endpoint, samples with missing labels were discarded. The model was then applied to all test samples—regardless of missingness of the true label—and marginal performance was evaluated only on samples with complete labels that also satisfied the composite model labeling criteria described above. Performance statistics were reported as the average across the five folds (with a 95% confidence interval) in a random ECG per patient.

Retrospective deployment. In addition to the cross-validation approach, a deployment of the model was also retrospectively simulated using a cutoff of the year 2010, re-labeling all ECGs with information available as of Jan. 1, 2010. This artificially constrained dataset was used to replicate the cross-validation experiments and train a deployment model using data prior to 2010. The deployment model then was applied to the first ECG per patient for all patients seen through Dec. 31, 2010. Performance statistics on all ECGs from patients at risk were measured, and the true outcomes of the at-risk population using all information available as of May 4, 2021, were determined.

Results from Example 1

568,802 TTE reports were identified from 277,358 patients, of which 150,730 were positive for at least one disease outcome label. Disease prevalence ranged from 0.7% for MS to 19.9% for reduced EF (Table 8). Specifically, Table 8 lists TTE label count and relative prevalence for each diagnosis among the 568,802 TTEs.

TABLE 8

|     | Normal-Mild | Moderate-Severe | Prevalence |
|-----|-------------|-----------------|------------|
| AS  | 271,384     | 21,790          | 7.4%       |
| AR  | 278,439     | 13,878          | 4.7%       |
| MR  | 270,266     | 32,002          | 10.6%      |
| MS  | 302,649     | 2,188           | 0.7%       |
| TR  | 258,236     | 36,069          | 12.3%      |

|         | False   | True   |       |
|---------|---------|--------|-------|
| EF <50  | 308,695 | 76,806 | 19.9% |
| IVS >15 | 362,974 | 27,389 | 7.0%  |

2,141,366 ECGs were identified from 461,466 patients who met criteria for a positive or negative individual disease label (AS, AR, MS, MR, TR, EF, or IVS), of which 1,378,832 ECGs from 333,128 patients qualified for the composite label (Table 9). Specifically, Table 9 lists the count of ECGs and total prevalence for each diagnosis among the 2,141,366 ECGs with at least a complete label. Confirmed counts are based on ECGs from patients that also underwent an Echocardiography study that confirmed the diagnosis. Unconfirmed negatives (−) show the count of ECGs from patients that never got an Echocardiography and had no history of the disease using the ICD code filters from Table 6.

TABLE 9

|                       | Negative  | Positive | Prevalence | No label |
|-----------------------|-----------|----------|------------|----------|
| AS                    | 1,608,160 | 65,037   | 3.9%       | 468,169  |
| AR                    | 1,609,710 | 58,209   | 3.5%       | 473,447  |
| MR                    | 1,536,378 | 145,355  | 8.6%       | 459,633  |
| MS                    | 1,691,737 | 9,920    | 0.6%       | 439,709  |
| TR                    | 1,556,020 | 148,916  | 8.7%       | 436,430  |
| EF <50%               | 1,375,507 | 315,874  | 18.7%      | 449,985  |
| IVS >15 mm            | 1,235,255 | 121,583  | 9.0%       | 784,528  |
| Present Composite Model | 805,353 | 573,479  | 41.6%      | 762,534  |

Table 10 displays a breakdown by ECG label of each model feature. Specifically, Table 10 displays average value for each predictor grouped by whether they qualified for the composite labeled ECGs. False refers to ECGs from patients that were not diagnosed with any of the 7 diseases within a year, and True to ECGs from patients that were diagnosed with at least one of the 7 diseases within a year or before the ECG acquisition time.

TABLE 10

|                         | FALSE        | TRUE         |
|-------------------------|--------------|--------------|
| Demographics and Vitals: |              |              |
| Age                     | 55.9 (16.9)  | 71.2 (13.6)  |
| Race                    | 96.9         | 97.5         |
| Sex                     | 44.7         | 58.3         |
| Smoker                  | 58.3         | 62.9         |
| BMI                     | 30.8 (8.4)   | 30.1 (9.1)   |
| BP Diastolic            | 73.8 (11.2)  | 70.2 (12.8)  |
| BP Systolic             | 127.5 (18.6) | 128.1 (21.5) |
| Heart Rate              | 77.1 (14.8)  | 76.1 (16.5)  |
| Height                  | 168.3 (10.5) | 168.9 (11.2) |
| Weight                  | 87.2 (23.7)  | 86.0 (24.5)  |
| Labs:                   |              |              |
| A1C                     | 6.8 (3.9)    | 6.9 (1.6)    |
| BILI                    | 0.5 (0.5)    | 0.6 (0.7)    |
| BUN                     | 16.5 (8.7)   | 25.6 (16.2)  |
| Cholesterol             | 183.6 (46.0) | 158.8 (47.4) |
| CKMB                    | 6.6 (23.5)   | 10.0 (37.2)  |
| Creatinine              | 1.0 (2.0)    | 1.4 (1.3)    |
| CRP                     | 22.7 (51.0)  | 48.3 (70.6)  |
| Ddimer                  | 1.0 (2.0)    | 1.9 (3.1)    |
| Glucose                 | 114.0 (43.3) | 123.1 (52.1) |

TABLE 10-continued

|  | FALSE | TRUE |
|---|---|---|
| HDL | 49.6 (16.1) | 45.6 (15.6) |
| Hemoglobin | 13.7 (21.9) | 13.9 (43.9) |
| LDH | 217.4 (134.6) | 274.2 (290.8) |
| LDL | 103.4 (37.6) | 85.7 (37.1) |
| Lymphocytes | 24.9 (10.5) | 19.9 (10.6) |
| Potassium | 4.2 (0.7) | 4.3 (0.7) |
| PROBNP | 1032.1 (3880.0) | 6868.1 (12317.4) |
| Sodium | 139.3 (3.0) | 138.9 (3.7) |
| TroponinI | 0.8 (12.4) | 1.1 (10.2) |
| TroponinT | 0.1 (0.4) | 0.2 (1.1) |
| Triglyceride | 158.8 (127.7) | 144.9 (108.9) |
| UricAcid | 6.1 (2.1) | 7.1 (2.7) |
| VLDL | 30.4 (15.8) | 28.1 (15.9) |
| eGFR | 58.0 (16.9) | 49.8 (15.2) |
| ECG: | | |
| Avg RR Interval | 831.5 (186.0) | 794.2 (204.6) |
| PR Interval | 158.3 (32.6) | 175.5 (388.3) |
| P Axis | 47.7 (25.5) | 50.3 (36.4) |
| QRS Duration | 90.6 (17.7) | 109.6 (30.8) |
| QT | 392.3 (43.9) | 409.8 (59.5) |
| QTC | 433.5 (34.1) | 463.6 (45.9) |
| R Axis | 28.1 (40.7) | 17.9 (64.3) |
| T Axis | 42.6 (37.4) | 69.8 (69.8) |
| Vent Rate | 76.1 (18.8) | 80.8 (22.6) |
| Acute MI | 0.6 | 2 |
| AFIB | 3.1 | 18.4 |
| Normal | 52.6 | 28.4 |
| AFLUTTER | 0.6 | 2.8 |
| FAS Block | 1.9 | 4.9 |
| First Deg Block | 3.8 | 9.3 |
| Intrav Block | 0.8 | 5.2 |
| In RBBB | 0.1 | 0.9 |
| Ischemia | 5.4 | 18.3 |
| LAD | 5.7 | 14.8 |
| LBBB | 0.8 | 6.1 |
| LOWQRS | 3.5 | 6.2 |
| LVH | 5.7 | 10.6 |
| Non-Spec ST | 8.2 | 13.4 |
| Non-Spec T | 13.5 | 19.9 |
| PVC | 3.5 | 12.8 |
| PAC | 3.3 | 7 |
| Pacemaker | 1.3 | 10 |
| Poor Tracing | 4.1 | 6.5 |
| Prior Infarct | 12.5 | 28.6 |
| Prior MI Ant. | 4.6 | 12.2 |
| Prolonged QT | 3.2 | 8.4 |
| RAD | 1.9 | 3 |
| RBBB | 3.3 | 9.8 |
| Sinus Brady | 15.6 | 10.8 |
| Tachy | 7.9 | 7.9 |
| T Inversion | 2.7 | 7.5 |

At baseline, across 2.14 million ECGs, the median patient age was 64.7, 50.4% were male, and 96.7% were white (Table 11). Specifically, Table 11 lists features extracted at the time of the ECG and their overall average, for continuous values, or prevalence, for binary values. Other ECG features not listed because of their rarity (<1%) were: Complete Block, Other Brady, Early Rep, IN LBBB, Sec Deg Block, SVT, and VTACH. ECG findings showed 43.5% were normal, 8.3% had atrial fibrillation, 1.0% showed acute myocardial infarction, and 7.7% showed left ventricular hypertrophy.

TABLE 11

|  | Mean | Median [IQR] |
|---|---|---|
| Demographics and Vitals: | | |
| Age (years) | 63 | 64.7 [52, 76] |
| Race (% White) | 96.7% | |
| Sex (% Male) | 50.4% | |
| Smoke (% Ever) | 59.1% | |
| BMI (kg/m2) | 30.7 | 29.4 [25, 35] |
| Dias. BP (mmHg) | 72.6 | 72 [64, 80] |
| Sys. BP (mmHg) | 128.8 | 128 [116, 140] |
| Heart Rate (bpm) | 76.9 | 75 [66, 85] |
| Height (cm) | 168.6 | 167.6 [160, 178] |
| Weight (kg) | 87.2 | 84.1 [70, 100] |
| Labs: | | |
| A1C | 6.8 | 6.4 [5.7, 7.5] |
| BILI | 0.6 | 0.5 [0.3, 0.7] |
| BUN | 20.3 | 17 [13, 23] |
| Cholesterol | 171.6 | 167 [139, 199] |
| CKMB | 8.3 | 2.9 [1.8, 4.9] |
| Creatinine | 1.2 | 0.9 [0.8, 1.2] |
| CRP | 36.5 | 9 [2.5, 39.0] |
| D dimer | 1.5 | 0.6 [0.3, 1.5] |
| Glucose | 118.4 | 103 [93, 125] |
| HDL | 47.9 | 45 [37, 56] |
| Hemoglobin | 13.6 | 13.1 [11.6, 14.3] |
| LDH | 258 | 211 [173, 272] |
| LDL | 94.6 | 90 [68, 117] |
| Lymphocytes | 22.4 | 22 [14.8, 29] |
| Potassium | 4.2 | 4.2 [3.9, 4.5] |
| PROBNP | 4351 | 1015 [249, 3553] |
| Sodium | 139.2 | 140 [137, 141] |
| Troponin I | 88.8 | 3 [1.2, 5] |
| Troponin T | 13.5 | 1 [1, 38] |
| Triglyceride | 152.2 | 125 [89, 181] |
| Uric Acid | 6.6 | 6.2 [4.9, 7.9] |
| VLDL | 28.6 | 25 [18, 35] |
| eGFR | 54.5 | 60 [55.2, 60] |
| ECG: | | |
| Avg RR Interval | 813.5 | 806 [678, 938] |
| PR Interval | 164.4 | 160 [142, 180] |
| P Axis | 48.5 | 51 [34, 65] |
| QRS Duration | 97 | 90 [82, 102] |
| QT | 397.9 | 396 [366, 428] |
| QTC | 444.6 | 440 [419, 464] |
| R Axis | 22.9 | 21 [−9, 54] |
| T Axis | 51.6 | 45 [23, 70] |
| Vent Rate | 78.2 | 74 [64, 88] |
| Acute MI | 1.0% | |
| AFIB | 8.3% | |
| Normal | 43.5% | |
| AFLUTTER | 1.3% | |
| FAS Block | 3.2% | |
| First Deg Block | 6.1% | |
| Intrav Block | 2.1% | |
| INRBBB | 3.3% | |
| Ischemia | 9.6% | |
| LAD | 9.1% | |
| LBBB | 2.6% | |
| LOWQRS | 4.7% | |
| LVH | 7.7% | |
| Non-Spec ST | 10.4% | |
| Non-Spec T | 16.0% | |
| PVC | 6.7% | |
| PAC | 5.1% | |
| Pacemaker | 4.2% | |
| Poor Tracing | 5.3% | |
| Prior Infarct | 18.4% | |
| Prior MI Ant. | 7.3% | |

TABLE 11-continued

|  | Mean | Median [IQR] |
|---|---|---|
| Prolonged QT | 5.0% | |
| RAD | 2.2% | |
| RBBB | 6.0% | |
| Sinus Brady | 13.5% | |
| Tachy | 8.4% | |
| T Inversion | 4.5% | |

Composite Model Input Evaluation

Table 12 shows the results of 5-fold cross validation comparing composite model performance as a function of different input features. Specifically, Table 12 provides a performance comparison of cross-validated models with varying input features for the composite endpoint (valve disease, reduced EF, increased IVS). All values are shown in percentage with the 95% CI in between brackets. Each model was tested on a random ECG per patient. The AUROC ranged from 84.7 [95% CI: 84.5, 85.0] for the model built only with structured ECG findings and measurements to 93.2 [93.0, 93.4] for the model with all available inputs (structured ECG findings and measurements, demographics, labs, vitals, and ECG traces). While the model with all available inputs provided the best performance, the remainder of the results focus on models that include only age, sex, and ECG traces since this input set is readily available from the third entity or other ECG systems and best balances portability and performance.

TABLE 12

| Input | ROC-AUC | PRC-AUC | PPV @ 90% Sens. | Spec. @ 90% Sens. |
|---|---|---|---|---|
| A) ECG Findings and Meas | 84.7 [84.5, 85.0] | 67.5 [67.0, 67.9] | 36.1 [35.7, 36.5] | 52.8 [52.0, 53.6] |
| B) Demo., Labs, and Vitals | 87.9 [87.7, 88.1] | 72.9 [72.4, 73.4] | 43.0 [42.8, 43.1] | 64.4 [64.2, 64.6] |
| C) ECG Traces | 91.0 [90.7, 91.4] | 77.6 [76.8, 78.5] | 50.8 [49.8, 51.7] | 74.0 [73.0, 74.9] |
| A + C | 91.3 [91.0, 91.5] | 78.3 [77.5, 79.1] | 51.5 [50.7, 52.3] | 74.7 [74.0, 75.5] |
| Age + Sex + C | 91.4 [91.1, 91.7] | 77.5 [76.6, 78.5] | 52.2 [51.3, 53.0] | 75.5 [74.7, 76.2] |
| A + B | 91.5 [91.4, 91.7] | 79.7 [79.1, 80.2] | 51.6 [51.0, 52.1] | 74.8 [74.3, 75.3] |
| B + C | 93.1 [92.8, 93.3] | 82.7 [82.1, 83.3] | 57.0 [56.1, 58.0] | 79.8 [79.1, 80.5] |
| A + B + C | 93.2 [93.0, 93.4] | 83.0 [82.5, 83.5] | 57.5 [56.3, 58.6] | 80.1 [79.3, 81.0] |

Cross-Validation Performance of Composite Model

The composite model with age, sex, and ECG traces as inputs yielded an AUROC of 91.4 [91.1, 91.7] and a PPV of 52.2% [51.3, 53.0] at 90% sensitivity (Table 3*). Specifically, Table 13 displays ECG traces only model results for cross-validation experiments. Results are shown at a random ECG per patient and averaged across 5 folds. All values are shown in percentage with the 95% CI in between brackets. The any label is positive when any of the other seven is positive, and negative when all the other seven are negative.

TABLE 13

|  | Prevalence | ROC-AUC | PRC-AUC | PPV @ 90% Sens. | Spec. @ 90% Sens. |
|---|---|---|---|---|---|
| AS | 3.7 [3.6, 3.8] | 92.4 [92.0, 92.8] | 35.0 [32.4, 37.8] | 14.7 [13.9, 15.6] | 80.1 [78.8, 81.3] |
| AR | 2.9 [2.8, 2.9] | 87.5 [87.0, 88.0] | 21.1 [19.1, 23.2] | 7.2 [6.9, 7.5] | 65.9 [63.8, 67.9] |
| MR | 6.9 [6.8, 7.0] | 92.2 [91.8, 92.6] | 51.9 [50.0, 53.8] | 24.2 [22.7, 25.6] | 79.0 [77.4, 80.5] |
| MS | 0.4 [0.4, 0.5] | 92.3 [90.5, 93.8] | 7.2 [4.9, 10.5] | 2.1 [1.4, 3.0] | 80.7 [72.5, 86.9] |
| TR | 7.3 [7.2, 7.3] | 92.6 [92.0, 93.1] | 57.2 [55.6, 58.7] | 26.0 [24.3, 27.7] | 79.9 [78.1, 81.6] |
| EF <50% | 13.0 [12.8, 13.1] | 93.0 [92.3, 93.6] | 70.5 [66.1, 74.5] | 41.3 [38.4, 44.2] | 80.9 [78.6, 83.0] |
| IVS >15 mm | 6.2 [6.1, 6.3] | 89.1 [88.9, 89.3] | 36.7 [35.6, 37.8] | 17.1 [16.6, 17.6] | 71.2 [70.4, 72.0] |
| Present Composite Model With Age, Sex, and ECG Traces as inputs | 22.9 [22.8, 23.1] | 91.4 [91.1, 91.7] | 77.5 [76.6, 78.5] | 52.2 [51.3, 53.0] | 75.5 [74.7, 76.2] |

Figure 26:
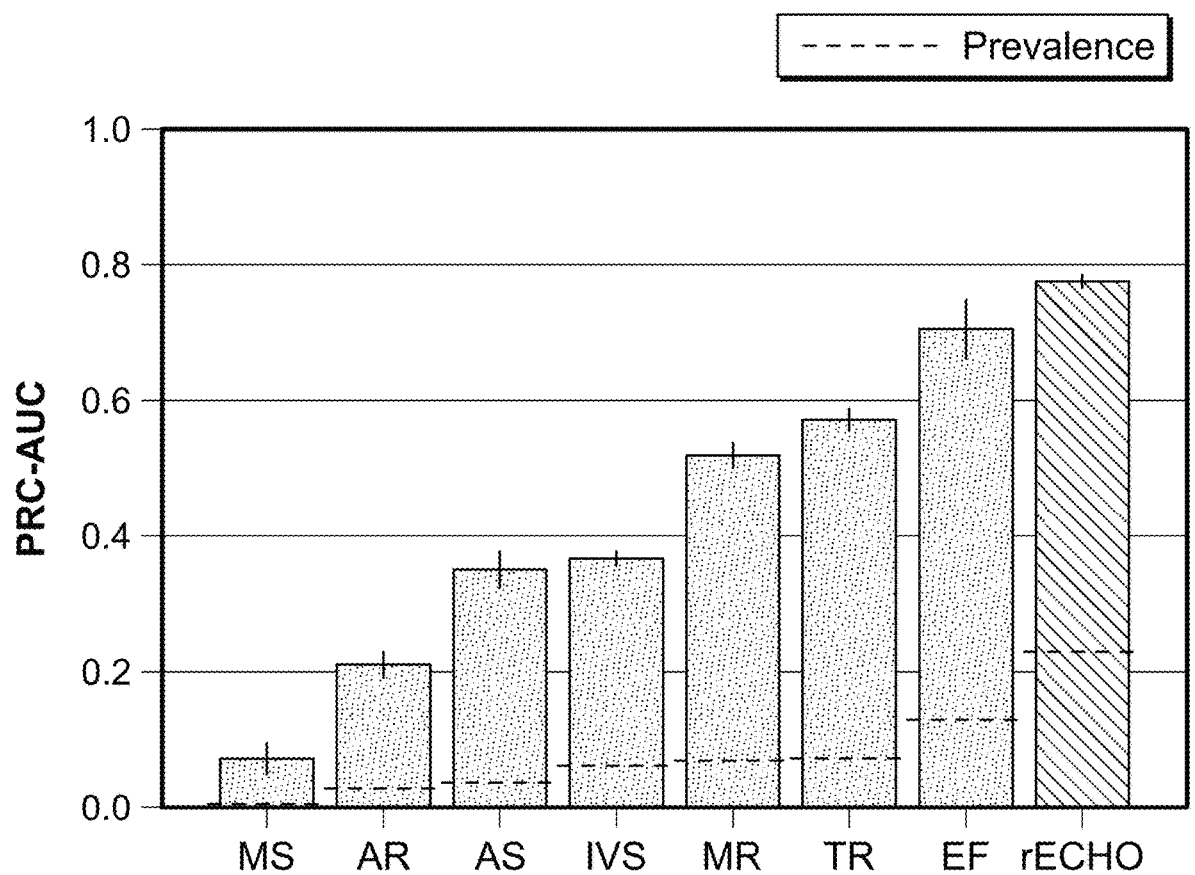
FIG. 26 depicts a comparison of AUPRC of a composite model as compared to a plurality of other individual models.

The composite model yielded a significantly higher PPV than any of the 7 models trained for an individual component endpoint, with the individual model PPVs ranging from 2.1% [1.4, 3.0] for MS to 41.3% [38.4, 44.2] for reduced EF (Table 13). The same trend was found for the AUPRC of the composite model, which was 77.5% [76.6, 78.5], compared to the individual models ranging from 7.2% [4.9, 10.5] for MS to 70.5% [66.1, 74.5] for EF (FIG. 26). Specifically, FIG. 26 displays an area under the Precision-Recall curve for each of the individual diseases and the model of the present disclosure. The dashed line shows the prevalence for each of the labels.

Performance metrics for alternate composite model operating points are presented in Table 14. Specifically, Table 14 lists composite model performance metrics at multiple threshold values.

Figure 27A:
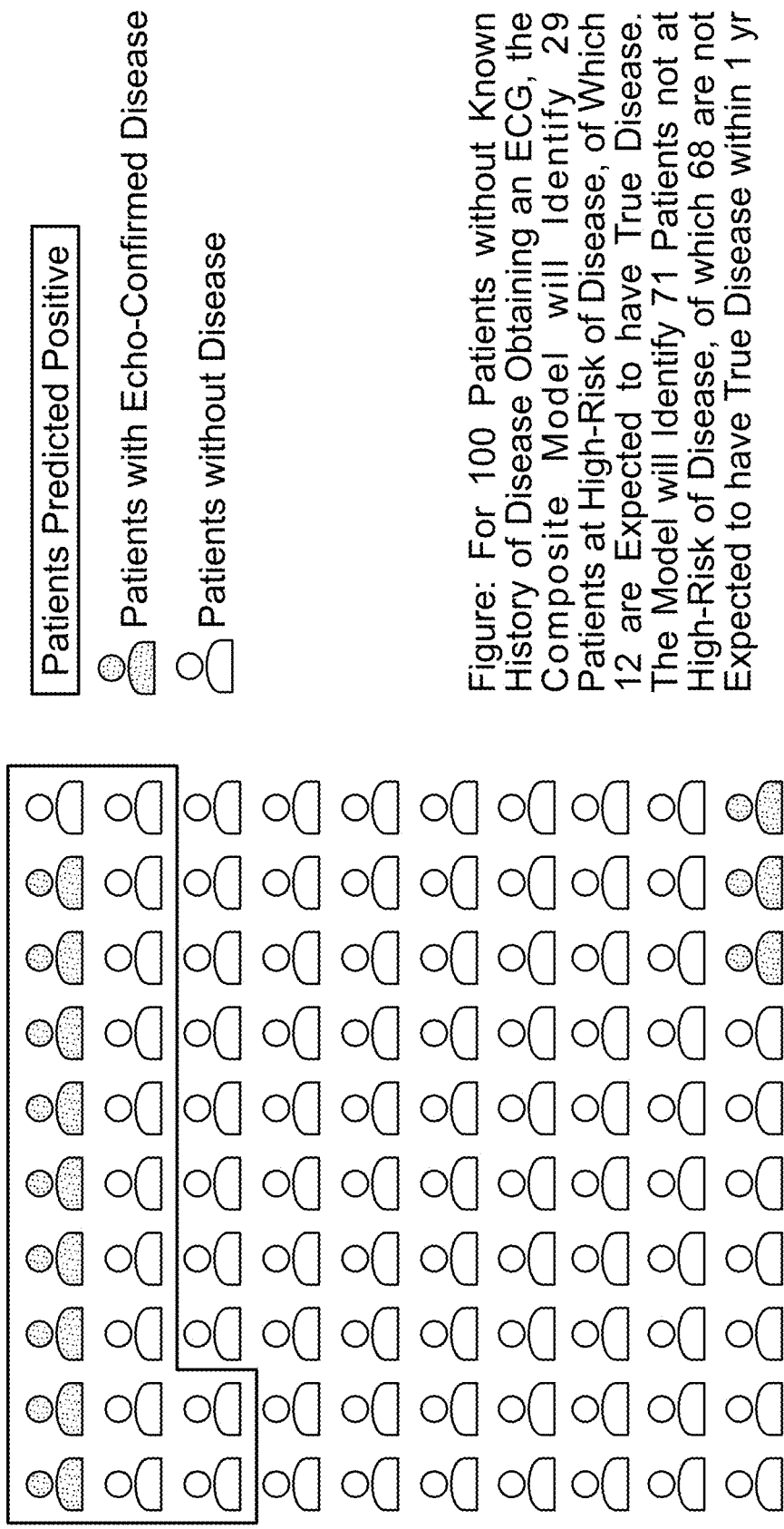
FIG. 27A displays patient-level retrospective deployment results.
Figure 27B:
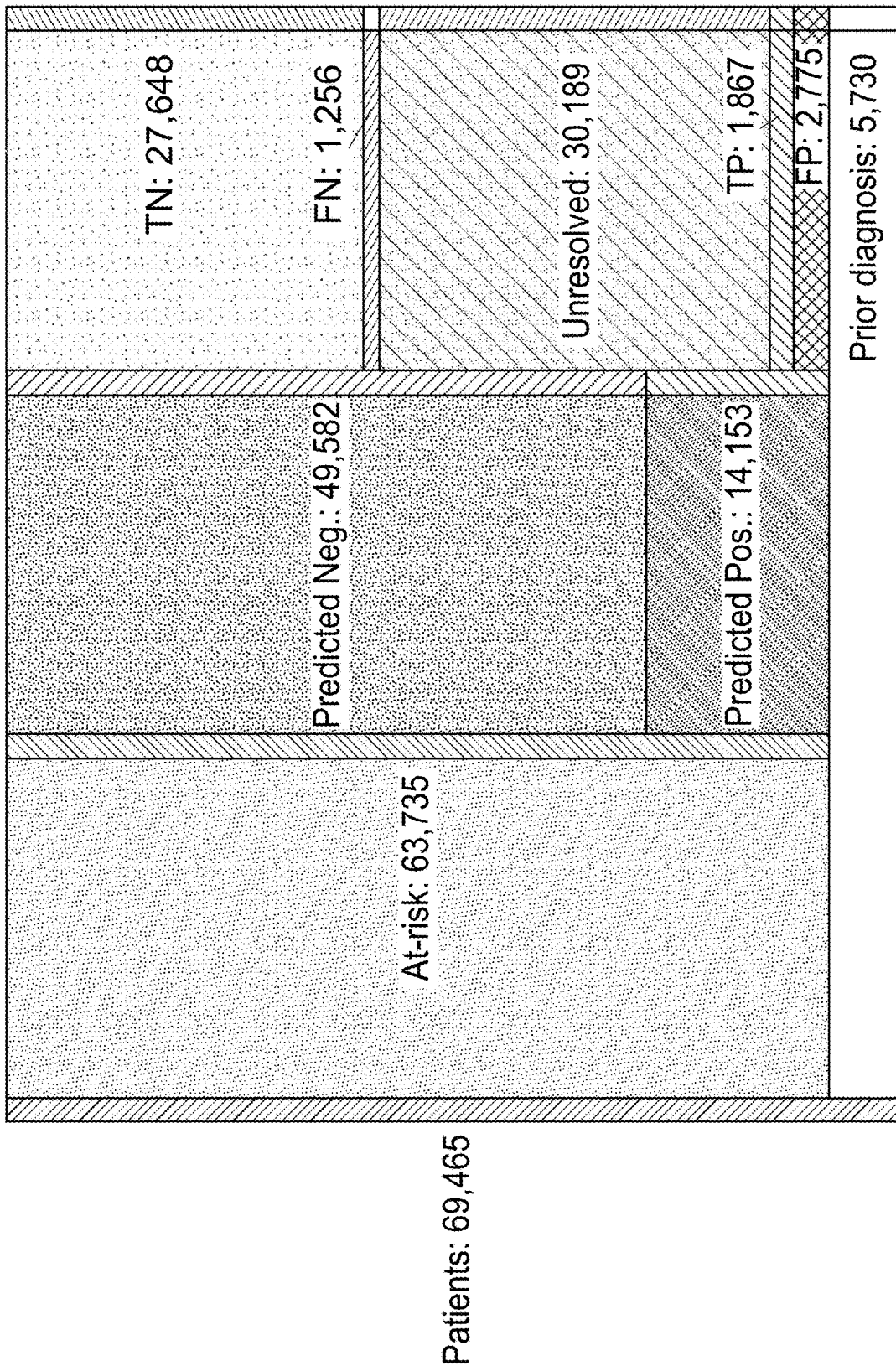
FIG. 27B displays a Sankey plot of retrospective deployment results.

The deployment dataset contained ECGs from 69,465 patients (FIG. 27B). Of these, 5,730 patients were diagnosed with one of the seven clinical outcomes prior to 2010. This resulted in 63,735 at-risk patients identified between January $1^{st}$ and December $31^{st}$ of 2010. Using the previously determined threshold noted above, the deployment model labeled 22.2% of patients as high risk for any of the seven disease outcomes and 77.8% of patients as not high risk. Among the 4,642 predicted high-risk patients with adequate follow-up who met our defined criteria for the composite label, 1,867 patients truly developed one of the outcomes, yielding a PPV of 40.2%. Of these 1,867 patients, 231 (12.4%) developed AS, 147 (7.9%) developed AR, 562 (30.1%) developed MR, 32 (1.7%) developed MS, 505 (27%) developed TR, 1074 (57.5%) developed low EF, and 460 (24.6%) developed IVS thickening—noting that 1083 developed 1 of the

TABLE 14

| Threshold | NPV | PPV | Sensitivity | Specificity | Value |
|---|---|---|---|---|---|
| 0.1 | 95.8 [95.7, 95.9] | 54.4 [53.7, 55.2] | 88.5 [88.1, 88.8] | 78.0 [77.4, 78.5] | 0.1 |
| 0.2 | 92.8 [92.6, 93.0] | 68.1 [67.4, 68.8] | 76.9 [76.1, 77.6] | 89.3 [89.0, 89.6] | 0.2 |
| 0.3 | 90.3 [90.0, 90.5] | 75.9 [75.2, 76.6] | 66.0 [64.9, 67.1] | 93.8 [93.6, 93.9] | 0.3 |
| 0.4 | 87.6 [87.4, 87.8] | 81.4 [80.6, 82.3] | 54.1 [53.3, 54.8] | 96.3 [96.1, 96.5] | 0.4 |
| 0.5 | 84.8 [84.7, 85.0] | 85.9 [84.9, 86.8] | 41.1 [40.6, 41.5] | 98.0 [97.8, 98.1] | 0.5 |
| 0.6 | 82.3 [82.0, 82.5] | 89.3 [88.5, 90.1] | 28.2 [26.6, 29.9] | 99.0 [98.9, 99.1] | 0.6 |
| 0.7 | 79.8 [79.3, 80.3] | 91.6 [91.0, 92.2] | 15.0 [11.6, 19.3] | 99.6 [99.5, 99.7] | 0.7 |
| 0.8 | 77.8 [77.5, 78.0] | 94.2 [92.6, 95.5] | 3.5 [1.6, 7.4] | 99.9 [99.9, 100.0] | 0.8 |
| 0.9 | 77.1 [76.9, 77.2] | 0.0 [0.0, 100.0] | 0.0 [0.0, 0.0] | 100.0 [100.0, 100.0] | 0.9 |
| Youden | 94.4 [94.2, 94.6] | 61.6 [60.2, 63.0] | 83.2 [82.6, 83.9] | 84.6 [83.6, 85.5] | 14.4 [13.5, 15.3] |
| F1 | 92.5 [92.1, 92.9] | 69.4 [67.2, 71.6] | 75.5 [73.8, 77.2] | 90.1 [88.8, 91.2] | 21.4 [19.6, 23.3] |
| F2 | 95.9 [95.7, 96.0] | 54.1 [53.3, 54.9] | 88.7 [88.2, 89.2] | 77.6 [76.7, 78.4] | 9.8 [9.2, 10.4] |
| @ 25% PPV | 99.5 [99.4, 99.6] | 25.0 [25.0, 25.0] | 99.8 [99.7, 99.9] | 10.9 [10.2, 11.5] | 0.7 [0.6, 0.8] |
| @ 33% PPV | 98.8 [98.7, 98.9] | 33.0 [33.0, 33.0] | 98.3 [98.2, 98.5] | 40.6 [40.1, 41.0] | 2.2 [2.1, 2.4] |
| @ 90% Spec. | 92.5 [92.3, 92.8] | 69.2 [68.8, 69.6] | 75.6 [74.5, 76.6] | 90.0 [90.0, 90.0] | 21.2 [20.7, 21.6] |
| @ 50% Sens. | 86.7 [86.6, 86.8] | 83.0 [81.9, 84.1] | 50.0 [50.0, 50.0] | 97.0 [96.7, 97.2] | 43.3 [42.7, 43.8] |
| @ 90% Sens. | 96.2 [96.2, 96.2] | 52.2 [51.3, 53.0] | 90.0 [90.0, 90.0] | 75.5 [74.7, 76.2] | 8.9 [8.6, 9.2] |

Simulated Deployment Performance of Composite Model

As of Jan. 1, 2010, 563,375 ECGs were identified with a qualifying label for any of the seven clinical outcomes prior to 2010, of which 349,675 ECGs qualified for the composite label to train the deployment model. A "qualifying" label was one that met the criteria for the applicable outcome label. A cross-validation experiment within this data subset showed similar, yet slightly reduced performance of the composite model compared with the full dataset (AUROC 88.8 [88.5, 89.1]; PPV=44.0% [42.9, 45.1] at 90% sensitivity; Table 15). Specifically, Table 15 lists cross-validation performance metrics computed with data prior to 2010. The five-fold average threshold that yielded 90% Sensitivity (0.056 from a range of 0 to 1) was taken to produce binary predictions on the deployment model.

7 diseases while 496 developed 2, 225 developed 3, 55 developed 4, 7 developed 5, 1 developed 6 and 0 developed all 7 diseases.

Among those predicted not high risk, 27,648 patients did not develop any of the outcomes within a year, for an NPV of 95.7%. At the patient level, for every 100 at-risk patients who obtained an ECG, the model used with the present system and methods would identify 22 as high-risk, of which 9 would truly have disease, and 78 as not-high risk, of which 75 would truly not have disease within 1 year (FIG. 27A). Specifically, FIG. 27A displays patient-level retrospective deployment results from 2010 according to the present composite model. FIG. 27B displays a Sankey plot of retrospective deployment results.

TABLE 15

| | Prevalence | ROC-AUC | PRC-AUC | PPV @ 90% Sens. | Spec. @ 90% Sens. |
|---|---|---|---|---|---|
| AS | 2.5 [2.3, 2.6] | 90.6 [89.7, 91.4] | 22.8 [19.0, 27.1] | 8.1 [7.4, 8.9] | 74.1 [71.5, 76.5] |
| AR | 2.8 [2.7, 2.9] | 84.5 [83.5, 85.5] | 15.6 [14.2, 17.1] | 6.1 [5.6, 6.6] | 60.1 [55.6, 64.5] |
| MR | 7.0 [6.8, 7.3] | 89.3 [88.2, 90.2] | 40.1 [36.0, 44.2] | 19.6 [17.6, 21.7] | 72.0 [68.6, 75.2] |
| MS | 0.3 [0.2, 0.3] | 88.1 [84.3, 91.1] | 3.8 [1.8, 7.7] | 0.7 [0.4, 1.2] | 65.0 [46.6, 79.7] |
| TR | 5.4 [5.2, 5.6] | 90.6 [89.9, 91.2] | 41.2 [38.3, 44.1] | 16.7 [15.3, 18.1] | 74.3 [71.6, 76.8] |
| EF <50% | 12.3 [12.0, 12.6] | 90.7 [87.7, 93.0] | 57.5 [46.7, 67.7] | 35.6 [30.2, 41.4] | 77.1 [71.0, 82.3] |
| IVS >15 mm | 7.2 [7.1, 7.4] | 85.9 [85.1, 86.7] | 32.4 [31.4, 33.5] | 16.3 [15.1, 17.6] | 64.1 [60.6, 67.5] |
| Composite Model | 21.1 [20.9, 21.3] | 88.8 [88.5, 89.1] | 67.6 [66.3, 68.9] | 44.0 [42.9, 45.1] | 69.4 [68.0, 70.8] |

Outcome labels for 30,335 patients were undefined due to inadequate follow-up or patients not meeting defined criteria for the composite label, as noted above. However, baseline characteristics among these undefined patients and patients with complete outcome labels were similar (Table 16). Specifically, Table 16 displays baseline characteristics of patients with resolved vs unresolved labels in deployment scenarios. The AUROC among resolved labels was 84.4.

TABLE 16

|  | Resolved Mean (SD) | Median | Unresolved Mean (SD) | Median |
| --- | --- | --- | --- | --- |
| Age | 56 (17) | 57 | 63 (17) | 64 |
| BMI | 31 (8) | 29 | 31 (8) | 30 |
| BP Distolic | 73 (11) | 72 | 74 (12) | 73 |
| BP Systolic | 127 (18) | 124 | 130 (9) | 128 |
| Heart Rate | 76 (13) | 74 | 75 (14) | 74 |
| Height | 168 (10) | 168 | 168 (11) | 168 |
| Weight | 87 (23) | 84 | 87 (25) | 84 |
| A1C | 7 (1) | 6 | 7 (1) | 6 |
| BIL1 | 1 (1) | 0 | 1 (1) | 0 |
| BUN | 17 (9) | 15 | 19 (11) | 17 |
| Cholesterol | 182 (43) | 178 | 178 (43) | 173 |
| CKMB | 4 (8) | 3 | 5 (10) | 3 |
| Creatinine | 1 (1) | 1 | 1 (1) | 1 |
| CRP | 17 (40) | 4 | 21 (45) | 5 |
| Ddimer | 1 (3) | 0 | 2 (3) | 1 |
| Glucose | 109 (36) | 99 | 111 (36) | 100 |
| HDL | 51 (16) | 48 | 50 (15) | 48 |
| Hemoglobin | 14 (28) | 14 | 15 (50) | 13 |
| LDH | 217 (106) | 191 | 246 (239) | 197 |
| LDL | 102 (36) | 98 | 98 (35) | 94 |
| Lymphocytes | 25 (10) | 25 | 24 (11) | 23 |
| Potassinm | 4 (0) | 4 | 4 (0) | 4 |
| PROBNP | 2408 (8570) | 418 | 1577 (2868) | 483 |
| Sodiom | 139 (3) | 139 | 139 (3) | 139 |
| Troponin I | 0 (0) | 0 | 0 (1) | 0 |
| Troponin T | 0 (0) | 0 | 0 (0) | 0 |
| Triglyceride | 150 (105) | 126 | 151 (115) | 127 |
| UricAcid | 6 (2) | 6 | 7 (3) | 6 |
| VLDL | 30 (15) | 27 | 24 (11) | 21 |
| eGFR | 58 (8) | 60 | 56 (9) | 60 |

The composite model described in Example 1 with results of 91.4% AUROC, 52.2% PPV and 90% sensitivity on cross-validation is based on age, sex, and ECG traces alone as inputs, which may represent one possible favorable balance between performance and portability. This model uses data readily available from any ECG system, including those systems commonly available to and/or recognized by those of ordinary skill in the art, so that it can easily be deployed across most healthcare systems. Although the model substantially outperformed those using only demographics or structured ECG findings and measurements, it will be appreciated that other demographics/vitals, labs, ECG findings, and/or ECG measurements, including any of the options listed in Table 1 or other relevant options may be used as inputs to train and/or deploy the composite model. While the addition of EHR data did slightly improve performance, the inclusion of EHR data in some instances may result in decreased portability with the need for EHR or clinical data warehouse integration. Thus, implementation of the present composite model may represent a balance between marginal improvements in performance due to the inclusion of different or additional inputs versus the time or processing costs associated with the integration, normalization, structuring, and/or other processing of additional or alternative inputs.

In a simulated retrospective deployment on ECGs from 2010, approximately 22% of at-risk patients without history of disease were predicted to be high-risk for diagnosis of one of the seven cardiovascular disease outcomes within the following year. Of the patients who were predicted high risk and had adequate follow-up, over 40% were truly diagnosed with disease in the following year after index ECG, through only standard clinical care at the time and without any potential clinician behavior change or active intervention that true deployment of such a prediction model or decision support tool may elicit. This suggests that this 40% PPV is most likely a lower bound for the expected real-world performance of the composite model described in Example 1. Meanwhile the 95.7% NPV suggests that little disease will be missed but even in this case, the model would not change what would otherwise be the clinical course for these patients. Clinician behavior may change with a negative prediction if they are falsely reassured that the patient does not have disease or changes their pretest probability and clinical reasoning. Thus, implementation can be designed so that clinicians are only alerted when a patient is predicted to be high risk, and for those patients, the real-world data discussed herein indicates that more than 4 out of every 10 patients will have true disease. Cross-validation performance metrics that depend on prevalence (PPV, NPV, and AUPRC) may overestimate real-world performance given the lower incidence or prevalence across the generally smaller time window of deployment as opposed to the typically extensive period used in cross-validation. For example, PPV in cross-validation of the model disclosed herein was 52% but dropped to 40% in simulated deployment. However, even a 40% increase in the identification and potential for treatment of patients that ultimately experience one or more of the modeled disease states still represents a marked-improvement over situations in which the disease states are not identified until later on, e.g., once the patient has begun experiencing symptoms.

The exemplary composite model described in Example 1 has some characteristics that need not be present in other embodiments. For example, the training and evaluation related to that composite model were limited to a single regional health system where most patients are white, so similar models designed and implemented according to the present disclosure may consider a diversity of the relevant patient population and may factor that diversity into the relevant composite model or may adjust the present composite model to account for that diversity. Other models may consider and account for other differences in patient populations, such as physiologic differences across race and/or ethnicity to determine whether these ECG-based models perform differently across groups. In addition, echocardiography-confirmed diagnoses were used to generate the positive labels discussed herein, which were confirmed on chart review to have a high PPV. There may be additional patients with disease—false negatives—who were not captured using this method, although the retrospective deployment discussed herein suggests that the negatives may be overwhelmingly true negatives as compared to false negatives, given the low prevalence of disease. Certain machine-learning approaches may have limited interpretability in identifying feature importance. For example, IVS thickness may represent infiltrative diseases or may represent very poorly controlled hypertension. However, these diseases are important to recognize. Thus, model selection may take interpretability into consideration when identification is desired.

Composite Model Categorization and Implementation

Embodiments disclosed herein may also be presented as a backend requiring minimal or no interaction from users of the system and may be entirely contained or compatible within an external electronic health record system or electronic medical system. A third party system housing the medical records of a hospital, physician office, institution, clinical trial, or other entity that manages patient data may incorporate the embodiments as disclosed herein. The backend may be selected by administrators of the EMR/EHR and the underlying algorithms automatically applied on the integrated patient data.

A form may be provided within the EMR/EHR listing all available composite models, such as algorithms predicting the risk of cardiac events for a patient. The form may be presented as a website or as a dynamically updated interface within the EMR/EHR. The form may include one or more algorithm titles, an indication of a creating entity, a description of the algorithm's functionality, optional indexable and/or filterable tags, a description of the inputs to the algorithm, and a description of the output the algorithm will provide. In some embodiments, the output may include a notification and/or the automatic inclusion of the output data into each respective patient's dataset. Each algorithm may be associated with a subscription fee set by the creating entity. Exemplary composite models for generating one or more form algorithms for listing are described herein.

A health care provider may enroll one or more databases of patients into the system. Enrollment may include a backend, frontend, or other EMR integration. The databases may exist within the confinement of the EMR system or may be uploaded to the cloud as part of an information management system. A secure data exchange system may interface and/or liaison information between the databases of patient information and one or more databases of the system provider. Some healthcare providers may desire to keep their databases separate from the system for patient privacy and to protect their proprietary collections of data. Data may be ingested in an unstructured manner for abstraction and curation, in a structured manner, and/or may be normalized between one or more data or structure types. Data may also be securely exchanged between the structured and/or normalized data and one or more of the databases of patient information and one or more databases of the system provider.

Example 2

In another embodiment, a stand-alone model or a composite model may predict active aortic stenosis (AS) and/or AS within a time period such as one year with accuracy using only ECG traces and patient features which may be extracted from the patient's electronic health records. Other time periods between a few minutes, days, weeks, months, or years may be implemented using the same modeling architectures and training methods disclosed herein. Patient features may include age, gender, weight, height, blood pressure, diagnostic laboratory results, and other features. Composite Model training data generation may be modulated between differing normalizing schemes for improved accuracy. For example, lead sample sizes or rates may be lengthened or shortened, patient features may be relabeled from their original states to one or more of categorical states such as, in the case of age, 1-10, 11-20, 21-30, and so forth. Other features may be categorized as well.

The composite model may be any machine learning algorithm which analyzes an ECG waveform and basic demographic data (age/sex) readily available in a digital ECG file and consist of a deep neural network (DNN) or convolutional NN (CNN) trained on data from hundreds of thousands of patients and echocardiograms, and more than a million ECGs. The composite model may effectively analyze the time-voltage signals from a digital 12-lead ECG, with the addition of age and sex as input features into the network, to yield a predicted high-risk score (probability estimate) for moderate or severe TTE-confirmable AS within 1 year of the ECG.

Training a CNN to predict patients of high risk for AS within one year of an ECG is more challenging than training a CNN to recognize active AS. For example, the presentation of active AS, such as a patient who will be diagnosed with AS should a physician review their ECG or echocardiography presents with significantly distinguishable ECG patterns. However, recognizing patients with an ECG up to one year out involves identifying a characteristic from the ECG may be difficult to distinguish from the overbearing signals of active AS for an artificial intelligence engine such as a CNN. Compensating for the disparity between characteristics indicative of active AS and future AS may be implemented during the training of the CNN. In one example, identifying patients having active AS from the training dataset and patients having future AS from the dataset and assigning a label which is not supplied as a training input may be implemented. Active AS may be expanded from within a few days or weeks of an echocardiogram-based diagnosis while future, or incidence, AS may include ECGs outside of those with active AS and up to a year before diagnosis with a similar period expansion of a few days or weeks. Training the CNN may include providing all patients together, without a distinguishing identifier between those having active AS and those with incidence or future AS. The internal validation set, hold out set, and/or test set are filtered to include only those patients which have the incidence or future AS label. By training the model to recognize both active and future AS while refining the model to recognize future and incidence AS, the model may compensate for the disparity between the strength of the signals which identify active AS and future AS and improve performance.

To account for the potential of AS to develop over time, labeling may also include identification of patients who have never had an occurrence of AS in their EMR, such as those indicated by ICD codes related to AS, and may be extended to patients having ECGs but no echocardiography with a diagnosis of AS during the identification of patients having a negative label to be used in training the CNN.

In one example, ECG data may be segmented into multiple portions. A model may be trained using all portions of the segmented ECG or with a varying number of portions. For example, the first or last portion of the ECG may be removed to avoid artifacts that may be present.

In another example, features supplied to a model may be ranked, such as by degree of variance within the dataset or degree of importance as determined after training. Model training may then be performed only on the top 10, 20, 50, 200, or more features as determined by the ranking method applied.

Avoiding bias within the dataset may be implemented by training without confounding features when validation shows that a bias exists. In one such example, a dataset may become biased on the type of machine performing the ECG, individual hospitals, financial access to healthcare systems, race, or other biases. Internal validations may show that no such bias exists, and the training may include all features within the dataset.

The ECG inputs may be arranged within a matrix of data points having a number of samples of each lead stored in rows or columns. The additional patient features may be input into the model downstream of the input layers of the NN at, for example, an XGBoost model component and/or concatenation layer before generating a result at an endpoint, for example, a series of fully connected layers.

While the training methods, bias avoidance methods, and other model improvements are described with respect to the prediction of patients having AS within one year, these methods may be implemented for other high risk of present or future cardiac events, including each of the composite models described herein.

A patient identified as high-risk may prompt a notification, either at the time of diagnostic testing using the ECG or during a patient evaluation period where the patient's records are scanned for high-risk events. Upon notification, a physician may consider increased, more aggressive monitoring for their patient or request the patient receive more diagnostic testing, such as imaging of their heart via an ultrasound/echocardiography.

Example 3

Cardiac amyloidosis (CA) is a rare and potentially fatal disease where diagnosis is often delayed or mishandled due to fragmented guidelines and a poor understanding of the disease etiology. If detected and treated appropriately, prognosis can be improved considerably.

Initial modeling efforts may be stifled due to the lack of data sources for patients having each of ECG history and records, patient features, and an identified presence or absence of CA. Efforts to generate a reliable composite model may include applying machine learning algorithms.

Preparing patients for model training may include generating binary labels were to indicate whether a patient has CA based upon clinician expertise, confounding disease etiologies and data limitations. Cases which may indicate patients with CA which includes light-chain (AL), wild-type transthyretin (wtATTR), hereditary transthyretin amyloidosis (hATTR), and other CA-related features. In another example, patient labels may be based on one or more time periods and/or utilize the patient's entire health record. One time period may include patient health record features which are present within five years of a diagnosis of CA whether before or after. Control patients, or those with a negative label, may be patients who have not had a CA diagnosis in a five year period. Labeling may include a temporal sensing element up to the date of diagnosis, such as having an upper and/or lower bound for time periods which are anchored from the point of diagnosis of a patient. The time periods may be days, weeks, months, years, and in some cases may be extended to the entirety of the patient's data, such as all data, within any time period, after or before the diagnosis. Additional comorbidities which may improve model performance through exclusion from the training dataset include screening patients having cerebral angiopathy diagnosis, AL (continuum of blood cancer), end-stage renal disease (can cause an amyloid looking heart), cerebral amyloid angiopathy, or advanced hypertension. These comorbidities (or distinct diagnosis) may present too similarly to CA and reduce model performance if included. In other models, training may be refined through the use of attention-based models or other approaches to emphasize the distinction between competing diagnoses.

In one example, a composite model may include an ensemble of machine learning and/or deep learning models trained from heterogeneous data including but not limited to ECG, demographics, labs and vitals. Due to the low number of CA patients, this ensemble may utilize deep-learning based ECG feature extractor(s), trained on a clinically informed outcome(s) of interest. As an example, large interventricular septal thickness (IVSD) is a hallmark of CA and is routinely examined in disease diagnosis. IVSD is distilled from echocardiogram making it a highly constrictive screening tool requirement. Thereby the composite model circumvents this requirement by predicting IVSD from ECG, maintaining a larger pool of prospective patients. The proposed feature extractor is not exclusive to IVSD but applicable to any outcome(s) of interest predictable from ECG. These predictions can be used as standalone CA risk scores or nested with other patient features to yield a CA specific model (FIG. 28A-28B).

Figure 28A:
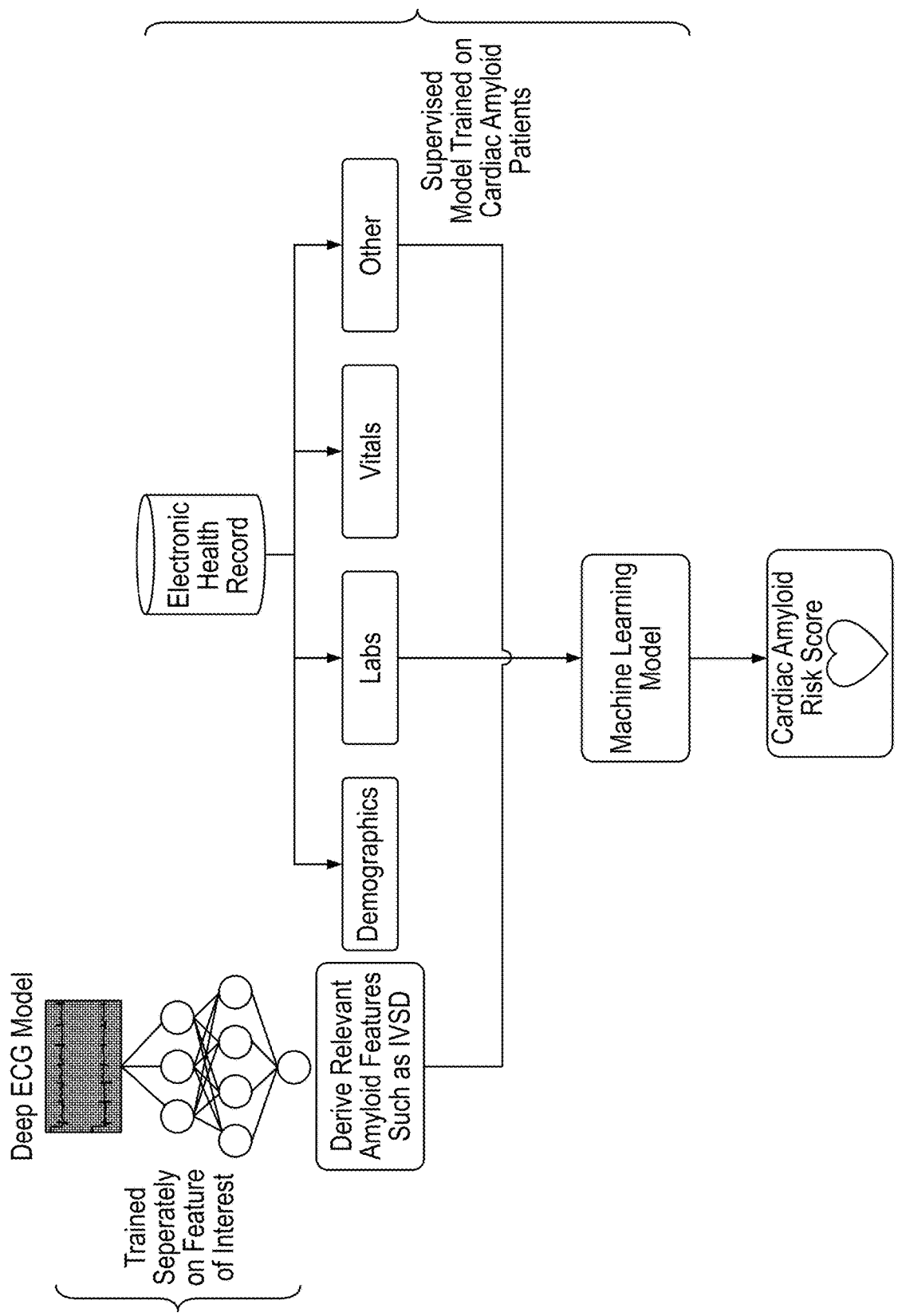
FIG. 28A illustrates a potential configuration of an architecture supporting a composite model for predicting high-risk patients for cardiac amyloidosis.
Figure 28B:
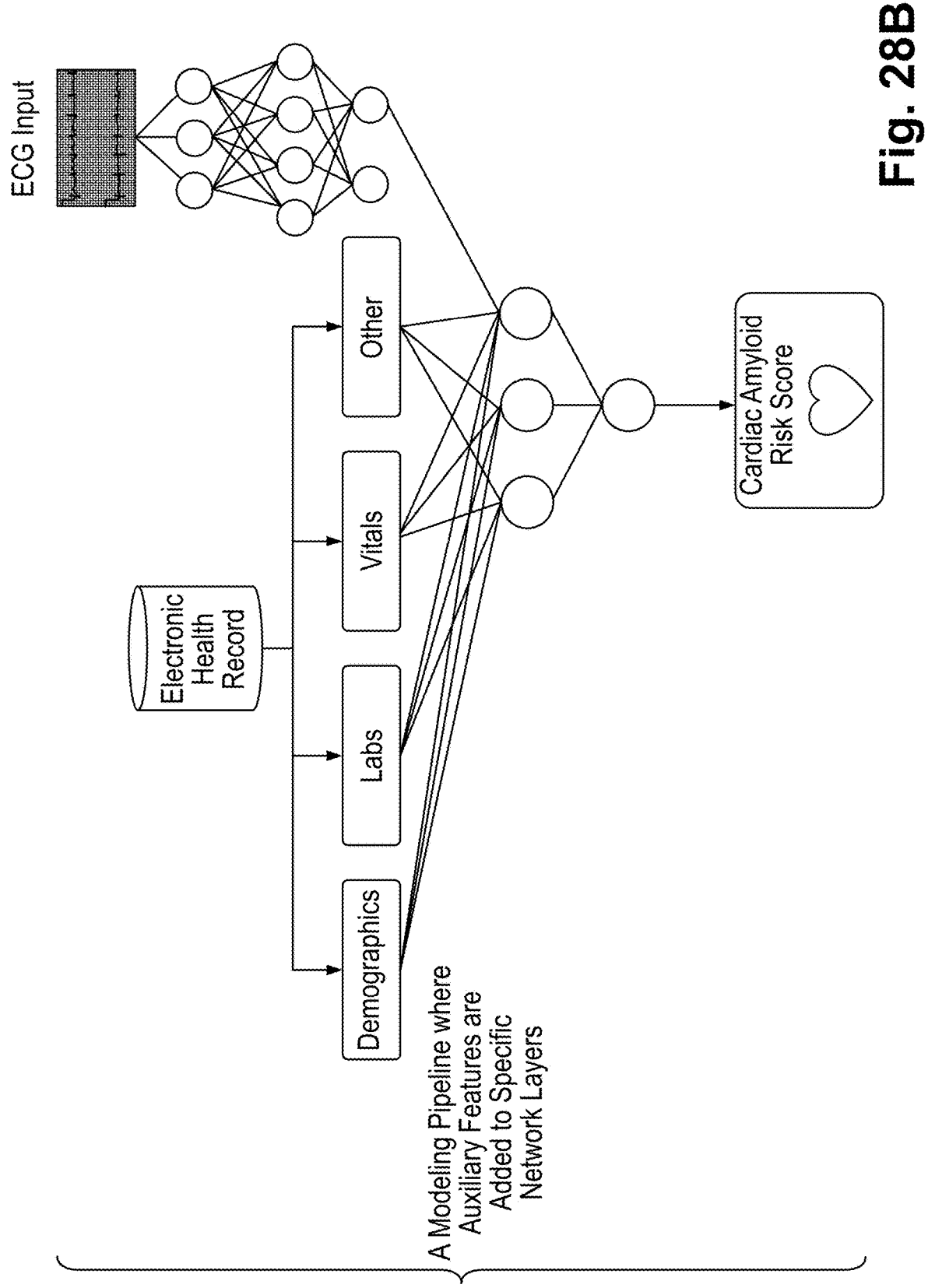
FIG. 28B illustrates a second potential configuration of an architecture supporting a composite model for predicting high-risk patients for cardiac amyloidosis.

FIGS. 28A-28B illustrate two potential configurations of an architecture supporting a composite model for predicting high-risk patients for CA. Other configurations include 2D convolution layers, multiple deep models as feature extractors and one-shot learning approaches.

Example 3 Results

On a holdout set of amyloid patients, the following results were observed using an ECG classifier built to predict interventricular septal thickness (IVSD)> or <=15 mm. All reported metrics are averaged over 5 folds with a 20× bootstrap for patient level metrics.
Results:
ROC AUC: 0.92+/−0.03
Sensitivity: 0.94+/−0.05
Specificity: 0.73+/−0.06
PPV: 0.73+/−0.05

A physician, upon receiving a notification a patient is labeled as high-risk CA, may pursue more aggressive monitoring, increased diagnostics testing, or consider the patient for treatment.

In one embodiment, an entity such as a pharmaceutical company may apply the composite model within the clinic to identify patients at a high likelihood of having CA for the purposes of filling out clinical trials or drug trials. This benefits the patients by decreasing the time to diagnosis and is of low cost to physicians (echo and PYP scans should be covered by insurance).

Example 4

Stroke is relatively common for cardiac events at approximately 800,000 incident strokes in the US annually and presents with a high morbidity and mortality. Upon occurrence, there are major implications for functional status and disability which lead to annual cost of ~$50 Billion (US). Lifetime risk across patients may be as high as 1 in every 4.

Developing a model may include referencing ECG data, EMR data, and providing them to a composite model as described herein. EMR data may include, above and beyond features such as age and gender, identification of symptoms including: unilateral weakness or sensory deficit, facial droop, visual field defect, difficulty speaking/understanding, diplopia, dysarthria, dysphagia, vertigo, incoordination. EMR data may also include diagnosis or comorbidities such as hemorrhage/hematoma, complex migraine, seizure, brain infection/abscess, tumor, hypoglycemia; or even diagnosis and billing codes within the EMR. In a composite model similar to those described above, three inputs may be provided to the model such as ECG leads, age, and gender. In another embodiment, a plurality of features may be selected, such as age, stroke phenotyping, atrial fibrillation (AF), HTN, HLD, DM, smoking, structural heart disease, endocarditis, TIA, PAD, and/or physical inactivity. Stroke phenotyping may include three (qualitatively different) categories: Acute in-system visit (e.g. as referenced in a clinical text/notes showing patient is in ER for treatment of a stroke that just happened), Acute out-of-system visit (e.g. patient has follow-up to recent stroke, <30 days ago), and Historical stroke (e.g. patient mentions a stroke they had years ago).

A composite model for stroke high-risk prediction may include providing:

Inputs:

Clinical notes text: Aggregated to the episode level, and "vectorized" into a bag-of-words representation EHR fields: Length of text and number of notes in the episode, admission types (e.g. ER or Urgent Care), basic "grayzone" queries (e.g. thrombectomy performed, tpa administered, etc.), and/or diagnostic lab values Full input is a concatenation of the above fields Model:

XGBoost Model

Output:

Each episode across the entire EHR is labeled "high-risk of stroke" or "Not high-risk of stroke." Patients may be further aggregated as a list of patient events with corresponding event dates from which notifications of high-risk status or indexing for clinical trials or drug trials may be cultivated.

When ECG traces are selected from 9, 18, or 20 dB and EHR features are selected from age, gender, BMI, blood pressure, smoking status, LDL lab results, diagnosis of CHF, diagnosis of HTN, and diagnosis of diabetes, an exemplary composite model may perform at 70% or greater accuracy.

Inputs may be provided as raw values or categorical values. For a categorical model, the EHR Features may be split into Numeric Features (Age, BMI, BPs, LDL) which are merged with ECG predictions and the feature value with measurement date closest to ECG test date may be selected as the input. For example, if the ECG date is July 15, and there are dates of features captured on July 7th, July 16th, and July 28th, then the selected date from which the input value is derived would be July 16th because it is the closest measurement in time to the ECG. Features may be split off into Categorical Features (CHF, HTN, Diabetes, Smoker) based on whether each respective patient has the disease or not. Combined numerical and categorical patient feature models (with ECG data) may perform at 83% or greater accuracy (Table 17).

Example 4 Results

TABLE 17

| Model | ROC AUC | Sensitivity | Specificity | PPV | NPV |
|---|---|---|---|---|---|
| ECG Only | 0.731 | 0.725 | 0.620 | 0.073 | 0.983 |
| EHR Only | 0.829 | 0.818 | 0.691 | 0.094 | 0.990 |
| ECG + EHR | 0.836 | 0.813 | 0.702 | 0.096 | 0.990 |
| ECG + EHR + AF | 0.843 | 0.802 | 0.726 | 0.102 | 0.989 |

In one example, model inputs may include one or more patient features selected for their importance to the output high-risk label/prediction, including but not limited to demographic features such as age, sex, or other EHR-derived features, in addition to ECG-derived values. For example, LDL diagnostic testing values may account for the highest percentage of the risk assessment and be a required input. In another example, LDL values, ECGs, and age may collectively account for the highest percentage of the risk assessment and be required inputs. In yet another model, inputs may include LDL values, ECGs, age, blood pressure, HTN, AF status, BMI, diabetes, smoking, gender, and/or CHF. In an even more exhaustive implementation, a stroke prediction may include the top X features, where X is an integer. In one example, the integer, X, may be 20 features. Consistent with a 20 feature embodiment, a top 20 features may include: patient age, INDEX_CCI, STROKE_YN, AF_Target, Labs_A1C, Vitals_Weight, Vitals_Height, Demographics_SMOKER_FLG1, Anti_coag, Vitals_BMI, Labs_GLUCOSE, Labs_SODIUM, Vitals_BP_Systolic, Labs_LDL, Medications_ANTICOAGULANTS, Labs_HDL, Labs_HEMOGLOBIN, ECG_R_AXIS, and Echo_measurements_LAV_MOD_sp2.

In some embodiments, all features having a contribution to the high-risk determination with greater than a weight of 1% may be included in the inputs to a composite model. Consistent with a weight inclusion model, features may be selected to include: Vitals_BMI, Vitals_BP_Diastolic, Vitals_BP_Systolic, Vitals_Heart_Rate, Vitals_Height, Vitals_Weight, Demographics_FRS, Demographics_PCE, INDEX_CCI, CHADSVASC_SCORE, CHADS_SCORE, Demographics_PT_AGE, Demographics_PT_RACE, Demographics_PT_SEX, Demographics_SMOKER_FLG, ICD_Phenotypes_AOR, ICD_Phenotypes_AOS, ICD_Phenotypes_IVS, ICD_Phenotypes_LEF, ICD_Phenotypes_MIR, ICD_Phenotypes_MIS, ICD_Phenotypes_PUR, ICD_Phenotypes_PUS, ICD_Phenotypes_TRR, ICD_Phenotypes_TRS, Labs_A1C, Labs_BILI, Labs_BNP, Labs_BUN, Labs_CHOLESTEROL Labs_CKMB, Labs_CREATININE, Labs_CRP, Labs_D_dimer, Labs_eGFR, Labs_GLUCOSE, Labs_HDL, Labs_HEMOGLOBIN, Labs_LDH, Labs_LDL, Labs_LYMPHOCYTES Labs_POTASSIUM Labs_PRO_BNP, Labs_SODIUM, Labs_Triglyceride, Labs_TROPONIN_I, Labs_TROPONIN_T, Labs_URIC_ACID, Labs_VLDL, Medications_ACE_INHIBITORS, Medications_ANGIOTENSIN_II_RECEPTOR_ANTAGONISTS, Medications_ANTICOAGULANTS, Medications_ANTIDIABETIC_MEDICATION, Medications_ANTIHYPERTENSIVE, Medications_DIGOXIN, Medications_ERX_EBBB_HEART_FAILUREMedications_ERX_SPIRONOLACTONE_EPLE R, ONE_HEART_FAILURE, Medications_LOOP_DIURETICS, ECG_Measurements, Echo_Measurements, ECG_Findings, HF_YN, HTN_YN, AGE_GTE_75_YN, DM_YN, STROKE_YN, VASC_DISC_YN, AGE_65_74_YN, and FEMALE_YN.

Models based on the model inputs above may perform at 90% or greater accuracy.

Example 5

In one embodiment, systems and methods described herein for prediction of atrial fibrillation from an ECG may further be adapted to predict other cardiac events from received ECG data. For example, of the received ECG data, measurements may record abnormal variations which are meaningful in additional cardiac event analytics. The QT interval is one such measurement made on an ECG used to assess some of the electrical properties of the heart. It is calculated as the time from the start of the Q wave to the end of the T wave, and approximates to the time taken from when the cardiac ventricles start to contract to when they finish relaxing. An abnormally long or abnormally short QT interval is associated with an increased risk of developing abnormal heart rhythms and sudden cardiac death. Abnormalities in the QT interval can be caused by genetic conditions such as long QT syndrome, by certain medications such as sotalol or pitolisant, by disturbances in the concentrations of certain salts within the blood such as hypokalaemia, by hormonal imbalances such as hypothyroidism, or they may be induced by certain medications. QT prolongation is a measure of delayed ventricular repolarization. Excessive QT prolongation can predispose the myocardium to the development of early after-depolarisations, which in turn can trigger re-entrant tachycardias such as torsades de pointes (TdP). Although the relationship between QT interval duration and the risk of TdP is not fully understood, a corrected QT interval (QTc) of >500 ms or an increase in the QTc of >60 ms may be considered to confer a high risk of TdP in an individual patient. Prolongation of the corrected QT (QTc) interval becomes an even further concern, for example, with patients who receive psychotropic medications. Such patients may have baseline clinical risk factors for QTc prolongation, and many psychotropic medications may further prolong this interval. Analytics may identify over 200 medications having known or suspected association with QTc prolongation (LQT), which can lead to the rare but potentially catastrophic event, TdP.

Models herein generate predictions based upon the combination of ECG data, patient age, and patient sex, although it will be appreciated that other demographic features other than or in addition to one or both of age or sex, and/or other EHR-derived features, may be used as model inputs. Prediction of drug-induced LQT using an ECG-based machine learning model is feasible and may outperform a model trained on baseline QTc, age, and sex alone. In one example, ECG inputs having a baseline 12-lead ECGs with QTc values <500 ms for patients who had not received any known, conditional, or possible QTc prolonging medication at the time of ECG or within the past 90 days may be matched with ECGs from the same patients while they were taking at least one drug ("on-drug" ECGs), such as one of the over 200 medications having known or suspected associations with LQT. Features from the ECG as a whole may be considered in addition to the presence of abnormal QTc features for each respective patient.

Training may include using 5-fold cross-validation on a plurality of models such as two machine learning models using the baseline ECGs of approximately 92,848 resulting pairs to predict drug-induced LQT (≥500 ms) in the on-drug ECGs. Artificial intelligence engines may be implemented, including, by example, a deep neural network using ECG voltage data and a gradient-boosted tree using the baseline QTc with age and sex as additional inputs to both models. Other models may include one or more inputs as described herein. Other combinations of folds, hold-out patients, validations, and number of models for comparison may be considered without departing from the methodology as described herein.

In one such training on an available patient dataset having paired ECG data for patients with both an off-drug ECG and an on-drug ECG, on-drug LQT prevalence was 16%. The ECG model demonstrated superior performance in predicting on-drug LQT (area under the receiver operating characteristic curve (AUC)=0.756) compared to the QTc model (0.710). At a potential operating point such as depicted in FIG. 23, the ECG model had 89% sensitivity and 95% negative predictive value. Even in the subset of patients with baseline QTc <470/480 ms (male/female; post-drug LQT prevalence=14%), the ECG model demonstrated good performance (AUC=0.736). An ECG-based machine learning model can stratify patients by risk of developing drug induced LQT better than a model using baseline QTc alone. This model may have clinical value to identify high-risk drug starts that would benefit from closer monitoring and others who are at low risk of drug induced LQT.

Patients having been identified as high risk for drug-induced LQT may then be reported to their respective physicians for additional monitoring, potential therapy and treatment modifications, or other risk-reduction steps as determined by the physician. In one example, the reporting may include additional risk-reduction steps based upon one or more personal characteristics of the patient, the patient's medical history, the patient's ECG, or publications identified as being pertinent to the patient based upon available data. In another embodiment, the high-risk identification may be generated real-time from the ECG equipment itself based upon the ongoing ECG and the patient characteristics uploaded to the equipment either manually by diagnostic personnel or retrieved from the patient's EMR linked to the ECG equipment.

Extension of Composite Model Implementations to Wearable Devices

Wearable devices, such as those having monitoring technology embedded in the clothing or accessories of a subject, may include one or more monitoring devices that capture instantaneous readings and/or readings over time of heart rates, blood pressure, single or multiple probe ECG, temperature, presence and/or rate of perspiration, and other diagnostic measurements.

While one or more wearable devices are in use, a subject may be monitored closely for incidences of active cardiac conditions/events or high risk of future cardiac conditions/events. For example, one or more leads may be embedded in clothing of the subject which measure waveforms such as those of corresponding ECG traces. In another example, a wearable watch may include an ECG trace which measures the subject's rate and rhythm of heartbeats.

Each of the one or more wearable devices may provide monitored diagnostic information to a trained model which identifies the subject's risk of a cardiac event. Upon detection of a high risk of present or future cardiac event, a notification may be provided to the subject and/or their physician.

The trained model may reside in the wearable device, a subject's mobile device, a subject's desktop computer, a cloud-based system, or a remote server accessible through the internet or a local intranet.

Training the model may include one or more of the methodologies described herein with the addition of the instantaneous readings and/or readings over time captured from the one or more wearable devices. In some examples, the measurements taken from the wearable devices may replace one or more features of the inputs to the model such as those for measuring heart rate, heart rhythm, blood pressure, or one or more ECG or ECG-like leads.

For the purposes of training a model to predict high risk of a cardiac event from the diagnostic data collected from a wearable device, a model may be trained using only diagnostic data collected from the wearable device, a model trained from the diagnostic data collected from a wearable device may be improved or fine-tuned using additional data outside of the diagnostic data, or a model which has previously been trained on a dataset may be translated to operate on the diagnostic data collected from a wearable device.

For example, a model may be trained on ECG data such as a 12-lead electrocardiogram (ECG) can include a I Lateral lead (also referred to as a I lead), a II Inferior lead (also referred to as a II lead), a III Inferior lead (also referred to as a III lead), an aVR lead, an aVL Lateral lead (also referred to as an aVL lead), an aVF Inferior lead (also referred to as an aVF lead), a V1 Septal lead (also referred to as a V1 lead), a V2 Septal lead (also referred to as a V2 lead), a V3 Anterior lead (also referred to as a V3 lead), a V4 Anterior lead (also referred to as a V4 lead), a V5 Lateral lead (also referred to as a V5 lead), and a V6 Lateral lead (also referred to as a V6 lead).

Although the present disclosure discusses data ingestion from a 12-lead ECG, it should be understood that it may be employed using data ingested from ECGs with more or fewer leads, provided the ECG used for training relies on a larger number of leads than the clinical or consumer device that is later used.

Similarly, although the portable or consumer devices to which the trained model is applied are generally referred to herein as having one lead, it should be understood that they may include a larger number of leads, provided that number is smaller than the number of leads on which the AI model is trained. For example, the device may be a single lead device such as a smart watch or other device worn on the wrist or a device worn around the chest. Alternatively, the device may be a multi-lead device such as a garment with a pair of embedded leads. Still further, the device may be a smaller, portable ECG device with, e.g., 1 to 6 leads, or it may even be a clinical grade device, e.g., with 12 leads. In the lattermost case, the device still preferably includes fewer leads than the device(s) from which the clinical data is obtained.

The present disclosure has applicability to multiple areas of medicine in which patient data is obtained via multi-lead ECGs. Such areas may include, but are not limited to, cardiology, oncology, endocrinology, and medical diagnostics. Such areas may benefit from the transfer learning method disclosed herein due to the variability that is introduced in data collection in each area. For example, in cardiology, oncology, and/or endocrinology, different machines will generate different reads, so the transfer learning method makes it possible to evaluate this disparate data from one machine to the next, particularly without having to batch normalize the data. Similarly, with regard to medical diagnostics, different labs may have their own procedures, biases, ranges for what is normal, etc. Additionally, data received from one patient or cohort of patients may need to be modified in order to render it applicable to a second cohort of patients, e.g., data from male patients and what is considered within normal ranges for them may need to be adjusted to apply it to female patients. Such modifications also may be accomplished through the transfer learning methods disclosed herein.

The present disclosure employs a transfer learning method to train millions of AI model parameters to predict a patient's current or future health status with millions of 12-lead ECGs and paired clinical data from a healthcare provider. The method then includes taking the trained 12-lead model, extracting interpretation units for individual leads, and then reconstructing a model that will process data received from a clinical or consumer device that employs fewer leads. The method then applies a fine-tuning step in which the reconstructed model learns to adapt to the new device's data, where that step requires just a couple hundred samples (as opposed to the original millions).

Figure 29:
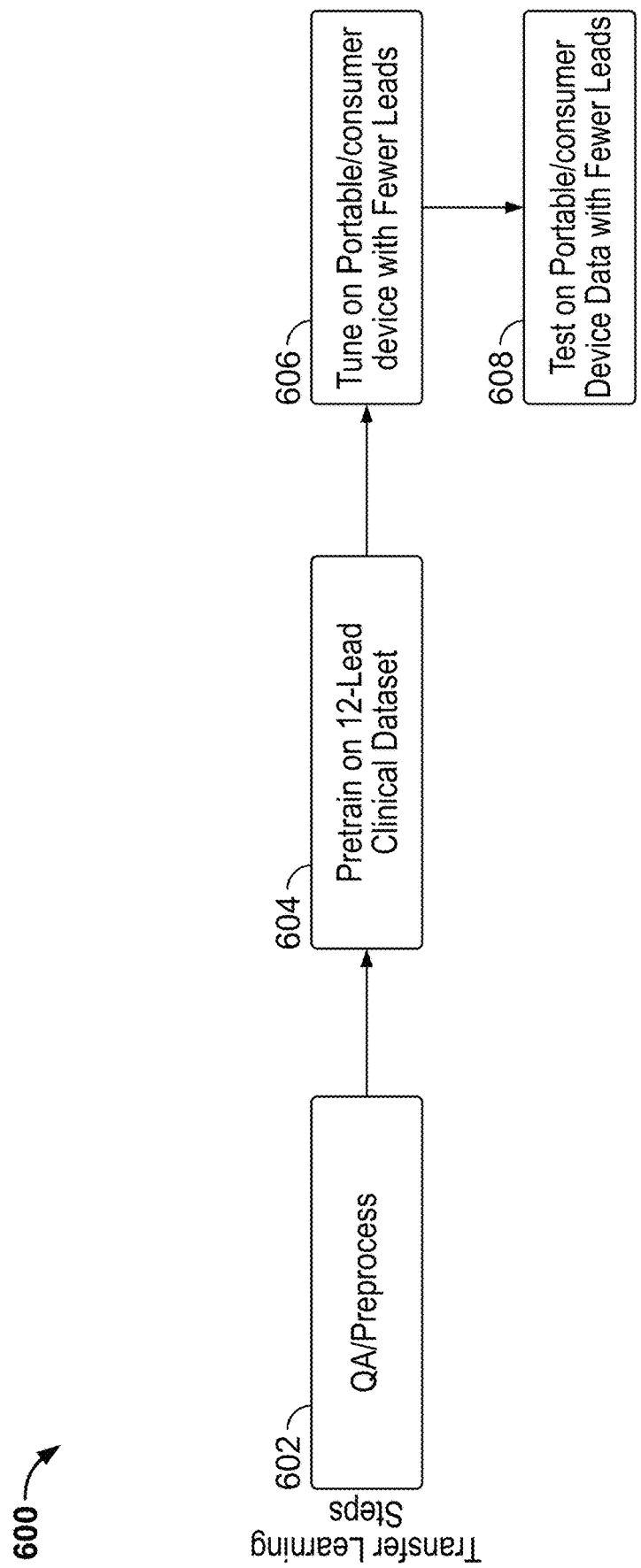
FIG. 29 is an example of a method for translating AI algorithms from multi-lead clinical ECGs to portable and consumer ECGs with fewer leads.

Referring to FIG. 29, the method 600 may include one or more steps of data ingestion, QA, or preprocessing 602. In particular, the method may include time-series signal processing of ECG data and artifact detection and exclusion. Ingestion may include, e.g., a plurality of voltage-time traces where a first subset are stored at a first frequency, e.g., 500 Hz, and a second subset are stored at a second, different frequency, e.g., 250 Hz. Such data may be batch loaded due to the exceedingly large volume of clinical data being ingested, and similar batch techniques may be applied to one or both of the training or prediction steps disclosed herein.

A preprocessing stage may include resampling the 250 Hz ECGs to 500 Hz by linear interpolation. Artifacts may include those identified by ECG software at the time of ECG; for example, ECG outputs that include "technically limited", "motion/baseline artifact", "Warning: interpretation of this ECG, although attempted, may be adversely affected by data quality", "Acquisition hardware fault prevents reliable analysis", "Suggest repeat tracing", "chest leads probably not well placed", "electrical/somatic/power line interference", or "Defective ECG".

Pre-processing also may include identifying and excluding one or more subsets of data. For example, when the model is designed to analyze individuals with respect to atrial fibrillation, a lead voltage over 12 mV may be considered an exclusion criterion and/or considered to usually occur as a result of motion artifacts. Thus, the method may perform a quality check in such instances and remove all ECG lead data at or above that threshold level. In another example, lead data reading 0 mV may be considered to result from a dead lead and may be deleted from the training set. Conversely, the method may retain such data for its model, recognizing that doing so may result in a dataset and model that are more robust.

Pre-processing also may be applied to data received from the portable or consumer device. For example, such devices may sample at a different, lower frequencies than clinical ECGs, so such data also may be processed, e.g., by linear interpolation, to adjust for the difference.

At step 604, the deep neural network parameters may be pretrained on millions of 12-lead ECGs. This can involve just ECG data (unsupervised), or it may leverage associated clinical data (supervised). In some embodiments, the clinical data can include outcome data, such as whether or not a patient developed AF in a time period following the day that the ECG was taken.

The method also may include mid-training network modification. For example, the network may be pruned and a single channel featurization unit may be isolated. Such pruning may be useful to adapt the network to the specific portable or consumer device being used. For example, for wrist-worn devices, the system may determine that a model trained and isolated on readings taken from I lead or II lead may be most similar or most applicable. Alternatively, the system may determine that data derived from a different lead or combination of leads may be most applicable for a chest-worn device that is placed over the wearer's heart. One such pruning is done, new neural layers then may be added to connect a single channel's features to a new classification layer.

Subsequently, at step 606, the method may resume training on a 1-channel ECG dataset to fine-tune the model and then at step 608 apply and evaluate the model on data obtained from smaller-channel ECGs, e.g., 1-channel ECGs.

In some embodiments, the method may be diagnostic, whereby the clinical data can include outcome data, such as whether or not a patient developed atrial fibrillation (AF or Afib) in a time period following the day that the ECG was taken. In other embodiments, the clinical data may be used in a predictive sense, e.g., to determine based on that data a likelihood that the patient would develop Afib within a certain time period following the day that the ECG was taken.

AF is a cardiac rhythm disorder associated with several important adverse health outcomes including stroke and heart failure. In patients with AF and risk factors for thromboembolism, early anticoagulation has been shown to be effective at preventing strokes. Unfortunately, AF often goes unrecognized and untreated since it is frequently asymptomatic or minimally symptomatic. Thus, systems and methods to screen for and identify undetected AF can assist in preventing strokes.

Population-based screening for AF is challenging for two primary reasons. One, the yearly incidence of AF in the general population is low with reported incidence rates of less than 10 per 1000 person years under the age of 70. Two, AF is often "paroxysmal" (the patient goes in and out of AF for periods of time) with many episodes lasting less than 24 hours. Currently, the most common screening strategy is opportunistic pulse palpation, sometimes in conjunction with a 12-lead electrocardiogram during routine medical visits. This has been shown to be cost-effective in certain populations and is recommended in some guidelines. However, studies of implantable cardiac devices have suggested that this strategy will miss many cases of AF.

A number of continuous monitoring devices are now available to detect paroxysmal and asymptomatic AF. Patch monitors can be worn for up to 14-30 days, implantable loop recorders provide continuous monitoring for as long as 3 years, and wearable monitors, sometimes used in conjunction with mobile devices, can be worn indefinitely. Continuous monitoring devices overcome the problem of paroxysmal AF but must still contend with the overall low incidence of new onset AF and cost and convenience limit their use for widespread population screening.

Figure 30:
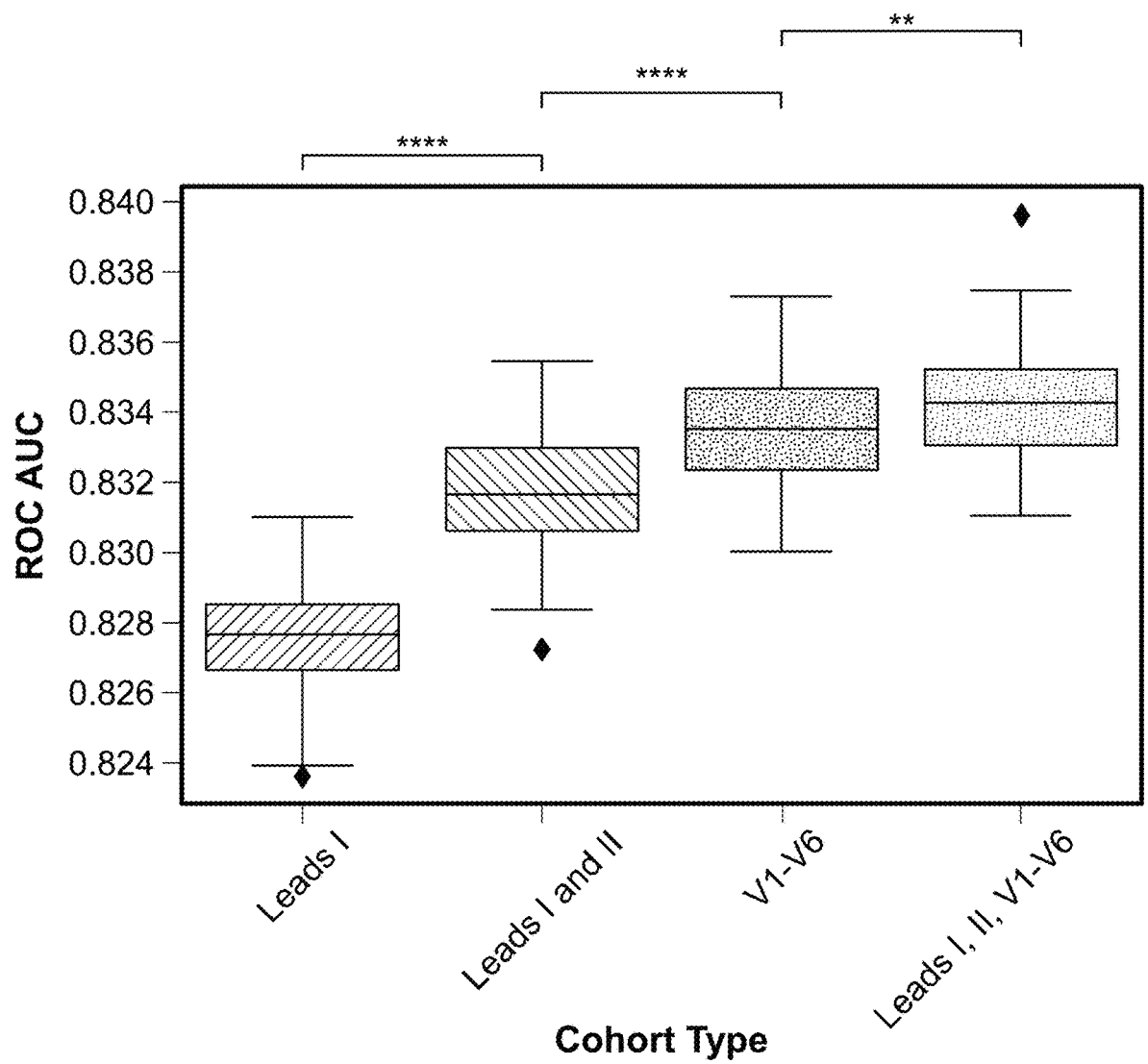
FIG. 30 is a bar chart of model performance as mean area under the receiver operating characteristic.
Figure 31:
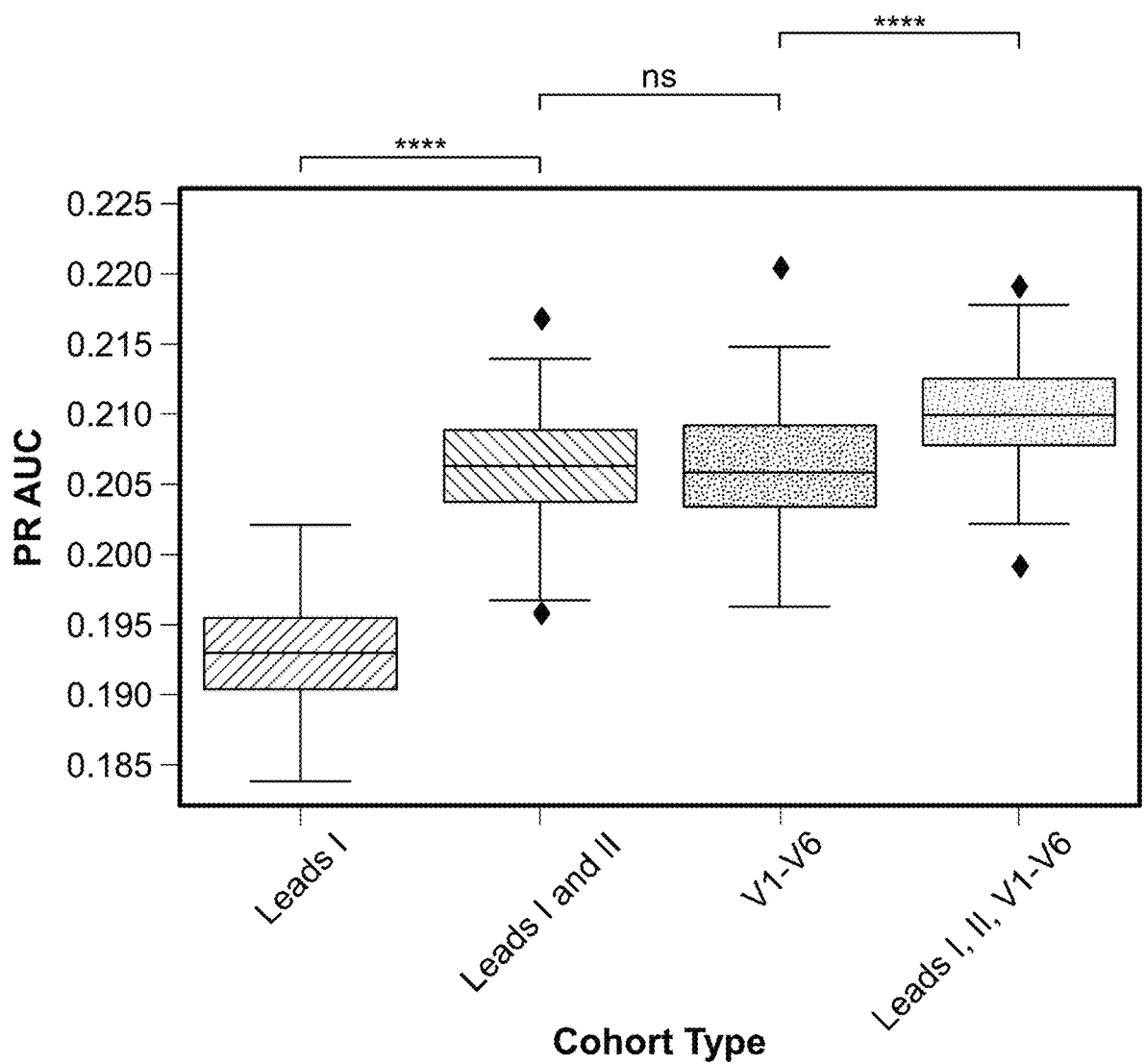
FIG. 31 is a bar chart of model performance as mean area under the precision-recall curve.

FIGS. 30 and 31 provide model performance metrics for 1 yr first time incident Afib risk towards patients aged >=18 years. In both cases, Mann-Whitney U tests with Bonferroni corrections were used to assess significant differences between groups. "***" indicates statistically significant with a p-value <0.05, "ns" indicates that the difference between groups was not statistically significant, and "" indicates some statistical significance.

In particular, model performance in FIG. 30 is depicted using receiver operating characteristic area under the curve (ROC AUC). ROC AUC is a robust metric of model performance that represents the ability to discriminate between two classes. Higher ROC AUC suggests higher performance (with perfect discrimination represented by an ROC AUC of 1 and an AUROC of 0.5 being equivalent to a random guess).

Model performance in FIG. 31 is depicted using precision recall area under the curve (PR AUC). PR AUC is an average precision score determined by computing weighted average of precisions achieved at each threshold by the increase in recall.

The ROC AUC and PRC AUC of the model for the prediction of new onset AF within 1 year were approximately 0.828, 95% CI [0.827, 0.829] and 0.194 [0.192, 0.197], respectively, for Lead I, 0.832 [0.831, 0.833] and 0.207 [0.205, 0.209], respectively, for Leads I and II, 0.833 [0.0832, 0.835] and 0.207 [0.205, 0.210], respectively, for Leads V1-V6, and 0.834 [0.833, 0.836] and 0.210 [0.209, 0.211], respectively, for Leads I, II, and V1-V6.

These results demonstrate that the AI model may be properly trained on clinical data and then applied to data received from portable or consumer devices, permitting the use of cardiology analysis outside of a clinical setting.

FIGS. 4A and 4B are exemplary embodiments of models usable with the method disclosed herein. The disclosure provided above with respect to those models also is applicable to the examples and methods disclosed herein.

In one embodiment, the convolutional neural networks, such as those depicted in FIGS. 4A and 4B, may be trained on a first set of data and translated to perform on a second set of data. In one example, the first set of data may be robust and include large quantities of samples from which to train while the second set of data may be sparse and include only a few quantities of samples. In another example, the first set of data may include more operational parameters or features, such as having access to more clinical data or more complete diagnostic data. Diagnostic data may include those from different disease states such as oncology, cardiology, endocrinology, and diagnostic laboratory testing. In the field of oncology, for example, a first dataset may include the full RNA transcriptome and subsequent read quantities generated from next generation sequencing while the second set of data may have been generated from a greatly reduced number of transcriptomes such as those generated from a smaller panel or microarray.

In another example, a model may be translated from training from one sequencing laboratory to another sequencing laboratory due to the differences in the laboratories' equipment or sequencing procedures. In such an example, the datasets may not be categorized as a robust to sparse but instead as robust to robust, but where there exists disparity between the data. One aspect of translating a model trained on a robust dataset to another robust dataset is that the model maintains performance while becoming generalizable across many different robust datasets without concern for where they were generated.

Multiple embodiments may be implemented on data varying in quantity, quality, and number of features. In general, a model may be trained on a dataset having high quantity of samples, higher quality of samples, and/or higher number of features for each sample, and may be translated to a dataset having a lower quantity of samples, lower quality of samples, and/or a lower number of features for each sample. In this manner, higher quality predictive algorithms may be adapted for performance on datasets having one or more disadvantages that preclude the dataset from being used to generate a higher quality model.

Similar to RNA as presented above a model trained on a first DNA panel may be translated using a second DNA panel in whether a robust to sparse translation or a robust to robust translation.

If a user attempted to plug the reduced data set into a model trained from the robust dataset, the results generated would not be accurate due to the differences in data. However, if the model was translated from the first dataset to the second dataset, much of the performance of the model generated from the robust training set of data may be retained for use with the reduced set of data.

In the field of endocrinology, a similar translation may be performed, for example, on sequencing data generated for treating a patient having diabetes, or other endocrinological diagnosis.

In the field of mental health, a similar translation may be performed, for example, on sequencing data generated for treating a patient having depression, or other mental health diagnosis.

In the field of laboratory testing, a similar translation may be performed, for example, on diagnostic laboratory tests for metabolic panels, blood panels, viral or bacterial panels, or other laboratory diagnostic testing.

Steps for translating the model may include performing one or more transfer learning methodologies.

In the field of cardiology, the robust dataset may include 12 lead ECGs across millions of patients while the reduced dataset may be limited to a few leads such as those generated from one or more wearable devices. In some embodiments, the translation may be performed across different ECG collection devices, whether having the same number of leads in a robust to robust translation, a differing number of leads in a robust to robust translation, a same number of leads in a robust to sparse translation, or a differing number of leads a robust to sparse translation, where robust may refer to the number of samples in the dataset, the quality of samples in the dataset, or the number of features associated with the samples of the dataset.

Before training, a time-series signal processing of ECG data including artifact detection and exclusion may be performed. This includes preprocessing steps such as sampling normalization, voltage trace structure changes, and possible inclusions of noisy data to regularize deep learning models. For example, dead leads and/or spikes in millivolts may be identified (such as over 12 mv).

The deep neural network parameters may be pretrained on millions of 12-lead ECGs. This can involve just ECG data (unsupervised), or it may leverage associated clinical data such as patient demographics, diagnoses, or cardiac anatomy and functional measures (blood flow from heart) (supervised). In some embodiments, the clinical data can include outcome data, such as whether or not a patient developed AF in a time period following the day that the ECG was taken. The resulting neural network may be composed of model specific convolutional layer blocks, and/or fully connected layers, such as those presented in exemplary architectures 9a and 9b.

The method also may include mid-training network modification. For example, the network may be pruned and a single channel featurization unit may be isolated. Such pruning may be useful to adapt the network to the specific portable or consumer device being used. For example, for wrist-worn devices, the system may determine that a model trained and isolated on readings taken from I lead or II lead may be most similar or most applicable. Alternatively, the system may determine that data derived from a different lead or combination of leads may be most applicable for a chest-worn device that is placed over the wearer's heart. By identifying a corresponding lead within the trained convolutional network, it may be held out from pruning or selected for pruning based on the desire to include or exclude it from the translated model. One such pruning is done, new neural layers then may be added to connect a single channel's features to a new classification layer.

In one embodiment, the frozen layers may be the GAP layers of FIGS. 4A and 4B. In another embodiment, the frozen layers may be the dense layers of FIGS. 4A and 4B. In yet another embodiment, one or more of the GAP layers may be selected for freezing and or other layers as identified using the rule set or heuristic algorithms.

In another example, pruning the network and extracting a subset (1 to 12) of the lead featurization units may be performed via a derived insights table with pre-programmed rules, or in a programmatic manner using one or optimization or heuristic models before adding new neural layers to connect channel features to a new classification layer.

Subsequently the translation steps may resume training on a 1-channel ECG dataset to fine-tune the model and before being able to apply and evaluate the transformed model on data obtained from smaller-channel ECGs, e.g., 1-channel ECGs. Fine tuning may include training on a dataset that matches the pruned input structure. Fine-tuning strategies can either freeze the extracted ECG layers and retrain the unfrozen final layers, or "un-freezing" the ECG layers to further modify the featurization of ECG leads. Modifying which layers are exempt from retraining at each fine-tuning iteration enables the model to select for the best layers to reweigh and improve the resulting translated model.

In one embodiment, the frozen layers may be the GAP layers of FIGS. 4A and 4B. In another embodiment, the frozen layers may be the dense layers of FIGS. 4A and 4B. In yet another embodiment, one or more of the GAP layers may be selected for freezing and or other layers as identified using the rule set or heuristic algorithms.

In some embodiments, the method may be diagnostic, whereby the clinical data can include outcome data, such as whether or not a patient developed atrial fibrillation (AF or Afib) in a time period following the day that the ECG was taken. In other embodiments, the clinical data may be used in a predictive sense, e.g., to determine based on that data a likelihood that the patient would develop Afib within a certain time period following the day that the ECG was taken.

While examples provided herein include one or more combinations of model inputs, exemplary combinations of model inputs may be selected from any patient features within the EMR.

While the invention may be susceptible to various modifications and alternative forms, specific embodiments have been shown by way of example in the drawings and have been described in detail herein. However, it should be understood that the invention is not intended to be limited to the particular forms disclosed.

Thus, the invention is to cover all modifications, equivalents, and alternatives falling within the spirit and scope of the invention as defined by the following appended claims.

To apprise the public of the scope of this invention, the following claims are made:

What is claimed is:

1. A method for determining cardiac disease risk from electrocardiogram trace data and clinical data, comprising:
   receiving electrocardiogram trace data associated with a patient, the electrocardiogram trace data having an electrocardiogram configuration including a plurality of leads and a time interval and comprising, for each lead included in the plurality of leads, voltage data associated with at least a portion of the time interval;
   receiving clinical data associated with the patient;
   providing the clinical data and at least a portion of the electrocardiogram trace data to a trained machine learning model, the model trained to evaluate the clinical data and the portion of the electrocardiogram trace data with respect to one or more cardiac disease states;
   generating, by the trained machine learning model and based on the evaluation, a risk score reflecting a likelihood of the patient being diagnosed with a cardiac disease state within a predetermined period of time from when the electrocardiogram trace data was generated; and
   outputting the risk score to at least one of a memory or a display.

2. The method of claim 1, wherein the clinical data comprises age and gender of the patient.

3. The method of claim 2, further comprising:
providing the at least a portion of the electrocardiogram trace data to a convolutional neural network; and
providing the age and gender to a boosting model.

4. The method of claim 1, wherein the trained model further comprises:
training a convolutional neural network on a first plurality of patients and a second plurality of patients, wherein a time between a date of a recorded ECG and a diagnosis of aortic stenosis for each of the first plurality of patients is less than a diagnosis threshold, and a time between a date of a recorded ECG and a diagnosis of aortic stenosis for each of the second plurality of patients is greater than the diagnosis threshold; wherein a time between a date of a recorded ECG and a diagnosis of aortic stenosis that is less than the diagnosis threshold is indicative of an active aortic stenosis at the date of the recorded ECG; and
providing the trained convolutional neural network as the trained model.

5. The method of claim 4, wherein the trained model further comprises:
refining the trained neural network using only the second plurality of patients, and wherein the diagnosis threshold is selected from a number of days.

6. The method of claim 1, wherein the trained model is selected based at least in part on a severity of the cardiac disease state the generated risk score represents.

7. The method of claim 6, wherein the severity includes labels for one or more of normal, mild, moderate, and severe.

8. The method of claim 1, wherein the predetermined period of time includes times at least one year from when the electrocardiogram trace data was generated.

9. The method of claim 1, wherein the trained model comprises training data associated with a plurality of clinical sites.

10. The method of claim 9, wherein the trained model comprises training the model using patient data associated with one site of the plurality of sites and testing the trained model on the remaining sites of the plurality of sites.

11. The method of claim 1, wherein the outputting the risk score further comprises outputting the risk score to a display of an electrocardiogram monitor, wherein the received electrocardiogram trace data is received from the electrocardiogram monitor.

12. The method of claim 1, wherein the outputting the risk score further comprises outputting the risk score to an electronic health records management system.

13. The method of claim 1, wherein the clinical data is selected from demographic data, vitals data, laboratory data, or comorbidities data.

14. The method of claim 13, wherein the vitals data comprises one or more of body mass index, systolic blood pressure, diastolic blood pressure, heart rate, height, weight, or smoking status.

15. The method of claim 13, wherein the laboratory data comprises one or more of A1C, bilirubin, blood urea nitrogen, cholesterol, creatine kinase myocardial band, creatinine, C-reactive protein, D-dimer, glucose, high-density lipoprotein, hemoglobin, high-density lipoprotein, lactate dehydrogenase, lymphocytes, potassium, pro B-type natriuretic peptide, sodium, troponin I and T, triglyceride, uric acid, very low density lipoprotein, or estimated glomerular filtration rate.

16. The method of claim 13, wherein the comorbidities data comprises one or more of heart failure, prior myocardial infarction, diabetes mellitus, chronic obstructive pulmonary disease, renal failure, prior echocardiogram, coronary artery disease, or hypertension.

17. The method of claim 1, wherein the electrocardiogram trace data comprises ECG data selected from one or more of acute myocardial infarction, atrial fibrillation, atrial flutter, complete block, early repolarization, fascicular block, first-degree atrioventricular block, intraventricular conduction block, left bundle branch block, right bundle branch block, ischemia, left anterior descending artery ischemia, right bundle branch block, low QRS, left ventricular hypertrophy, non-specific ST-T wave, Non-specific T wave, other bradycardia, premature atrial contractions, pacemaker, poor tracing, prior infarction, prior myocardial infarction anterior, prolonged QT, premature ventricular contractions, right axis deviation, second degree atrioventricular block, sinus bradycardia, supraventricular tachycardia, tachycardia, tachyarrhythmia, T inversion, or ventricular tachycardia.

18. The method of claim 1, further comprising gathering the clinical data and electrocardiogram trace data based at least in part on a presence of ICD codes associated with the patient.

19. The method of claim 1, wherein the electrocardiogram trace data comprises at least 8 leads.

20. The method of claim 1, wherein the electrocardiogram trace data is sampled at 250 hz or 500 hz.

21. The method of claim 1, wherein the trained model is a composite model, and wherein training the trained composite model comprises:
generating a patient timeline for each patient;
anchoring each respective patient timeline to a date of occurrence of an echocardiogram; and
labeling each respective patient as having a positive or negative ECG based at least in part on a date of an ECG with respect to the date of occurrence of the echocardiogram.

22. The method of claim 21, further comprises excluding patients from training after a censoring event is detected in the patient timeline.

23. The method of claim 1, wherein the cardiac disease state is one of aortic stenosis, aortic regurgitation, mitral stenosis, mitral regurgitation, tricuspid regurgitation, reduced ejection fraction, increased interventricular septal thickness, cardiac amyloidosis, or stroke.

24. A system comprising:
a computer including a processing device, the processing device configured to:
receive electrocardiogram trace data associated with a patient, the electrocardiogram trace data having an electrocardiogram configuration including a plurality of leads and a time interval and comprising, for each lead included in the plurality of leads, voltage data associated with at least a portion of the time interval;
receive clinical data associated with the patient;
provide the clinical data and at least a portion of the electrocardiogram trace data to a trained machine learning model, the model trained to evaluate the clinical data and the portion of the electrocardiogram trace data with respect to one or more cardiac disease states;
generate, by the trained machine learning model and based on the evaluation, a risk score reflecting a likelihood of the patient being diagnosed with a cardiac disease state within a predetermined period of time from when the electrocardiogram trace data was generated; and
output the risk score to at least one of a memory or a display.

25. The system of claim 24, wherein the clinical data comprises age and gender of the patient.

26. The system of claim 24, wherein the cardiac disease state is one of aortic stenosis, aortic regurgitation, mitral stenosis, mitral regurgitation, tricuspid regurgitation, reduced ejection fraction, increased interventricular septal thickness, cardiac amyloidosis, or stroke.

27. A non-transitory computer readable medium, comprising instructions for causing a computer to:
receive electrocardiogram trace data associated with a patient, the electrocardiogram trace data having an electrocardiogram configuration including a plurality of leads and a time interval and comprising, for each lead included in the plurality of leads, voltage data associated with at least a portion of the time interval;
receive clinical data associated with the patient;
provide the clinical data and at least a portion of the electrocardiogram trace data to a trained machine learning model, the model trained to evaluate the clinical data and the portion of the electrocardiogram trace data with respect to one or more cardiac disease states;
generate, by the trained machine learning model and based on the evaluation, a risk score reflecting a likelihood of the patient being diagnosed with a cardiac disease state within a predetermined period of time from when the electrocardiogram trace data was generated; and
output the risk score to at least one of a memory or a display.

28. The non-transitory computer readable medium of claim 27, wherein the clinical data comprises age and gender of the patient.

29. The non-transitory computer readable medium of claim 27, wherein the cardiac disease state is one of aortic stenosis, aortic regurgitation, mitral stenosis, mitral regurgitation, tricuspid regurgitation, reduced ejection fraction, increased interventricular septal thickness, cardiac amyloidosis, or stroke.

* * * * *